US012573474B2

(12) United States Patent
    Ryoo et al.

(10) Patent No.: US 12,573,474 B2
(45) Date of Patent: Mar. 10, 2026

(54) METHOD FOR PROVIDING TARGET NUCLEIC ACID SEQUENCE DATA SET OF TARGET NUCLEIC ACID MOLECULE

(71) Applicant: SEEGENE, INC., Seoul (KR)

(72) Inventors: Hyunju Ryoo, Seoul (KR); Hyunho Kim, Seoul (KR)

(73) Assignee: SEEGENE, INC., Seoul (KR)

( * ) Notice: Subject to any disclaimer, the term of this patent is extended or adjusted under 35 U.S.C. 154(b) by 1215 days.

(21) Appl. No.: 17/049,075

(22) PCT Filed: Apr. 30, 2019

(86) PCT No.: PCT/KR2019/005227
    § 371 (c)(1),
    (2) Date: Oct. 20, 2020

(87) PCT Pub. No.: WO2019/212238
    PCT Pub. Date: Nov. 7, 2019

(65) Prior Publication Data

US 2021/0257054 A1     Aug. 19, 2021

(30) Foreign Application Priority Data

Apr. 30, 2018    (KR) ........................ 10-2018-0050035

(51) Int. Cl.
    *G16B 30/10*        (2019.01)
    *G16B 50/30*        (2019.01)
(52) U.S. Cl.
    CPC ............. *G16B 30/10* (2019.02); *G16B 50/30* (2019.02)
(58) Field of Classification Search
    CPC ........ G16B 30/10; G16B 50/30; G16B 30/20; G16B 30/00; G16B 50/00; C12Q 1/6869
    See application file for complete search history.

(56) References Cited

U.S. PATENT DOCUMENTS

2003/0033290 A1    2/2003  Garner et al.
2004/0126840 A1    7/2004  Cheng et al.
2007/0225920 A1    9/2007  Kim et al.
2010/0318528 A1    12/2010 Kupershmidt et al.

FOREIGN PATENT DOCUMENTS

WO     WO-2007047904 A1 *   4/2007   ............. G06F 19/28
WO     WO-2013/023220 A2    2/2013

OTHER PUBLICATIONS

Chang J. Biopython Tutorial and Cookbook. 332 pgs. (Year: 2016).*
Li W. Saturated Blast: an automated multiple intermediate sequence search used to detect distant homology. Bioinformatics 16(12): 1105-1110. (Year: 2000).*
International Search Report from corresponding PCT Application No. PCT/KR2019/005227, dated Aug. 28, 2019, 7 pages.
Y. P. Bao et al., "SNP identification in unamplified human genomic DNA with gold nanoparticle probes", Nucleic Acids Research, 33(2):e15. (Jan. 1, 2005).
F. Iragne et al., "AliasServer: a web server to handle multiple aliases used to refer to proteins", Bioinformatics, 20(14):2331-2332. (Apr. 1, 2004).
H. Sobhy, "Shetti, a simple tool to parse, manipulate and search large datasets of sequences", Microbial Genomics, 1(5):e000035. (Nov. 6, 2015).
K. Bussow et al., "ORFer—retrieval of protein sequences and open reading frames from GenBank and storage into relational databases or text files", BMC Bioinformatics, 3:40. (Dec. 19, 2002).
Notice of Allowance from corresponding Korean Patent Application No. 9-5-2023-062294420, dated Jul. 7, 2023.

* cited by examiner

*Primary Examiner* — Olivia M. Wise
*Assistant Examiner* — Robert J. Kallal
(74) *Attorney, Agent, or Firm* — Harness, Dickey & Pierce, P.L.C.

(57)                ABSTRACT

The present invention provides a method for providing a target nucleic acid sequence data set of a target nucleic acid molecule. The larger number of synonyms are retrieved from reliable sources than that of synonyms extracted by user experience. Thus, the target nucleic acid sequence data group of the target nucleic acid molecule retrieved based on the larger number of synonyms may cover various variant sequences of the target nucleic acid molecule.

8 Claims, 12 Drawing Sheets

Specification includes a Sequence Listing.

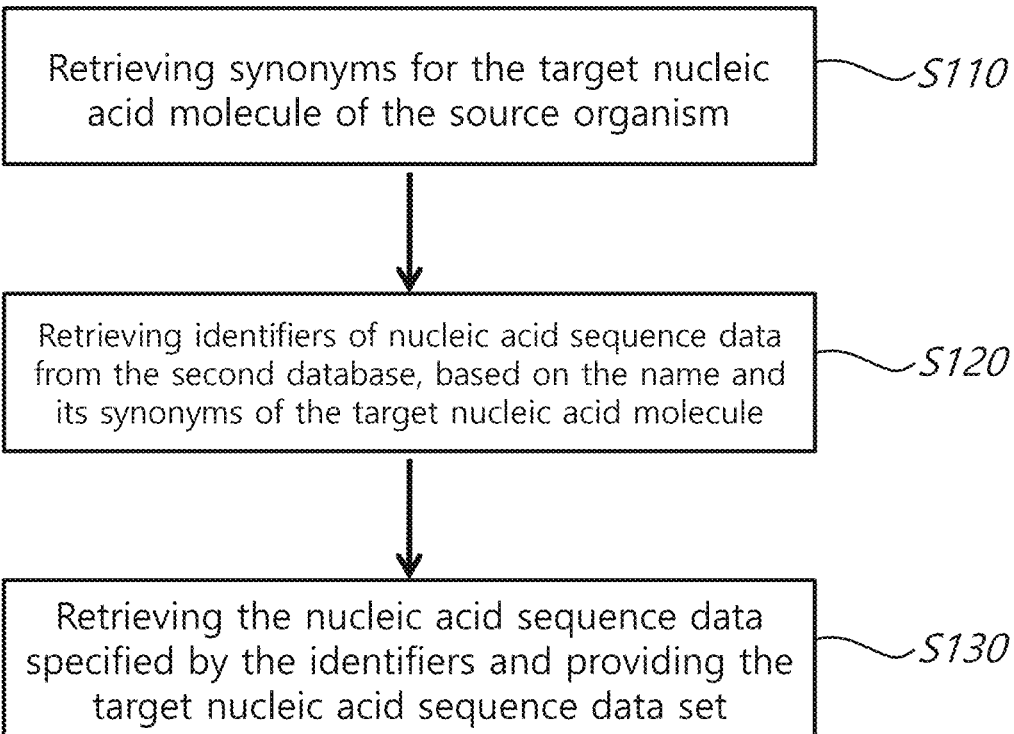

_100_

Retrieving synonyms for the target nucleic
acid molecule of the source organism          ~S110

Retrieving identifiers of nucleic acid sequence data
from the second database, based on the name and
its synonyms of the target nucleic acid molecule          ~S120

Retrieving the nucleic acid sequence data
specified by the identifiers and providing the
target nucleic acid sequence data set          ~S130

FIG. 1

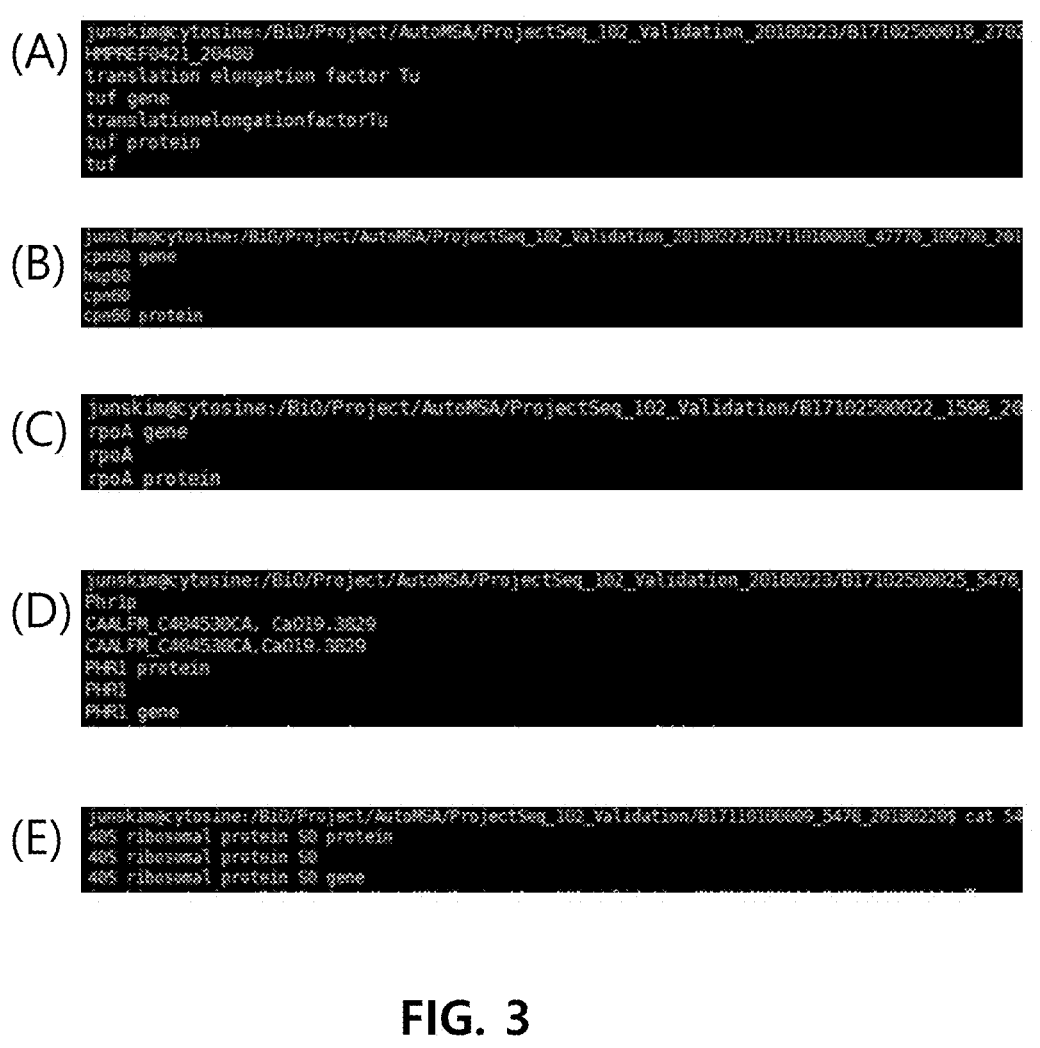

(A)
```
junskimgcytosine:/BiO/Project/AutoMSA/ProjectSeq_102_Validation_20180223/817102500019_370X
HMMEF0021_20480
translation elongation factor Tu
tuf gene
translationelongationfactorTu
tuf protein
tuf
```

(B)
```
junskimgcytosine:/BiO/Project/AutoMSA/ProjectSeq_102_Validation_20180223/817101500088_4770_180788_201
cpn60 gene
hsp60
cpn60
cpn60 protein
```

(C)
```
junskimgcytosine:/BiO/Project/AutoMSA/ProjectSeq_102_Validation/817102500022_1596_20
rpoA gene
rpoA
rpoA protein
```

(D)
```
junskimgcytosine:/BiO/Project/AutoMSA/ProjectSeq_102_Validation_20180223/817102500025_5476
Phr1p
CAAL_FM_C004530CA, CaO19.3829
CAAL_FM_C004530CA, CaO19.3829
PHR1 protein
PHR1
PHR1 gene
```

(E)
```
junskimgcytosine:/BiO/Project/AutoMSA/ProjectSeq_102_Validation/817101500088_5476_20180209_cat_50
40S ribosomal protein S0 protein
40S ribosomal protein S0
40S ribosomal protein S0 gene
```

FIG. 3

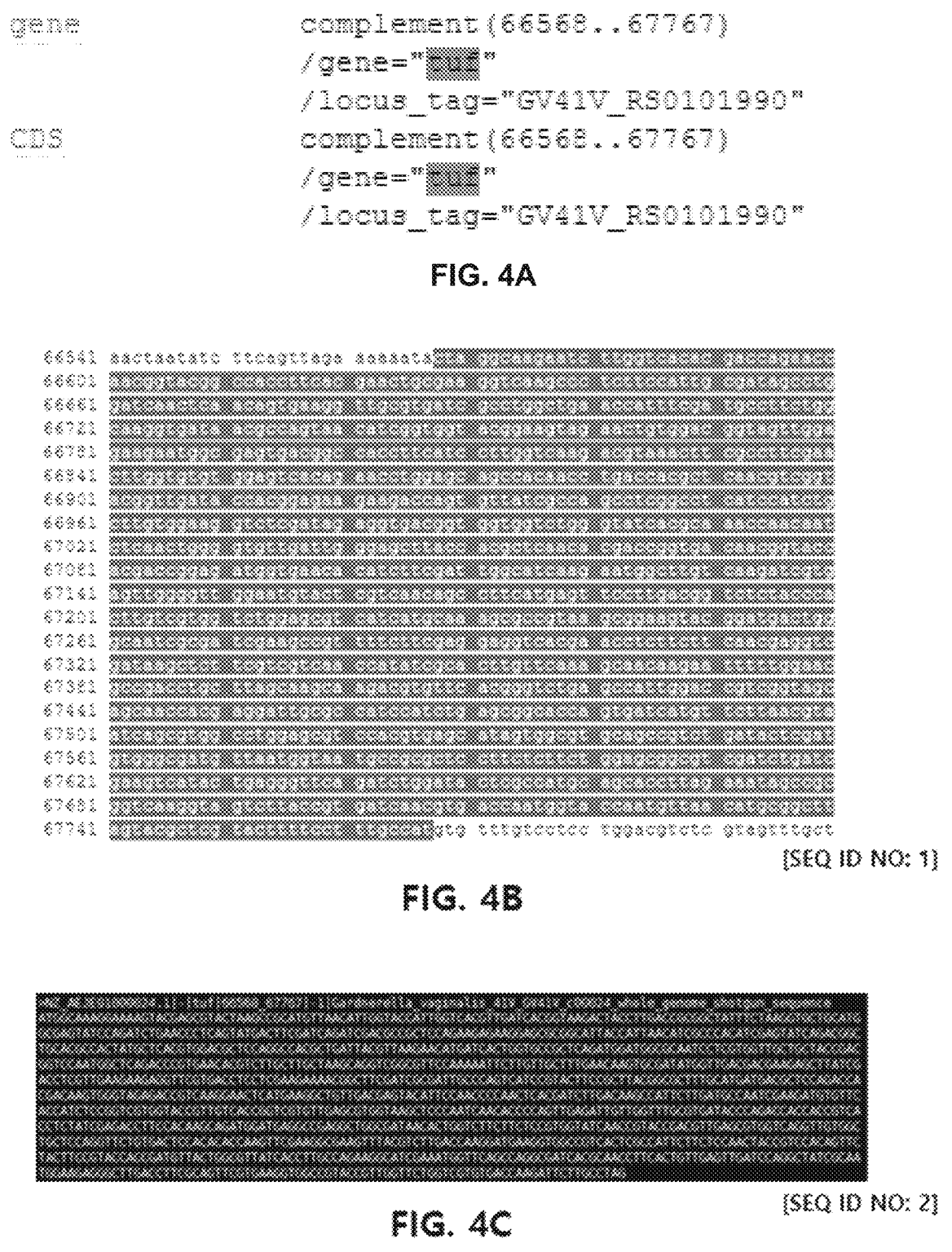

```
gene              complement(66568..67767)
                  /gene="████"
                  /locus_tag="GV41V_RS0101990"
CDS               complement(66568..67767)
                  /gene="████"
                  /locus_tag="GV41V_RS0101990"
```

FIG. 4A

[SEQ ID NO: 1]

FIG. 4B

[SEQ ID NO: 2]

FIG. 4C

File  Edit  Select  View  Annotations  Format  Colour  Calculate  Web Service (3) : SEQ ID NO: 3   (10) : SEQ ID NO: 10
(4) : SEQ ID NO: 4   (11) : SEQ ID NO: 11
(5) : SEQ ID NO: 5   (12) : SEQ ID NO: 12
(6) : SEQ ID NO: 6   (13) : SEQ ID NO: 13
(7) : SEQ ID NO: 7   (14) : SEQ ID NO: 14
(8) : SEQ ID NO: 8   (15) : SEQ ID NO: 15
(9) : SEQ ID NO: 9   (16) : SEQ ID NO: 16

_200_

Determining a representative sequence from the first target nucleic acid sequence data set ⟋S210

Retrieving nucleic acid sequence data having homology with the representative sequence at a predefined homology value or greater ⟋S220

Providing an extended target nucleic acid sequence data set of the target nucleic acid molecule ⟋S230

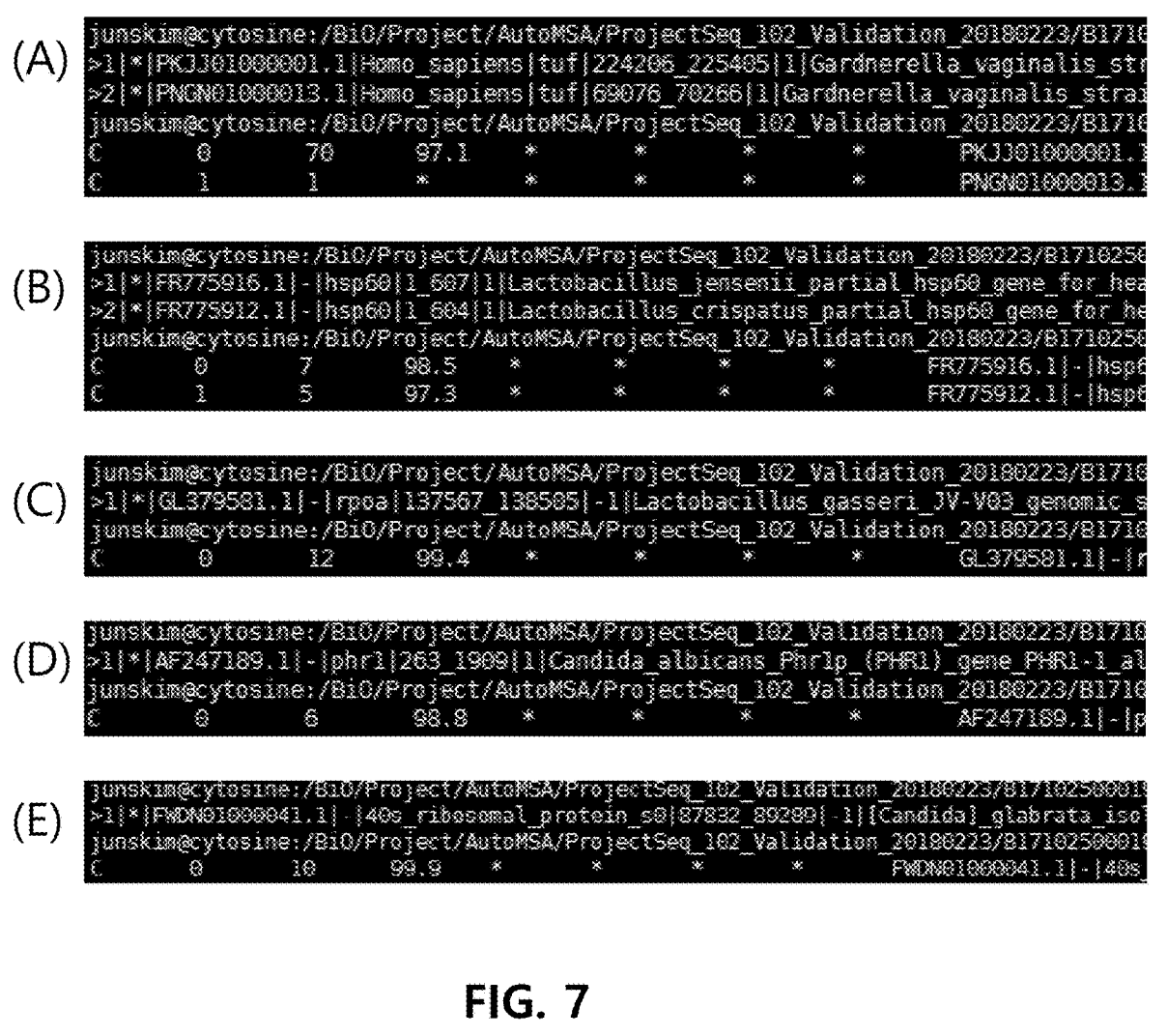

(A)

```
junskim@cytosine:/BiO/Project/AutoMSA/ProjectSeq_102_Validation_20180223/B1710
>1|*|PKJJ01000001.1|Homo_sapiens|tuf|224206_225405|1|Gardnerella_vaginalis_str
>2|*|PNGN01000013.1|Homo_sapiens|tuf|69076_70266|1|Gardnerella_vaginalis_strai
junskim@cytosine:/BiO/Project/AutoMSA/ProjectSeq_102_Validation_20180223/B1710
C      0      70      97.1      *      *      *      *      PKJJ01000001.1
C      1      1      *      *      *      *      *      PNGN01000013.1
```

(B)

```
junskim@cytosine:/BiO/Project/AutoMSA/ProjectSeq_102_Validation_20180223/B171025C
>1|*|FR775916.1|-|hsp60|1_607|1|Lactobacillus_jensenii_partial_hsp60_gene_for_hea
>2|*|FR775912.1|-|hsp60|1_604|1|Lactobacillus_crispatus_partial_hsp60_gene_for_he
junskim@cytosine:/BiO/Project/AutoMSA/ProjectSeq_102_Validation_20180223/B171025C
C      0      7      98.5      *      *      *      *      FR775916.1|-|hsp6
C      1      5      97.3      *      *      *      *      FR775912.1|-|hsp6
```

(C)

```
junskim@cytosine:/BiO/Project/AutoMSA/ProjectSeq_102_Validation_20180223/B1710
>1|*|GL379581.1|-|rpoa|137567_138585|-1|Lactobacillus_gasseri_JV-V03_genomic_s
junskim@cytosine:/BiO/Project/AutoMSA/ProjectSeq_102_Validation_20180223/B1710
C      0      12      99.4      *      *      *      *      GL379581.1|-|r
```

(D)

```
junskim@cytosine:/BiO/Project/AutoMSA/ProjectSeq_102_Validation_20180223/B1710
>1|*|AF247189.1|-|phr1|263_1909|1|Candida_albicans_Phr1p_(PHR1)_gene_PHR1-1_al
junskim@cytosine:/BiO/Project/AutoMSA/ProjectSeq_102_Validation_20180223/B1710
C      0      8      98.8      *      *      *      *      AF247189.1|-|p
```

(E)

```
junskim@cytosine:/BiO/Project/AutoMSA/ProjectSeq_102_Validation_20180223/B1710258001
>1|*|FWDN01000041.1|-|40s_ribosomal_protein_s8|87832_89209|-1|[Candida]_glabrata_iso
junskim@cytosine:/BiO/Project/AutoMSA/ProjectSeq_102_Validation_20180223/B1710258001
C      0      10      99.9      *      *      *      *      FWDN01000041.1|-|40s
```

FIG. 7

Figure 8:
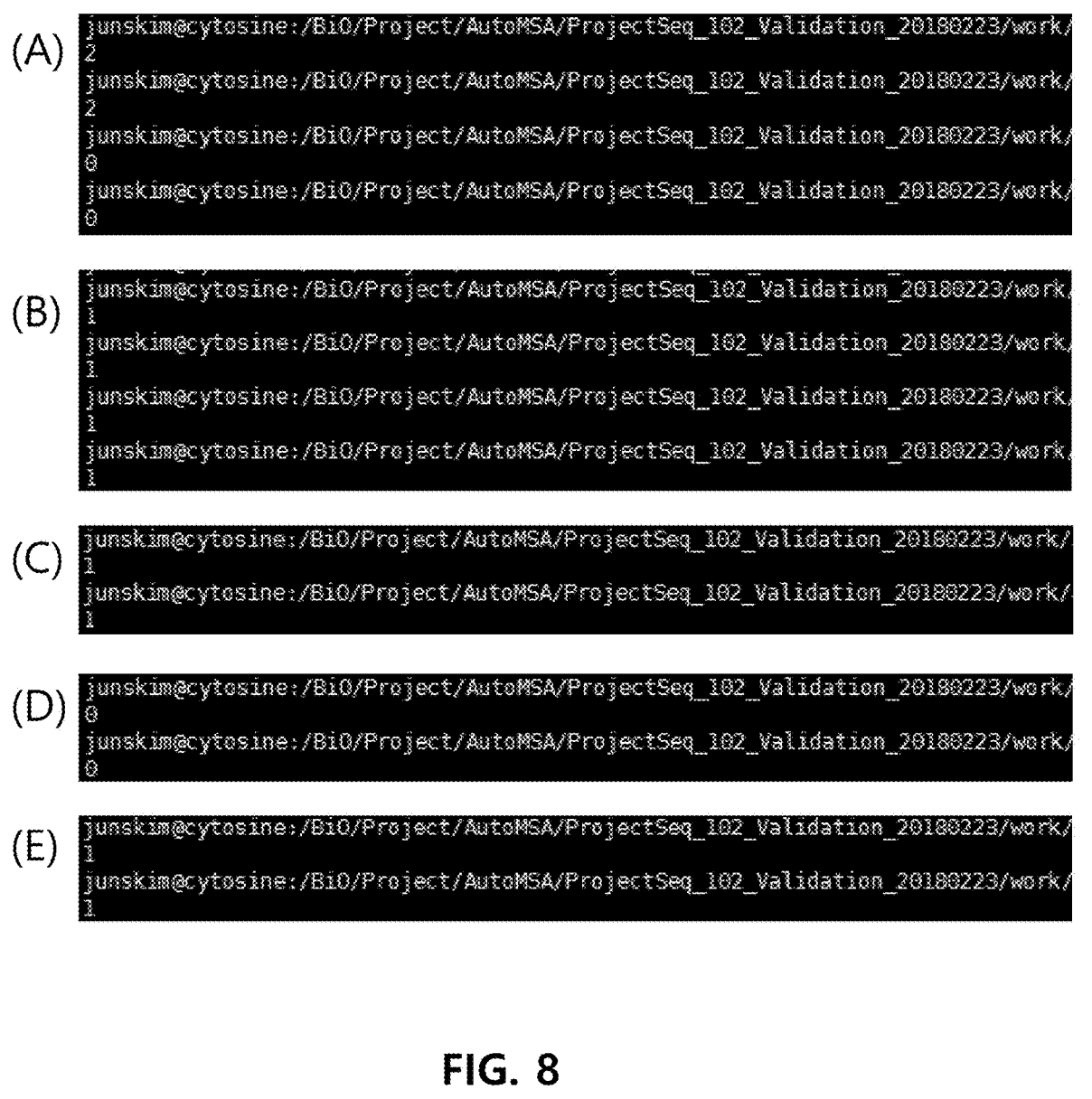

(A)
```
junskim@cytosine:/BiO/Project/AutoMSA/ProjectSeq_102_Validation_20180223/work/
2
junskim@cytosine:/BiO/Project/AutoMSA/ProjectSeq_102_Validation_20180223/work/
2
junskim@cytosine:/BiO/Project/AutoMSA/ProjectSeq_102_Validation_20180223/work/
0
junskim@cytosine:/BiO/Project/AutoMSA/ProjectSeq_102_Validation_20180223/work/
0
```

(B)
```
junskim@cytosine:/BiO/Project/AutoMSA/ProjectSeq_102_Validation_20180223/work/
1
junskim@cytosine:/BiO/Project/AutoMSA/ProjectSeq_102_Validation_20180223/work/
1
junskim@cytosine:/BiO/Project/AutoMSA/ProjectSeq_102_Validation_20180223/work/
1
junskim@cytosine:/BiO/Project/AutoMSA/ProjectSeq_102_Validation_20180223/work/
1
```

(C)
```
junskim@cytosine:/BiO/Project/AutoMSA/ProjectSeq_102_Validation_20180223/work/
1
junskim@cytosine:/BiO/Project/AutoMSA/ProjectSeq_102_Validation_20180223/work/
1
```

(D)
```
junskim@cytosine:/BiO/Project/AutoMSA/ProjectSeq_102_Validation_20180223/work/
0
junskim@cytosine:/BiO/Project/AutoMSA/ProjectSeq_102_Validation_20180223/work/
0
```

(E)
```
junskim@cytosine:/BiO/Project/AutoMSA/ProjectSeq_102_Validation_20180223/work/
1
junskim@cytosine:/BiO/Project/AutoMSA/ProjectSeq_102_Validation_20180223/work/
1
```

Retrieving, from the second database,
nucleic acid sequence data
having homology with the representative sequence
at a predefined homology value or greater

~S310

Selecting at least one nucleic acid sequence
data of a source organism not included in
the source organism of interest

~S320

Providing an exclusive nucleic acid sequence
data set

~S330

<u>300</u>

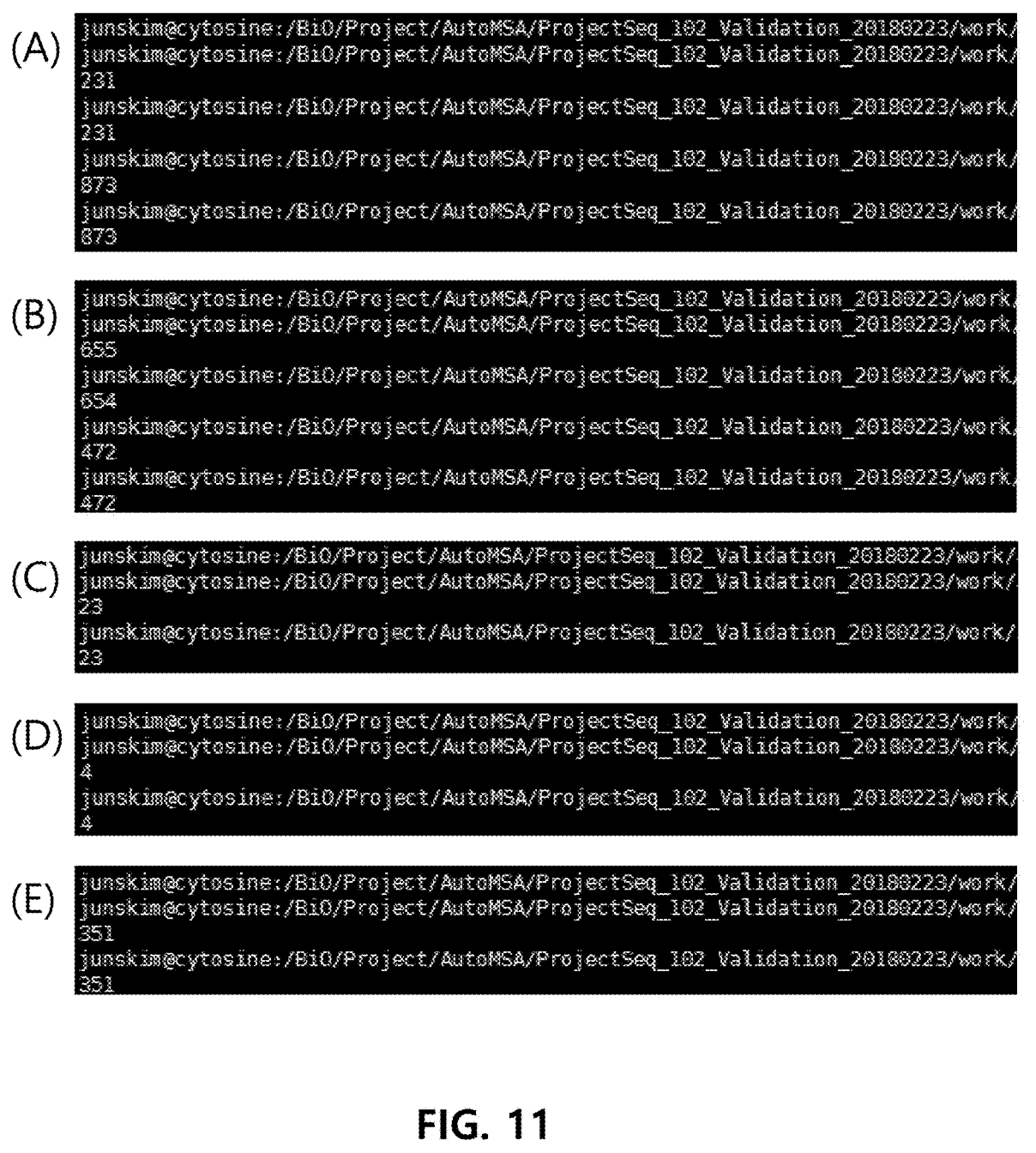

(A)
```
junskim@cytosine:/BiO/Project/AutoMSA/ProjectSeq_102_Validation_20180223/work/
junskim@cytosine:/BiO/Project/AutoMSA/ProjectSeq_102_Validation_20180223/work/
231
junskim@cytosine:/BiO/Project/AutoMSA/ProjectSeq_102_Validation_20180223/work/
231
junskim@cytosine:/BiO/Project/AutoMSA/ProjectSeq_102_Validation_20180223/work/
873
junskim@cytosine:/BiO/Project/AutoMSA/ProjectSeq_102_Validation_20180223/work/
873
```

(B)
```
junskim@cytosine:/BiO/Project/AutoMSA/ProjectSeq_102_Validation_20180223/work
junskim@cytosine:/BiO/Project/AutoMSA/ProjectSeq_102_Validation_20180223/work
655
junskim@cytosine:/BiO/Project/AutoMSA/ProjectSeq_102_Validation_20180223/work
654
junskim@cytosine:/BiO/Project/AutoMSA/ProjectSeq_102_Validation_20180223/work
472
junskim@cytosine:/BiO/Project/AutoMSA/ProjectSeq_102_Validation_20180223/work
472
```

(C)
```
junskim@cytosine:/BiO/Project/AutoMSA/ProjectSeq_102_Validation_20180223/work/
junskim@cytosine:/BiO/Project/AutoMSA/ProjectSeq_102_Validation_20180223/work/
23
junskim@cytosine:/BiO/Project/AutoMSA/ProjectSeq_102_Validation_20180223/work/
23
```

(D)
```
junskim@cytosine:/BiO/Project/AutoMSA/ProjectSeq_102_Validation_20180223/work/
junskim@cytosine:/BiO/Project/AutoMSA/ProjectSeq_102_Validation_20180223/work/
4
junskim@cytosine:/BiO/Project/AutoMSA/ProjectSeq_102_Validation_20180223/work/
4
```

(E)
```
junskim@cytosine:/BiO/Project/AutoMSA/ProjectSeq_102_Validation_20180223/work/
junskim@cytosine:/BiO/Project/AutoMSA/ProjectSeq_102_Validation_20180223/work/
351
junskim@cytosine:/BiO/Project/AutoMSA/ProjectSeq_102_Validation_20180223/work/
351
```

FIG. 11

METHOD FOR PROVIDING TARGET NUCLEIC ACID SEQUENCE DATA SET OF TARGET NUCLEIC ACID MOLECULE

CROSS-REFERENCE TO RELATED APPLICATIONS

This application is a national phase application of PCT Application No. PCT/KR2019/005227, filed on Apr. 30, 2019, which claims priority to Korean Patent Application No. 10-2018-0050035, filed on Apr. 30, 2018. The entire disclosures of the applications identified in this paragraph are incorporated herein by references.

SEQUENCE LISTING

This application contains references to amino acid sequences and/or nucleic acid sequences which have been submitted concurrently herewith as the sequence listing XML file entitled "000232usnp_SequenceLisiting_ST25.TXT", file size 44,919 bytes, created on 20 Jan. 2025. The aforementioned sequence listing is hereby incorporated by reference in its entirety pursuant to 37 C.F.R. § 1.52(e)(5).

FIELD OF THE INVENTION

The present invention relates to a method for providing a target nucleic acid sequence data set of a target nucleic acid molecule, and to a computer-readable storage medium and device for carrying out the method.

BACKGROUND OF THE INVENTION

A 21st century healthcare paradigm has been transformed from an era of public health through an era of disease treatment to an era of health lifespan extension via disease prevention and management. A demand for in vitro diagnostics (IVD) is increasing with a global trend changing from a therapeutic medicine to a preventive medicine. A global population aging and emergence of new viruses are another factor in the growth of the IVD market. In addition, due to a trend of treatment of patients toward personalized therapy, a scope in which the in vitro diagnosis is performed prior to determining the prescription or treatment of the patient is expanding.

Molecular diagnosis is the fastest growing segment of the IVD industry and is key to patient care continuity. Compared to other diagnosis platforms where disease portfolios overlap, the molecular diagnosis has advantages of excellent test precision, miniaturization, and fast processing time. Thanks to the strength of this molecular diagnostic technology, general diagnostic items which have been carried out by chemical and immunological tests in the past have been gradually replaced with the items of molecular diagnostic tests due to the recent development of molecule genetic technology. Typical techniques used in molecular diagnostics include polymerase chain reaction (PCR), Next-Generation Sequencing (NGS), microarray, and fluorescent in situ hybridization.

The most commonly used nucleic acid amplification method known as polymerase chain reaction (hereinafter referred to as PCR) includes repeated cycles of denaturation of double stranded DNA, annealing of oligonucleotide primers into DNA template, and primer extension by DNA polymerase (Mullis et. al, U.S. Pat. Nos. 4,683,195, 4,683, 202 and 4,800,159; Saiki et. al, (1985) Science 230, 1350 to 1354).

The PCR-based technology is widely used not only for the amplification of target DNA sequences but also for scientific applications or methods in biology and medical research. For example, detection of a target sequence, reverse transcriptase PCR (RT-PCR), differential display PCR (DD-PCR), cloning of known or unknown genes using PCR, rapid amplification of cDNA ends (RACE), arbitrary priming PCR (AP-PCR), multiplex PCR, SNP genomic typing, and PCR-based genomic analysis are available (McPherson and Moller, (2000) PCR. BIOS Scientific Publishers, Oxford).

These molecular diagnostic techniques analyze pathogen or risk factors for disease by evaluating the presence or sequence of the target nucleic acid molecule in the sample. In most cases, the target nucleic acid molecule sequence is selectively amplified for analysis. In order to carry out this molecular diagnosis, a design of the oligonucleotide used for the amplification and detection of the target nucleic acid molecule is important.

The oligonucleotide (probe and/or primer) used for detection of the target nucleic acid molecule should have appropriate specificity and detection level. Further, the oligonucleotide shall comply with a specific detection method and conditions set by the analyst. Therefore, the design of the oligonucleotide suitable for analytical purpose is very important.

Most target nucleic acid sequences of genes of higher animals such as humans and mammals to those of various bacteria and viruses classified as pathogens include sequence variations among individuals. In particular, RNA viruses are known to have high sequence variability (genetic diversity). More sophisticated oligonucleotide designs are required to detect target nucleic acid molecules with high genetic diversity with an appropriate coverage.

There have been various attempts to design oligonucleotides to detect target nucleic acid molecules with genetic diversity. A common method of designing such oligonucleotides is to find out conserved regions from multiple target nucleic acid molecules with genetic diversity and to design the oligonucleotide to be hybridized with these conserved regions (Wang, D et al., *Proc. Nat/Acad. Sci. USA,* 99:15687-15692(2002)).

For the design of oligonucleotides for the conserved regions, it is necessary to retrieve target nucleic acid sequences containing many sequence variants that are classified as the same species. Conventional methods disclose a new approach for processing more target nucleic acid sequence data of a target nucleic acid molecule and finding conserved regions using this process. However, no methodological progress has been made in the retrieval and processing of homologous sequences provided for the design of oligonucleotides. Further, the retrieval and processing still rely on the personal knowledge and experience of the researchers retrieving the sequences.

With this manual based sequence retrieval, the specificity of the designed oligonucleotide to the target nucleic acid sequence, and the coverage of the target nucleic acid sequence detectable by the oligonucleotide may be limited by the researcher's capabilities. Further, the manual sequence retrieval results in an increase in development time.

To solve this problem, it is necessary to develop an automated new method for efficiently retrieving target nucleic acid sequence data of a target nucleic acid molecule.

Throughout this specification, a number of citations and patent documents are referred to and cited. The disclosures of the cited documents and patents are incorporated herein by reference in their entirety to more clearly describe a prior art of the art related to the present invention and content of the present invention.

SUMMARY OF THE INVENTION

The present inventors have sought to develop an automated new method implemented in a computer that can effectively provide a target nucleic acid sequence data set for use in oligonucleotide design used for target nucleic acid molecule detection. As a result, the present inventors specify a name of the target nucleic acid molecule, and a source organism thereof, and automatically retrieve synonyms of the target nucleic acid molecule of the source organism from database, and retrieve a plurality of target nucleic acid sequence data of the target nucleic acid molecule using the synonyms, thereby effectively providing target nucleic acid sequence data of the target nucleic acid molecule. Further, the method selects representative sequences, which may reflect all variants of the retrieved target nucleic acid sequence among a large number of target nucleic acid sequence data and provide an additional target nucleic acid sequence data set of the target nucleic acid molecules using the representative sequences.

Thus, a purpose of the present invention is to provide a computer-implemented method for providing a target nucleic acid sequence data set of a target nucleic acid molecule of a source organism of interest.

Another purpose of the present invention is to provide a computer-readable storage medium containing instructions stored therein, in which when the instructions is executed by a computer, the instructions are configured to enable a processor of the computer to perform a method for providing a target nucleic acid sequence data set of a target nucleic acid molecule of a source organism of interest.

Still another purpose of the present invention is to provide a device for providing a target nucleic acid sequence data set of a target nucleic acid molecule of a source organism of interest, in which the device includes a computer processor and the computer-readable storage medium coupled to the computer processor.

Still another purpose of the present invention is to provide a computer program stored in a computer-readable storage medium, in which when the program is executed by a computer, the program is configured to enable a processor of the computer to perform a method for providing a target nucleic acid sequence data set of a target nucleic acid molecule of a source organism of interest.

Still yet another purpose of the present invention is to provide a computer-implemented method for providing an exclusive nucleic acid sequence data set of a target nucleic acid molecule of a source organism of interest.

Still yet another purpose of the present invention is to provide oligonucleotide sequence data for detecting a target nucleic acid molecule of a source organism of interest, in which the oligonucleotide sequence data is designed using the target nucleic acid sequence data set of the target nucleic acid molecule of the source organism of interest provided by the method as defined above.

Still yet another purpose of the present invention is to provide oligonucleotide sequence data for detecting a target nucleic acid molecule of a source organism of interest, in which the oligonucleotide sequence data is designed using the exclusive nucleic acid sequence data set of the target nucleic acid molecule of the source organism of interest provided by the method as defined above.

Still yet another purpose of the present invention is to provide a method for providing an oligonucleotide for detecting a target nucleic acid molecule of a source organism of interest, in which the method uses the target and/or exclusive nucleic acid sequence data set of the target nucleic acid molecule of the source organism of interest provided by the methods as defined above.

Other purposes and advantages of the present invention will become more apparent from the following embodiments, claims and drawings. In describing the components of the present invention, the terms first, second, A, B, (a), (b), etc. may be used. These terms are intended to distinguish a constituent element from other constituent elements, and the terms do not limit the nature, order or arrangement of the corresponding constituent elements.

BRIEF DESCRIPTION OF THE DRAWINGS

FIG. 1 is a flow chart showing the process of providing the target nucleic acid sequence data set according to the method of the present invention.

FIG. 3 shows display of the retrieved synonym after performing the synonym retrieval step for each target in the AutoMSA system.

FIG. 4 shows the result of recognition of tuf gene portion and retrieval of corresponding sequences from a single nucleic acid record (*Gardnerella vaginalis* 41V GV41V_c00024, whole genome shotgun sequence) searched using information on the tuf gene of *Gardnerella vaginalis* (txid: 2702). FIG. 4A and FIG. 4B capture information about the tuf gene of *Gardnerella vaginalis* (txid: 2702) stored in the nucleotide database of NCBI (SEQ ID NO: 1). FIG. 4C shows the display of the retrieved sequence after parsing step in AutoMSA system in which the method of the present invention is implemented (SEQ ID NO: 2).

FIG. 7 shows the result of displaying the selected representative sequence after selecting the representative sequence for each target in the AutoMSA system. A [>] mark is present on the line that displays information about the representative sequence.

FIG. 8 shows the display of the number of retrieved second target nucleic acid sequence data after performing the second target nucleic acid sequence data retrieval step using the representative sequence in the AutoMSA system.

FIG. 11 shows a display of the number of selected essential exclusive nucleic acid sequence data after selecting the essential exclusive nucleic acid sequence data for each target in the AutoMSA system.

DETAILED DESCRIPTION OF THIS INVENTION

Figure 2:
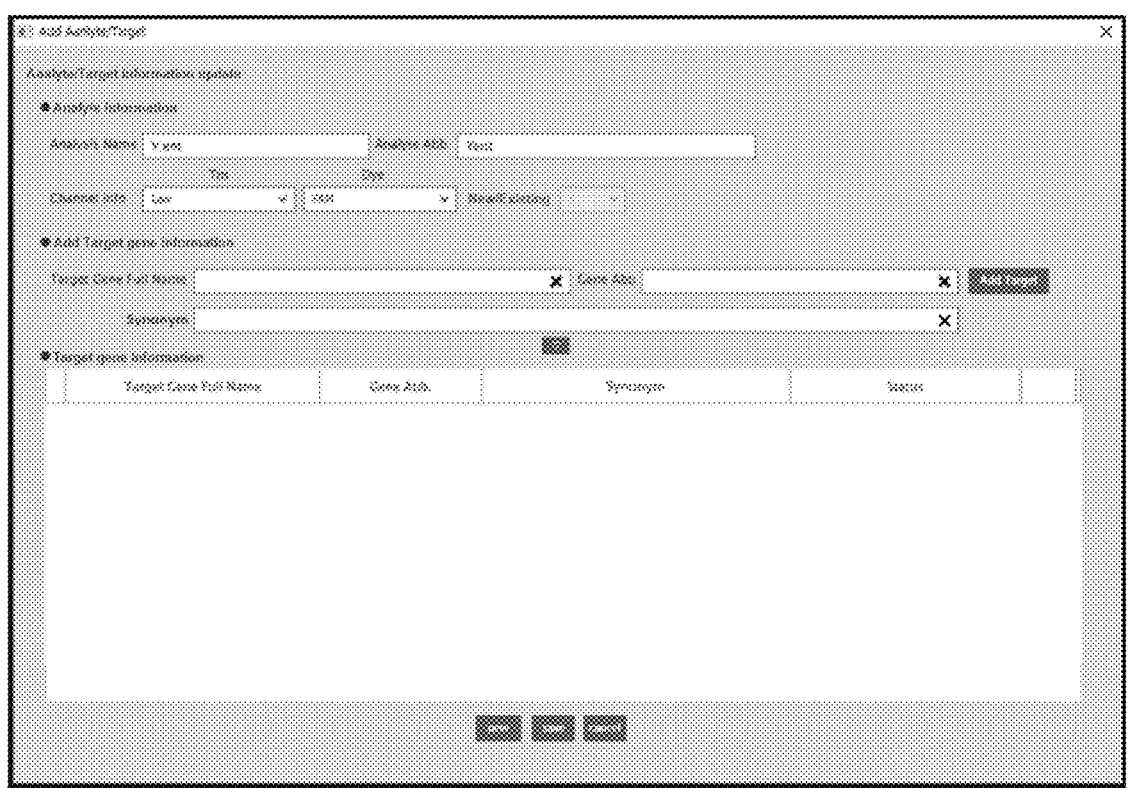
FIG. 2 shows the information input interface of the AutoMSA system that the method of the present invention is implemented.

I. Target Nucleic Acid Sequence Data Set Providing Method Using Automatic Retrieval of Synonyms According to one aspect of the present invention, the present invention provides a computer-implemented method for providing a target nucleic acid sequence data set of a target nucleic acid molecule of a source organism of interest, the method comprising:

(a) receiving a name of the nucleic acid molecule and a name of the source organism, and automatically retrieving synonyms for the target nucleic acid molecule of the source organism from a first database;

(b) retrieving identifiers of nucleic acid records from a second database, wherein each of the nucleic acid records is associated with the source organism and comprises, as a descriptor thereof, at least one selected from the group of the name of the target nucleic acid molecule and the retrieved synonyms; and (c) retrieving nucleic acid sequence data specified by the identifiers to provide a target nucleic acid sequence data set of the target nucleic acid molecule.

The present inventors have sought to develop an automated new method implemented in a computer that can effectively provide a target nucleic acid sequence data set for use in oligonucleotide design used for target nucleic acid molecule detection. As a result, the present inventors receive a name of the target nucleic acid molecule, and a name of source organism, and automatically retrieve synonyms of the target nucleic acid molecule of the source organism from database, and retrieve a plurality of target nucleic acid sequence data of the target nucleic acid molecule using the synonyms, thereby effectively providing target nucleic acid sequence data set of the target nucleic acid molecule. Further, the method selects representative sequences, which may reflect all variants of the retrieved target nucleic acid sequence among a large number of retrieved target nucleic acid sequence data, and provide an additional nucleic acid sequence data set of the target nucleic acid molecules using the representative sequences.

FIG. 1 is a schematic diagram of the target nucleic acid sequence data set providing method of the present invention. A detailed description of the method on a step basis is as follows:

Step (a): Retrieving of Synonyms

According to the present invention, the step (a) includes receiving a name of the nucleic acid molecule and a name of the source organism, and automatically retrieving synonyms for the target nucleic acid molecule of the source organism from a first database.

As used herein, the term "target nucleic acid molecule" or "target nucleic acid" means nucleic acid as a chemical material to be finally detected. The target nucleic acid molecule includes not only double strand but also single strand. The target nucleic acid molecule may include a target nucleic acid molecule initially present in the sample to be analyzed, and a nucleic acid molecule newly generated in the reaction process.

As used herein, the target nucleic acid molecule may be an entire nucleic acid molecule or a partial region of a nucleic acid molecule to be detected. Further, as used herein, the target nucleic acid molecule may mean one functional unit of a nucleic acid molecule. The functional unit may be gene. The gene is a physical or functional unit of genetic information consisting of DNA or RNA. The gene includes both regions encoding proteins and regions that do not encode proteins. As used herein, the term "target gene" may be used interchangeably with the target nucleic acid molecule when the target nucleic acid molecule is a gene part that is one functional unit in a physical nucleic acid molecule.

As used herein, the term "detection" refers to a measurement that provides a qualitative or quantitative indication of the presence or absence of a target nucleic acid molecule. The detection includes identification, determination or analysis.

The target nucleic acid molecules include, for example, prokaryotic nucleic acid, eukaryotic cells (e. g., protozoa and parasites, fungi, yeast, higher plants, lower animals, and higher animals, including mammals and humans) nucleic acids, viruses (e.g., herpes viruses, HIV, influenza viruses, Epstein-Barr virus, hepatitis virus, poliovirus, etc.) nucleic acid or viroid nucleic acid. The target nucleic acid molecule includes not only naturally occurring nucleic acid molecule but also an artificial nucleic acid molecule. The target nucleic acid molecule may include sequence-known or unknown molecules. The nucleic acid molecule may be naturally induced, recombinantly produced, or chemically synthesized.

In the method of the present invention, the target nucleic acid molecule may be defined very specifically, as defined using a specific nucleic acid sequence. In this case, an oligonucleotide for detecting the target nucleic acid molecule may be designed using only the data of the defined specific nucleic acid sequence.

In one example, according to the present invention, the target nucleic acid molecule may be conceptually defined, for example, using a common specific gene possessed by a specific organism group. In this case, the nucleic acid sequence of a nucleic acid molecule of each entity belonging to a specific organism group may differ partially from the nucleic acid sequence of the target nucleic acid molecule, which is defined using the common specific gene. Therefore, in order to design an oligonucleotide to detect the common target nucleic acid molecule to identify the presence of a specific organism group (for example, microorganism of a specific species), a plurality of target nucleic acid sequence data may be required, which may be partially different from each other.

The designed oligonucleotide may have broader detection coverage for the specific organism group, when the more various target nucleic acid sequence data of the common target nucleic acid molecule of the specific organism group is retrieved, and the oligonucleotide for detecting the common target nucleic acid molecule using the more various target nucleic acid sequence data.

As used herein, to retrieve sequence data or information is to find and collect sequence data or information stored in a computer or a digital information storage medium. The terms "retrieve" and "collect" may be used interchangeably with each other.

As used herein, the term "sequence" refers to the specific order of the monomers in the macromolecule. As used herein, the term "nucleic acid sequence" or "nucleic acid sequence data" refers to the order of nucleotides in a nucleic acid molecule or information about the order of nucleotides in a nucleic acid molecule. These may be used interchangeably with each other.

As used herein, the target nucleic acid sequence refers to a sequence related to the target nucleic acid molecule, which is the nucleic acid molecule to be finally detected. The target nucleic acid sequence may include the entire nucleic acid sequence corresponding to the target nucleic acid molecule, or a partial region of the entire nucleic acid sequence.

The nucleic acid sequences of the common specific gene possessed by the specific organism group may be the same or different between entities. Thus, when the target nucleic acid molecule is defined using a common specific gene possessed by a specific organism group, the nucleic acid sequence corresponding to the target nucleic acid molecule may not be determined by one order of nucleotides. Therefore, in other words, one target nucleic acid molecule may have various target nucleic acid sequence data whose orders of nucleotides are different from each other.

The target nucleic acid sequence data set refers to a collection of target nucleic acid sequence data. In other words, the target nucleic acid sequence data set refers to a collection of information about the order of the nucleotides of the target nucleic acid molecule. As described in the above description, one target nucleic acid molecule may have various target nucleic acid sequence data whose orders of nucleotides of the nucleic acid molecule are different from each other. Thus, according to one embodiment of the present invention, the target nucleic acid sequence data set of the target nucleic acid molecule may be a data set including a plurality of target nucleic acid sequence data. According to one embodiment of the present invention, the target nucleic acid sequence data set comprises nucleic acid sequence data corresponding to a portion or entirety of the target nucleic acid molecule or nucleic acid variant sequence data of the target nucleic acid molecule. The nucleic acid variant sequence of the target nucleic acid molecule refers to a nucleic acid sequence that contains a nucleotide sequence in which at least one nucleotide is substituted, deleted and/or added compared to the target nucleic acid sequence of the target nucleic acid molecule. The nucleic acid sequence data corresponding to the target nucleic acid molecule means the nucleic acid sequence data consisting of the nucleic acid sequence of the target nucleic acid molecule. The target nucleic acid sequence data of the target nucleic acid molecule refers to the nucleic acid sequence data related to the nucleic acid sequence of the target nucleic acid molecule of the source organism of interest. The target nucleic acid sequence data of the target nucleic acid molecule includes both of nucleic acid sequence data consisting of the entirety or portion of the nucleic acid sequence corresponding to the target nucleic acid molecule of the source organism of interest, and nucleic acid sequence data including the entirety or portion of the nucleic acid sequence corresponding to the target nucleic acid molecule of source organism of interest.

A name of the target nucleic acid molecule refers to a word or symbol that identifies the target nucleic acid molecule. According to the present invention, the name of the target nucleic acid molecule may be the name of the gene (target gene) that the target nucleic acid molecule contains. The name includes an official full name and a common name. The common name refers to the name used in identification of the target nucleic acid molecule in the technical field of the present invention other than the official full name. According to the present invention, a symbol refers to a mark, a sign, a letter or a combination of letters to represent a target nucleic acid molecule. The symbol refers to the official symbol and alias. The alias refers to the unofficial symbol used in the identification of the target nucleic acid molecule in the technical field of the present invention other than the official symbol.

The source organism refers to an organism that contains a target nucleic acid molecule. The organism includes, for example, prokaryotes, eukaryotic cells (e.g., protozoa and parasites, fungi, yeast, higher plants, lower animals and higher animals including mammals and humans), virus (e.g., herpes virus, HIV, influenza virus, Epstein-Barr virus, hepatitis virus, poliovirus, etc.) or viroid.

The source organism may include an organism belonging to a biological classification system, such as, a domain, a kingdom, a division, a class, an order, a family, a genus, a species, a subspecies, a varieties, a variant, a subtype, a genotype, a serotype, a strain, an isolate or a cultivar.

Receiving the name of the target nucleic acid molecule and the name of the source organism means receiving (or inputting to a computer) the word or symbol that identifies the target nucleic acid molecule and the name of an organism that contains the target nucleic acid molecule. Upon the reception of the names, the nucleic acid molecule whose a plurality of target nucleic acid sequence data will be provided by the method of the present invention may be determined. A scheme of receiving the name or symbol of the target nucleic acid molecule or the name of the organism in which the target nucleic acid molecule is included is not particularly limited. For example, the name or symbol may be provided by the user inputting directly the name or symbol through an input device. Alternatively, the name or symbol may be provided through various data storage media. Alternatively, the name or symbol of the target nucleic acid molecule or the name of the organism that contains the target nucleic acid molecule may be provided via wired and wireless data transmission.

Synonym Retrieval

The method retrieves the synonym of the target nucleic acid molecule of the source organism based on the name of source organism and the name of the target nucleic acid molecule as received.

The method of the present invention retrieves and arranges as many target nucleic acid sequence data as possible so that the oligonucleotide designed using the data may have a broad coverage of the target nucleic acid molecule. Therefore, firstly, it is necessary to retrieve as many target nucleic acid sequence data as possible. To do this, the method retrieves the synonym of the target nucleic acid molecule to be used for target nucleic acid sequence data retrieval.

As used herein, the term "the synonym of the target nucleic acid molecule" refers to a word group that has the same meaning as a name or symbol that identifies or indicates a target nucleic acid molecule. According to the present invention, the synonym of a target nucleic acid molecule refers to a word group that includes both a name and a symbol that may identify a target nucleic acid molecule and may include all of the official full name, the common name, the official symbol, and the alias.

The synonym of the target nucleic acid molecule may be retrieved from the database. The database refers to a collection of organized data. The database may be a collection of organized data that may be stored and accessed through the computer system. In this application, the database from which the synonym is retrieved is called the first database to distinguish it from the other databases.

According to one embodiment of the present invention, the first database from which the synonym of the target nucleic acid molecule may be retrieved may be the gene database.

The gene database refers to a database that collects, classifies and stores information about the genes that the organism contains. The gene database may include names, symbols and source organism names of genes, descriptions of the genes, information about the nucleic acid sequence of the gene (for example, nucleic acid sequence identifier) and information about the protein that the nucleic acid molecule encodes (for example, protein name, protein identifier). The gene database may be named as the database for providing genetic information about the organism. The terms "gene database" and "database for providing genetic information about the organism" may be used interchangeably with each other.

According to one embodiment of the present invention, the first database is configured to provide genetic information of an organism including a title of a nucleic acid molecule, a name of a nucleic acid molecule, description of a nucleic acid molecule, a source organism name, and a name of a protein encoded by a nucleic acid molecule. The title refers to information described as a title of the record when the first database provides the user with a record of information of one nucleic acid molecule.

The first database may be a directly constructed database or a user restricted private gene database. Alternatively, the first database may be public database. The first public database includes not only those run by national or public agencies, but also those created by corporations, educational institutions, and research institutes. According to one embodiment of the present invention, the first database may be a publicly accessible gene database selected from the group consisting of GenBank, EMBL and DDBJ.

According to one embodiment of the present invention, the first database may be a publicly accessible database that includes the name of the target nucleic acid molecule and source organism information thereof.

According to the present invention, the synonym of the target nucleic acid molecule is automatically retrieved from the first database.

For example, a registrant who registers a sequence of a nucleic acid molecule in the nucleotide database should fill the official full name or official symbol in the field for the gene name of the nucleic acid molecule. However, in some cases, the official full name of the nucleic acid molecule may be filled in another field, and other synonyms of the nucleic acid molecule may be entered in the field for the gene name. Alternatively, the name of the target nucleic acid molecule input to perform the method of the present invention may not be the actual official full name or official symbol of the target nucleic acid molecule but one of the other synonyms thereof. Therefore, it is necessary to acquire as many synonyms as possible for use in search in order to secure the nucleic acid sequence data of the nucleic acid molecule.

Thus, (i) the method should obtain as many gene information summary records as possible related to the names of the source organism and target nucleic acid molecule as input. Next, (ii) the method should effectively obtain a synonym from the obtained gene information summary records.

First, to ensure sufficient gene information summary records, among the various input fields of the gene information summary record of the nucleic acid molecule, the top fields with high frequency at which the official full name or the official symbol of the nucleic acid molecule was input thereto, were analyzed. As a result, in the gene database, the fields corresponding to the gene name of the nucleic acid molecule, and the fields corresponding to the name of the protein which is produced when the nucleic acid molecule is expressed were confirmed as the fields with a high frequency at which the official full name or official symbol of the nucleic acid molecule was input thereto. Specifically, it is understood that the most effective search scheme for retrieving the gene information summary record of the target nucleic acid molecule is to perform search with the received name of source organism as a search term in the source organism field and the received name of the target nucleic acid molecule as a search term in the gene name field, title field and protein name field.

Second, in order to obtain a synonym from the acquired gene information summary record efficiently, the method analyzed the frequency with which names or symbols of the target nucleic acid molecule other than the official full name or official symbol is recorded in each field of the gene information summary record. As a result, it was found that the description field corresponding to the name of protein and the field corresponding to the gene name of the nucleic acid molecule are the fields at which names or symbols other than the official full name or official symbol of the target nucleic acid molecule are input most frequently.

Therefore, it was evaluated that retrieving the information described in the gene name field and the description field of gene in the retrieved gene information summary record is the most effective scheme.

According to one embodiment of the present invention, the step (a) may comprises: (a1) receiving a name of the nucleic acid molecule and a name of the source organism, and retrieving, from the first database, a gene information summary record which is associated with the source organism; wherein the received name of the target nucleic acid molecule is filled in a title, gene or protein field of the gene information summary record; and (a2) retrieving the synonyms of the target nucleic acid molecule by retrieving information filled in name, symbol and description fields in the gene information summary record.

The gene information summary record is a compilation unit of information about a specific gene. According to one embodiment of the present invention, the gene information summary record is a compilation unit of information about a specific gene that contains a gene name, a protein name and description information about a gene. The gene information summary record is also called "gene information report" or "gene report". The terms "gene information summary record", "gene information report" and "gene report" may be used interchangeably.

According to one embodiment of the present invention, the synonym retrieval step (a) may retrieve the synonyms by a processor of the computer communicating with the first database via a wired or wireless network, based on the received name of the target nucleic acid molecule and the received information about the source organism thereof.

The received name of the target nucleic acid molecule and the received information about the source organism thereof may be received from the user directly inputting the name of the target nucleic acid molecule and the information about the source organism thereof or may be received in a form of a file.

In one embodiment of the present invention, the synonym retrieval step (a) may comprise: transmitting, by the processor, instructions to the first database, in which the instructions causes the first database to transmit a gene information summary record to a memory of the computer; wherein the gene information summary record is a record of the received source organism among gene records included in the first database and at least one of title, gene and protein fields of the gene information summary record is identical to the received name of the target nucleic acid molecule; receiving, by the processor, the gene information summary record sent from the first database in response to the instruction; and retrieving, by the processor, information filled in name, symbol and description fields of the received gene information summary record and, storing the information in the memory as the synonym.

The transmission and reception may be executed via a wired or wireless network.

In one embodiment of the present invention, the synonym retrieval step (a) may comprise: (i) transmitting, by the processor, instructions to the first database, in which the instructions causes the first database to transmit information recorded in name, symbol and description fields of a gene information summary record selected among gene record included in the first database to a memory of the computer, wherein the gene information summary record is a record associated with the received source organism and at least one of title, gene and protein fields of the gene information summary record is identical to the received name of the target nucleic acid molecule; (ii) retrieving, by the processor, the information recorded in the name, symbol and description fields in the gene information summary record sent from the first database in response to the instruction, and, (iii) storing the information in the memory as the synonym. The synonyms stored in the memory may be stored in a storage medium in a form of an electronic file.

Step (b): Retrieval of Identifiers of Target Nucleic Acid Sequence Data

Then, the method retrieves identifiers of target nucleic acid sequence data of the source organism using the retrieved synonyms and the information about the source organism. Specifically, the method retrieves identifiers of nucleic acid sequence data from a second database, wherein the nucleic acid sequence data is associated with the source organism and comprises, as a descriptor thereof, at least one selected from the group of the name of the target nucleic acid molecule and the retrieved synonyms. In step (b), identifiers of nucleic acid sequence data that is associated with the source organism and has, as a descriptor thereof, the name of the target nucleic acid molecule received in step (a) or one of the synonyms of the name of the target nucleic acid molecule received in step (a) is retrieved from the second database. The nucleic acid sequence data associated with the source organism refers to nucleic acid sequence data wherein a name or synonym of the received source organism in the step (a) or a name of or synonym of a source organism belonging to a subclass of the received source organism in terms of classification is recorded as a source organism of the nucleic acid sequence data.

The identifier of the present invention refers to data used to identify specific nucleic acid sequence data. The data used as the identifier is not limited to any particular format in terms of letters, numbers, or any combination thereof. Different identifiers for the same nucleic acid sequence data may be assigned between databases. Examples of the identifier may include an accession number or accession version commonly used in GenBank and EMBL, or a GI number used in GenBank.

As used herein, the descriptor refers to a field that describes or identifies specific nucleic acid sequence data. The descriptor may be metadata of specific nucleic acid sequence data. Specifically, the descriptor may include all fields of a record containing the specific nucleic acid sequence data. In one embodiment of the present invention, the descriptor may include name, definition, keywords, source organism, and reference-title.

The nucleic acid sequence data associated with the source organism and comprising, as a descriptor thereof, at least one selected from the group of the name of the target nucleic acid molecule and the retrieved synonyms may be the nucleic acid sequence data of the nucleic acid molecule specified by the descriptor and the source organism.

According to one embodiment of the present invention, the second database may be configured to provide a nucleic acid record containing nucleic acid sequence data, and an identifier and a descriptor about the nucleic acid sequence data.

The second database may refer to database that provides a nucleic acid record containing the nucleic acid sequence data and identifiers and descriptors about the nucleic acid sequence data. As used herein, the database that provides the nucleic acid record containing the nucleic acid sequence data and identifiers and descriptors about the nucleic acid sequence data may be referred to as the second database to distinguish it from other databases.

The second database may be called "nucleotide database", "nucleic acid sequence database", or "nucleic acid information collection". Thus, the second database may refer to database in which nucleic acid sequence data of various nucleic acid molecules are collected, classified and stored. The second database contains a nucleic acid record. The nucleic acid record may contain the nucleic acid sequence data of the nucleic acid molecule, and metadata of the nucleic acid sequence data as the descriptor of the nucleic acid molecule. The metadata of the nucleic acid sequence data refers to bibliographic information on the nucleic acid sequence data. This metadata may include, for example, an identifier of nucleic acid sequence data, information on organism including the corresponding nucleic acid molecule, keywords, information about references such as publications in which the nucleic acid sequence data is disclosed. The second database may be constructed directly or may be a user restricted private database. Alternatively, the second database may be public database. The public second database includes not only those run by national or public institutions, but also those created by corporations, educational institutions, and research institutes. The second database may be a for example, a nucleotide database of GenBank, or a database of DNA Data Bank of Japan (DDBJ) or EMBL. The nucleic acid record may also be named as "a nucleic acid report" or "a nucleic acid information report". The terms "nucleic acid record", "nucleic acid report" or "nucleic acid information report" may be used interchangeably.

According to the present invention, the first database and the second database may belong to the same organization. Alternatively, the first database and the second database may belong to different organizations.

According to one embodiment of the present invention, the step (b) may comprise: transmitting, by the processor, instructions to the second database, in which the instructions causes the second database to retrieve identifiers of nucleic acid sequence data from the second database, based on the target nucleic acid molecule name and its synonyms and to transmit identifiers of nucleic acid sequence data to a memory of the computer; wherein the nucleic acid sequence data is associated with the source organism and comprises, as a descriptor thereof, at least one selected from the group of the name of the target nucleic acid molecule and the retrieved synonyms and storing the transmitted identifiers to a memory of the computer.

According to one embodiment of the present invention, the step (b) may comprise: transmitting, by the processor, instructions to the second database, in which the instructions causes the second database to transmit, to a memory of the computer, identifiers of a nucleic acid record that meets following conditions (i) and (ii); and receiving, by the processor, the information sent from the second database in response to the instruction via a wired or wireless network and storing the information into the memory:

(i) a condition that the nucleic acid record is about the received source organism; and (ii) a condition that the nucleic acid record has the metadata indicating at least one selected from the group of the received name and the retrieved synonyms of the target nucleic acid molecule.

The retrieved identifiers in the memory may be stored in the storage media in a form of electronic files.

Step (c): Providing of Target Nucleic Acid Sequence Data Set

In the step (c), the method retrieves the nucleic acid sequence data specified by the identifiers and provides the target nucleic acid sequence data set of the target nucleic acid molecule.

The identifiers may be the identifiers retrieved in the step (b) and may be identifiers that represent the target nucleic acid sequence data of the target nucleic acid molecule. Therefore, the nucleic acid sequence data specified by the identifiers may be the target nucleic acid sequence data of the target nucleic acid molecule. By retrieving the nucleic acid sequence data, the target nucleic acid sequence data set is provided.

The providing of the target nucleic acid sequence data set may be performed by a known data providing scheme. For example, an output device or a display device may be used to expose content of the data to the user such that the user directly recognizes the data. Alternatively, the data may be provided to the user in such a way that the data is stored by a storing machine in a data storage medium intended by the user. Alternatively, the data may be provided by transmitting the data to a device intended by the user via a network device capable of wired or wireless data transmission.

The providing of the target nucleic acid sequence data set may be to provide an entirety of the nucleic acid sequence data specified by the identifiers or may be to provide a portion of the nucleic acid sequence data specified by the identifiers.

Retrieving the nucleic acid sequence data specified by the identifiers may be retrieval of the data from the second database using the identifiers. The retrieval of the nucleic acid sequence data may be retrieved via receiving the nucleic acid sequence data itself identified by the identifiers from the second database. Alternatively, the retrieval of the nucleic acid sequence data may include retrieving the nucleic acid record specified by the identifiers from the second database and extracting nucleic acid sequence data therefrom.

According to one embodiment of the present invention, the step (c) may comprise: transmitting, by the processor, instructions to the second database, in which the instructions causes the second database to transmit the nucleic acid sequence data corresponding to the identifiers; and receiving, by the processor, the nucleic acid sequence data sent from the second database in response to the instruction and storing the data in the memory, and providing the data as the target nucleic acid sequence data set of the target nucleic acid molecule.

Parsing

According to one embodiment of the present invention, the step (c) may comprise selectively retrieving nucleic acid sequence data corresponding to the target nucleic acid molecule from nucleic acid sequence data specified by the identifiers and providing the target nucleic acid sequence data set of the target nucleic acid molecule. The step (c) selectively may retrieve nucleic acid sequence data corresponding to the target nucleic acid molecule from nucleic acid sequence data specified by the identifiers and provide the retrieved target nucleic acid sequence data set of the target nucleic acid molecule.

The nucleic acid record retrieved by the identifier may contain only the nucleic acid sequence data corresponding the target gene as the target nucleic acid molecule. However, in many cases, not only the sequence of the target gene but also other nucleic acid sequence data may be included together in the nucleic acid record. Further, depending on the purpose of retrieving the target nucleic acid sequence data set of the target nucleic acid molecule, it may be necessary to retrieve only the nucleic acid sequence data corresponding a portion of the target nucleic acid molecule. Therefore, after retrieving an entirety or portion of the nucleic acid record specified by the identifiers, the method may selectively retrieve nucleic acid sequence data corresponding to a target nucleic acid molecule. In this connection, the step of recognizing, selecting and re-retrieving the necessary portion of the retrieved nucleic acid record is called "paring".

Specifically, according to one embodiment of the present invention, the step (c) may be characterized by including following sub-steps:

(c1) retrieving nucleic acid records specified by the identifiers; and (c2) retrieving nucleic acid sequence data corresponding to the target nucleic acid molecule from each of the nucleic acid records and providing the target nucleic acid sequence data set of the target nucleic acid molecule. The nucleic acid record contains the nucleic acid sequence data and the metadata of the nucleic acid sequence data as a descriptor.

According to one embodiment of the present invention, the step (c2) comprises selectively retrieving the nucleic acid sequence data and identification information about the nucleic acid sequence data from the nucleic acid records and providing the target nucleic acid sequence data set of the target nucleic acid molecule.

Selectively retrieving may refer to selectively retrieving only required nucleic acid sequence data from the nucleic acid sequence data in the nucleic acid record.

When the nucleic acid sequence data contained in the nucleic acid record include a plurality of distinguishable nucleic acid sequence data, the corresponding nucleic acid record includes a plurality of sub-records. A sub-record refers to a data group unit that contains nucleic acid sequence data that may be distinguished within a nucleic acid record and/or a specification thereof. Each sub-record contains location information on the nucleic acid sequence data corresponding to each sub-record and a specification containing a description of the nucleic acid sequence data corresponding to each sub-record.

When a nucleic acid record contains at least two nucleic acid sequences that may be recognized as being physically or functionally different, the distinguishable nucleic acid sequence data refers to each of the at least two nucleic acid sequences and a specification thereof. For example, when all of nucleic acid sequences of a plurality of genes encoding different proteins are included in one nucleic acid sequence data in the nucleic acid record, the nucleic acid sequence data may be divided into portions corresponding to genes.

In order to selectively retrieving target nucleic acid sequence data from one nucleic acid record containing a number of distinguishable nucleic acid sequence data, it may be determined whether the corresponding sub-record is a valid sub-record, based on the specification included in each sub-record in the nucleic acid record. The valid sub-record refers to a sub-record that contains the nucleic acid sequence data to be retrieved and/or location information on the nucleic acid sequence data to be retrieved.

The specification included in each sub-record refers to a field recorded with information on nucleic acid sequence data including the location information thereof. The specification may include, for example, a gene name represented by the corresponding sub-record, and information (e.g., protein name, identifier of protein) about a protein produced from the gene represented by the corresponding sub-record, record of nucleic acid record provider, amino acid sequence information, etc.

The present inventors have confirmed that the retrieved synonyms are recorded in some of the specifications of the sub-record, and the frequency and accuracy of the retrieved synonym are different between specifications. Therefore, we have confirmed that it is the most efficient scheme for obtaining nucleic acid sequence data to assign priority to some specification fields and to sequentially determine whether the retrieved synonym is recorded in the specification fields.

The present inventors compared a gene included in the nucleic acid sequence data indicated by each sub-record with data in specifications of the corresponding sub-record. From this comparison, the retrieved synonym is most frequently filled in the specification about the gene name, second-most frequently filled in the specification about protein information, and third-most frequently filled in the specification about the provider of nucleic acid record. Therefore, we evaluated whether the retrieved synonym is filled in the specifications in the above rank. Thus, the method determines the valid sub-record based on the evaluation. Then, the method retrieves the nucleic acid sequence data of the determined valid sub-record, and identification information thereof. This approach is the most efficient scheme to selectively obtain desired nucleic acid sequence data accurately.

Thus, according to one embodiment of the present invention, selectively retrieving the nucleic acid sequence data corresponding to the target nucleic acid molecule and identification information about the nucleic acid sequence data from each of the nucleic acid records may include following sub-steps:

(c21) determining a valid sub-record among at least one sub-record in each of the nucleic acid records, wherein the synonyms are recorded in a pre-defined first specification in the sub-record;

(c22) upon determination that is no valid sub-record determined by the first specification among the at least one sub-record in each of the nucleic acid records, determining a valid sub-record among the at least one sub-record in each of the nucleic acid records, wherein the synonyms are recorded in a pre-defined second specification in the sub-record;

(c23) upon determination that is no valid sub-record determined by the second specification among the at least one sub-record in each of the nucleic acid records, determining a valid sub-record among the at least one sub-record in each of the nucleic acid records, wherein the synonyms are recorded in a pre-defined third specification in the sub-record; and (c24) retrieving nucleic acid sequence data corresponding to the determined valid sub-record and identification information thereof.

According to one embodiment of the present invention, the first specification may be related to a gene name of a nucleic acid sequence in a sub-record. The second specification may be related to the protein information produced from the gene. The third specification may be related to a note of the genetic information provider.

Clustering

According to one embodiment of the present invention, when a plurality of nucleic acid sequence data is retrieved from one nucleic acid record in the step (c2), nucleic acid sequence data whose sequence data partially or entirely overlaps among the plurality of nucleic acid sequence data may be assembled and provided.

For example, the presence of the plurality of nucleic acid sequence data of one target nucleic acid molecule in one nucleic acid record corresponds to a case where each nucleic acid sequence data is a sequence of a portion of the target nucleic acid molecule. In other words, each of the plurality of nucleic acid sequence data does not independently encodes protein, but an entirety of the plurality of nucleic acid sequence data encodes one protein. In this case, it is not appropriate to use each of the plurality of nucleic acid sequence data as the target nucleic acid sequence of the target nucleic acid molecule. Thus, it is preferable to consider an assembly of the plurality of nucleic acid sequence data as one target nucleic acid sequence of the target nucleic acid molecule.

Thus, when the plurality of nucleic acid sequence data corresponding to a target nucleic acid molecule is present in one nucleic acid record, nucleic acid sequence data whose sequence data partially or entirely overlap among the plurality of nucleic acid sequence data may be detected and assembled. This process may be referred to as a clustering process. The clustering process may be performed by following steps:

retrieving position information about a sequence of each of the plurality of nucleic acid sequence data corresponding to the target nucleic acid molecule in the one nucleic acid record, wherein the position information is a start-point and an end-point information about a sequence of each of the plurality of nucleic acid sequence data;

analyzing the sequence position information to select nucleic acid sequence data whose sequence data partially or entirely overlap with each other among the plurality of nucleic acid sequence data; and generating new nucleic acid sequence data including all of the selected nucleic acid sequence data.

According to one embodiment of the present invention, the assembling may be performed by sequence data clustering that includes following steps:

(c201) retrieving position information about a sequence of each of a plurality of nucleic acid sequence data; and (c202) analyzing the sequence position information about each nucleic acid sequence data and assembling nucleic acid sequence data whose sequence data partially or entirely overlap with each other among the plurality of nucleic acid sequence data.

The clustering of nucleic acid sequence data overlapping partially or entirely as described in the above description may allow target nucleic acid sequence data of each portion of the target nucleic acid molecule to be recognized as target nucleic acid sequence data of each individual target nucleic acid molecule. Thus, a probability of statistical errors in analysis based on the target nucleic acid sequence data set may decrease.

Homology-Based Additional Sequence Retrieval

According to one embodiment of the present invention, in the method of the present invention, the target nucleic acid sequence data set of the target nucleic acid molecule retrieved in the step (c) may be a first target nucleic acid sequence data set. In this connection, the method further comprises:

(d) determining a representative sequence from the retrieved first target nucleic acid sequence data set; and (e) retrieving, from the second database, nucleic acid sequence data having homology with the representative sequence at a predefined homology value or greater, and further providing an additional nucleic acid sequence data set.

In the steps (d) and (e), homology-based additional sequence retrieval is performed using the target nucleic acid sequence data set retrieved through the steps (a) to (c).

Specifically, in the step (d), the representative sequence is determined from the target nucleic acid sequence data set retrieved through the steps (a) to (c).

The representative sequence refers to a sequence representing the target nucleic acid sequences included in the first target nucleic acid sequence data set. The representative sequence may include one or more representative sequence. The representative sequence determination will be described in detail in Section II.

In the step (e), the nucleic acid sequence data having homology with the determined representative sequence at the predefined value or greater is retrieved. Thus, an additional nucleic acid sequence data set is provided.

The homology refers to relative positional and structural similarity or identity between two or more nucleic acid sequences. The homology may be expressed by quantifying the similarity or identity between two nucleic acid sequences. The homology will be described in detail in Section II.

The homology value above or equal to the predefined value in the step (e) may depend on the intended use of the nucleic acid sequence data to be retrieved. For example, the homology value above or equal to the predefined value in the step (e) may be 10%, 20%, 30%, 40%, 50%, 60%, 70%, 80%, 90% or greater.

A source used for retrieving nucleic acid sequence data in the step (e) is not particularly limited. Preferably, the source may be a database including the nucleic acid sequence data and an identifier of the nucleic acid sequence data. According to one embodiment of the present invention, in the step (e), the nucleic acid sequence data may be retrieved from the second database.

When the representative sequence includes at least two representative sequences, nucleic acid sequence data having homology with each representative sequence at the predefined homology value or greater is retrieved from the second database. Thus, an additional nucleic acid sequence data set is provided. The retrieval may be performed using software (for example, BLAST) known in the art such that a sequence meeting a condition is retrieved from the second database.

The additional nucleic acid sequence data set retrieved through the step (e) may include nucleic acid sequence data about the received source organism. A set of nucleic acid sequence data having homology with the representative sequence at the predefined homology value or greater and associated with the received source organism is called the second target nucleic acid sequence data set.

In a keyword-based target nucleic acid sequence retrieval, when the nucleic acid sequence name is changed after the nucleic acid sequence is registered, or the information about the nucleic acid sequence is erroneously written or omitted due to the mistake of the nucleic acid sequence registrant, the corresponding nucleic acid sequence may not be retrieved. Thus, when nucleic acid sequence data having homology with the representative sequence at the predefined homology value or greater and associated with the received source organism is retrieved and added to the target nucleic acid sequence data set, this may solve the problem of missing the target nucleic acid sequence data for the above reasons.

In one example, the additional nucleic acid sequence data set as retrieved above may include nucleic acid sequence data that are not related to the received source organism. A set of nucleic acid sequence data having homology with the representative sequence at the predefined homology value or greater and non-associated with the received source organism is called an exclusive nucleic acid sequence data set.

The molecular diagnostic kit detects the presence or absence of a specific organism in a sample using an oligonucleotide for target nucleic acid molecule detection that specifically reacts with the target nucleic acid molecule of the organism of interest. The oligonucleotide for target nucleic acid molecule detection of the source organism of interest should satisfy following two requirements:

First, the oligonucleotide for target nucleic acid molecule detection should be able to detect substantially all of various nucleic acid sequences of the target nucleic acid molecule of the organism of interest;

Second, the oligonucleotide for target nucleic acid molecule detection should not detect nucleic acid molecules of organisms other than the organism of interest.

The second target nucleic acid sequence data set may be used to meet the first requirement of the oligonucleotide for target nucleic acid molecule detection of the source organism of interest. The exclusive nucleic acid sequence data set may be used to meet the second requirement of the oligonucleotide for target nucleic acid molecule detection of the source organism of interest. The exclusive nucleic acid sequence will be described in detail in Section III.

According to one embodiment of the present invention, the additional nucleic acid sequence data set provided in the step (e) is provided by at least one of following sub-steps (e1) or (e2):

(e1) retrieving, from the second database, nucleic acid sequence data having a homology with the representative sequence at a first predefined homology value or greater and associated with the received source organism, thereby obtaining a second target nucleic acid sequence data set, and, then, providing an additional nucleic acid sequence data set including the second target nucleic acid sequence data set; and (e2) retrieving, from the second database, nucleic acid sequence data having a homology with the representative sequence at a second predefined homology value or greater and non-associated with the received source organism, thereby obtaining an exclusive nucleic acid sequence data set, and, then, providing an additional nucleic acid sequence data set including the exclusive nucleic acid sequence data set.

The nucleic acid sequence data associated with the received source organism refers to nucleic acid sequence data wherein a name or synonym of the received source organism in the step (a) or a name of or synonym of a source organism belonging to a subclass of the received source organism in terms of classification is recorded as a source organism of the nucleic acid sequence data. The nucleic acid sequence data not related to the received source organism refers to nucleic acid sequence data wherein a name or synonym of the received source organism in the step (a) or a name of or synonym of a source organism belonging to a subclass of the received source organism in terms of classification is not recorded as a source organism of the nucleic acid sequence data.

The step of determining the representative sequence from the first target nucleic acid sequence data set as the step (d), and the step for providing the additional nucleic acid sequence data set that includes the second target nucleic acid sequence data set as the step (e1) will be described in detail in Section II below. Further, the step for providing the additional nucleic acid sequence data set that includes the exclusive nucleic acid sequence data set as the step (e2) will be described in detail in Section III below.

II. Extended Target Nucleic Acid Sequence Data Set Providing Method Using Representative Sequence Determination and Additional Sequence Retrieval Since the synonym retrieval and the nucleic acid sequence data set retrieval using the synonym is based on searching with keyword (search term), it is possible to retrieve related nucleic acid sequences even though the identity between the related nucleic acid sequences is low due to considerable sequence variations.

However, when the name of the nucleic acid molecule is not yet fixed at the time of recording or when a sequence is registered with a name that is not a correct name or synonym of a target nucleic acid molecule due to the registrant's mistake or the like, the sequence of the nucleic acid molecule may not be retrieved by keyword searching, even though the corresponding nucleic acid sequence is actually the target nucleic acid sequence of the target nucleic acid molecule.

In order to eliminate this situation, the method of the present invention further includes a sequence homology-based nucleic acid sequence retrieval step to extend the target nucleic acid sequence data set of the target nucleic acid molecule provided by the method of the present invention.

Figure 6:
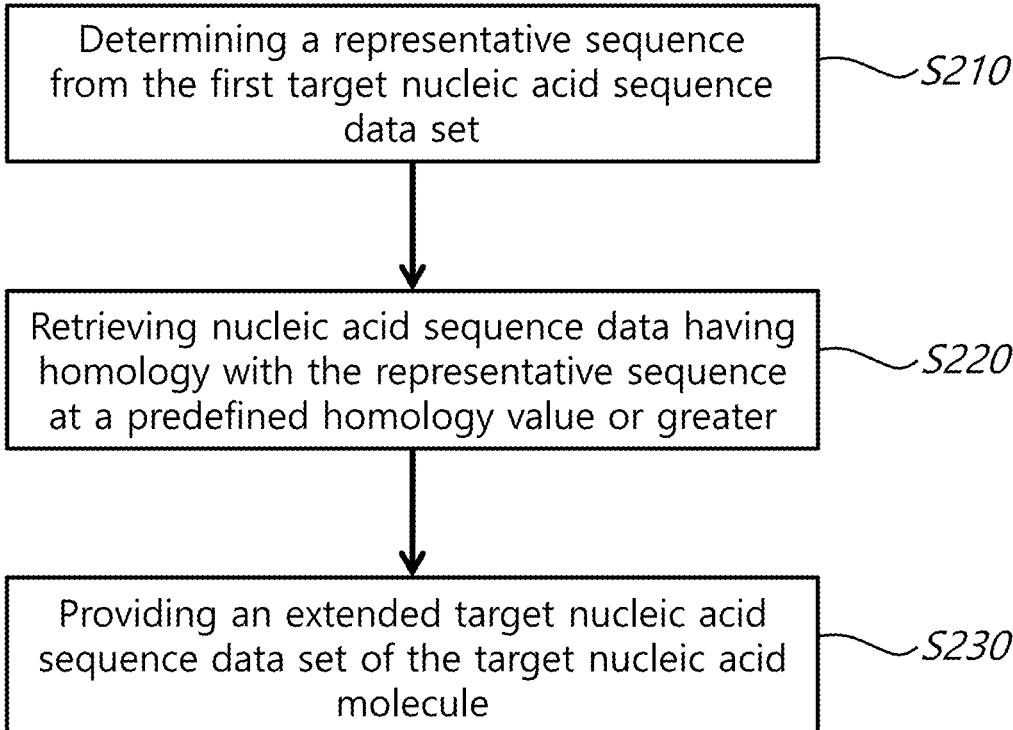
FIG. 6 is a flow chart outlining the process of providing the extended target nucleic acid sequence data set of the present invention.
Figure 9:
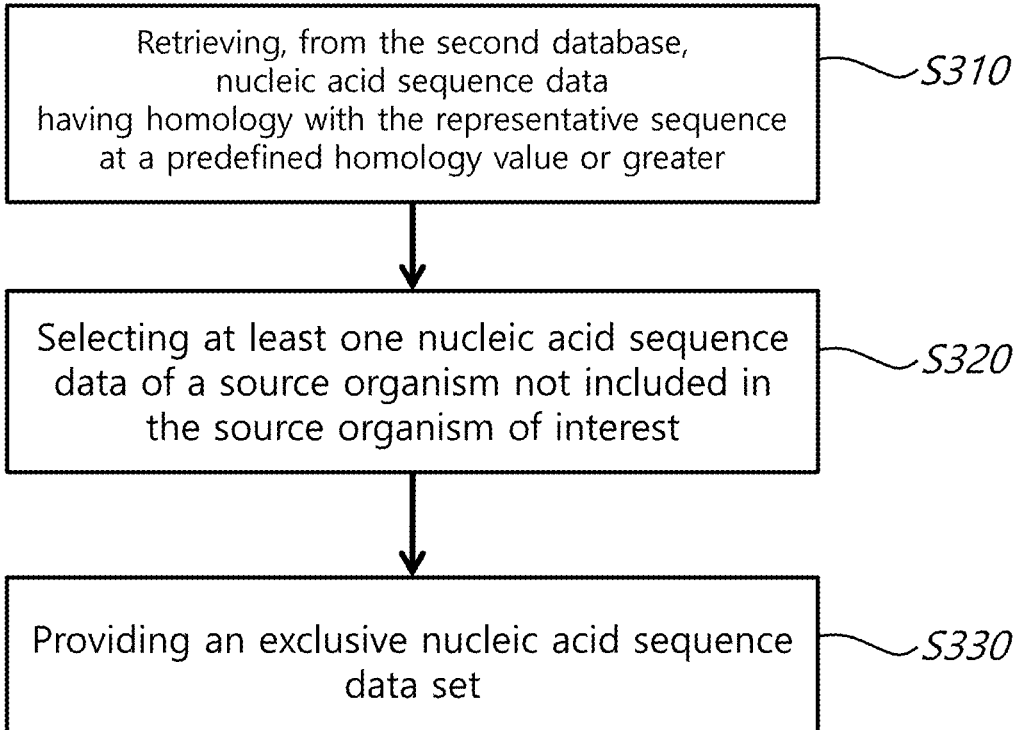
FIG. 9 is a flow chart showing an overview of the process of providing the exclusive nucleic acid sequence data set of the present invention.

As shown in FIG. 6, method for providing the extended target nucleic acid sequence data set according to the present invention comprises representative sequence determination, highly homologous nucleic acid sequence data retrieval using the representative sequence, and extended target nucleic acid sequence data provision. According to the present invention, the extended target nucleic acid sequence data set refers to a combination of the first target nucleic acid sequence data set retrieved using the synonym and the second target nucleic acid sequence data set retrieved using the representative sequence.

According to one embodiment of the present invention, the target nucleic acid sequence data set of the target nucleic acid molecule retrieved in the step (c) is the first target nucleic acid sequence data set. The method of the present invention may further include following steps:

(d) determining a representative sequence from the retrieved first target nucleic acid sequence data set; and (e) retrieving, from the second database, nucleic acid sequence data having homology with the representative sequence at a predefined homology value or greater, and further providing an additional nucleic acid sequence data set.

Further, the additional nucleic acid sequence data set provided in the step (e) is provided by a following sub-step (e1):

(e1) retrieving, from the second database, nucleic acid sequence data having a homology with the representative sequence at a first predefined homology value or greater and associated with the received source organism, thereby obtaining a second target nucleic acid sequence data set, and, then, providing an additional nucleic acid sequence data set including the second target nucleic acid sequence data set.

To further distinguish between the target nucleic acid sequence data set of the target nucleic acid molecule retrieved in the step (c) and the nucleic acid sequence data set further retrieved to extend the target nucleic acid sequence data set of the target nucleic acid molecule, the target nucleic acid sequence data set of the target nucleic acid molecule retrieved in the step (c) is named the first target nucleic acid sequence data set, while the target nucleic acid sequence data set further retrieved using the representative sequence is named the second target nucleic acid sequence data set.

2-1. Determining Representative Sequence from Retrieved First Target Nucleic Acid Sequence Data Set The step (d) determines the representative sequence from the retrieved first target nucleic acid sequence data set through the steps (a) to (c). One nucleic acid sequence may be determined as a representative sequence. Alternatively, a plurality of nucleic acid sequences may be determined as the representative sequences.

In order to retrieve the nucleic acid sequence based on sequence homology, a sequence acting as a reference for measuring the homology is needed. According to the present invention, the second target nucleic acid sequence data set is provided by determining the representative sequence and by retrieving the sequence based on homology with the determined representative sequence.

The homology refers to the relative positional and structural similarity or identity between two or more nucleic acid sequences. The homology may be expressed by quantifying the similarity or identity between two nucleic acid sequences.

For example, when two nucleic acid sequences are completely identical with each other, the homology between them is 100%. When a non-identical sequence between the two nucleic acid sequences is present, the homology percentage (%) value is reduced. In general, the homology percentage may refer to a quantification of the degree of identity between two nucleic acid sequences. The degree of homology may be determined by comparing specific positions of sequences that are aligned with each other for comparison. When bases of the specific positions of the two sequences being compared are the same, the two nucleic acid molecules have homology at the corresponding position. The degree of homology between two sequences may be calculated as a function of the number of homologous positions shared by the two sequences.

The alignment refers to a set of techniques that juxtaposes the molecule sequences having homology. In bioinformatics, a sequence alignment is a way of arranging the sequences of DNA, RNA, or protein to identify regions of similarity. The alignment of the sequences and the calculation of the homology value of the sequences may be determined by software (for example, BLAST) known in the art.

The homology may refer to the identity or similarity. The identity is determined based on whether the bases of the specific positions of the two sequences being compared are identical with each other. The similarity may be determined by determining, based on characteristics of the bases of the specific positions of the two sequences being compared, whether the bases are identical, or whether the bases have a similar characteristic when the bases are not identical, or whether the bases have different characteristics when the bases are not identical, and by quantitatively calculating the determining results.

According to one embodiment of the present invention, the representative sequence to be determined may be at least one nucleic acid sequence. The representative sequence may be determined by a known program.

According to one embodiment of the present invention, the representative sequence is determined from the nucleic acid sequences belonging to the retrieved first target nucleic acid sequence data set. The determination may be based on (i) a sequence length of the nucleic acid sequence belonging to the first target nucleic acid sequence data set, and (ii) a homology value of the nucleic acid sequence belonging to the first target nucleic acid sequence data set with other nucleic acid sequences belonging to the first target nucleic acid sequence data set.

According to one embodiment of the present invention, the representative sequence may be determined from the nucleic acid sequences belonging to the retrieved first target nucleic acid sequence data set using a pre-determined homology reference value and a homology value between the nucleic acid sequences belonging to the first target nucleic acid sequence data set.

The pre-determined homology reference value refers to a reference value used when classifying the nucleic acid sequences belonging to the first target nucleic acid sequence data set based on the homology values between the nucleic acid sequences belonging to the first target nucleic acid sequence data set, or when selecting at least one nucleic acid sequence as a representative sequence.

The homology reference value may be determined according to the characteristics of the target nucleic acid molecule. For example, the homology reference value may vary based on a range of the target nucleic acid molecule. For example, the homology reference value may vary depending on whether the target nucleic acid molecule is specific to a specific species or is specific to a specific subspecies. Alternatively, the homology reference value may vary depending on the degree of variation of the target nucleic acid molecule to be detected.

The homology reference value may be determined as, for example, 70%, 80%, 90% or greater. Specifically, the homology reference value may be determined in a range of 70% to 100%, 80% to 100%, or 90% to 100%.

When a plurality of representative sequences is determined, a homology value between the representative sequences is lower than the homology reference value. When the homology value between two representative sequences is greater than the homology reference value, the two representative sequences must belong to one nucleic acid sequence group and may not be regarded as nucleic acid sequences representing different nucleic acid sequence groups respectively.

According to one embodiment of the present invention, the representative sequence may be determined by the method comprising: classifying nucleic acid sequences belonging to the retrieved first target nucleic acid sequence data set into at least one nucleic acid sequence group, using the pre-determined homology reference value, and homology values between the nucleic acid sequences belonging to the first target nucleic acid sequence data set; wherein each of the at least one nucleic acid sequence group includes one representative sequence; wherein the representative sequence has a homology value with all nucleic acid sequences in the same nucleic acid sequence group at the pre-determined homology reference value or greater; and wherein the homology between the representative sequences has a homology value lower than the pre-determined homology reference value.

According to one embodiment of the present invention, all nucleic acid sequence data included in the first target nucleic acid sequence data set may be classified into a plurality of nucleic acid sequence groups, each group including one representative sequence. The plurality of nucleic acid sequence groups may be classified such that the representative sequences thereof are determined to satisfy following conditions:

(i) each of homology values between all representative sequences is below the homology reference value.

(ii) each of all representative sequences has a homology value greater than the homology reference value with the nucleic acid sequences of the nucleic acid sequence group to which each representative sequence belongs to.

The determination of the representative sequence and the nucleic acid sequence group in accordance with the conditions may be performed by a known analysis program according to various algorithms.

The algorithm may be, for example, as follows. The retrieved target nucleic acid sequence data of the target nucleic acid molecule is designated as a non-classified data group. Then, the first representative sequence is determined from the non-classified data group according to a predefined manner (for example, determining the longest sequence as a representative sequence). Then, sequences having a homology value equal to or greater than the homologous reference value with the first representative sequence may be excluded from the non-classified data group. Then, the second representative sequence is determined by the predetermined manner from the non-classified data group free of the previously excluded sequences. Then, sequences having a homology value equal to or greater than the homologous reference value with the determined second representative sequence may be excluded from the non-classified data group. The process may be repeated until no more nucleic acid sequence data remains in the non-classified data group, thereby determining the representative sequences.

2-2. Providing Second Target Nucleic Acid Sequence Data Set of Target Nucleic Acid Molecule The step (e) includes retrieving the nucleic acid sequence data having the homology with the representative sequence at the predefined homology value or greater from the second database and providing the second target nucleic acid sequence data set of the target nucleic acid molecule.

According to one embodiment of the present invention, the additional nucleic acid sequence data set provided in the step (e) is provided by the following sub-steps (e1):

(e1) retrieving, from the second database, nucleic acid sequence data having a homology with the representative sequence at a first predefined homology value or greater and associated with the received source organism, thereby obtaining a second target nucleic acid sequence data set, and, then, providing an additional nucleic acid sequence data set including the second target nucleic acid sequence data set.

The homology value above or equal to the predefined homology value may be at least 70%, 80%, 90%, 95%, 96%, 97%, 98% or 99% or greater. The predefined homology value may be in a certain range, for example, a range of 70% to 100%, 80% to 100%, 90% to 100% or 95% to 100% but is not limited thereto.

As used herein, in order to distinguish "the predefined homology value" used in the step (e1) to provide the second target nucleic acid sequence data set from other "predefined homology values", the former may be referred to as "a first predefined homology value".

The retrieval may be performed by retrieving a sequence meeting the condition from the second database using software (for example, BLAST) known in the art.

According to one embodiment of the present invention, the nucleic acid sequence data having the homology with the representative sequence at the first predefined homology value or greater are retrieved from the second database. Then, information on the source organisms of the retrieved sequences is compared with information on the source organism of the target nucleic acid molecule. Then, nucleic acid sequence data to be included in the second target nucleic acid sequence data set may be selected based on the comparisons.

Information on the source organism may be a title for each sequence or a taxonomic identification (ID) symbol assigned to each sequence.

The selection may be, for example, performed by a method as follows: When the information about the source organism of the retrieved nucleic acid sequence is the same as the information about the source organism of the target nucleic acid molecule, or is the same as the information about the source organism belonging to a subclass of the source organism of the target nucleic acid molecule, the retrieved nucleic acid sequence is determined as the nucleic acid sequence included in the second target nucleic acid sequence data set.

By providing second target nucleic acid sequence data set of target nucleic acid molecule as described above, it is possible to additionally retrieve the target nucleic acid sequence that have been omitted in the first target nucleic acid sequence data set due to insufficient synonyms retrieval or incorrect information (e.g. name of source organism or gene) recorded in the initial sequence registration.

In one example, the method of the present invention further comprises (f) combining the first target nucleic acid sequence data set and the second target nucleic acid sequence data set to provide an extended target nucleic acid sequence data set of the target nucleic acid molecule.

The step (f) provides an extended target nucleic acid sequence data set of the target nucleic acid molecule by combining the first target nucleic acid sequence data set obtained previously with the second target nucleic acid sequence data set.

The extended target nucleic acid sequence data set becomes a more complete target nucleic acid sequence data for the target nucleic acid molecule by adding sequence retrieved based on sequence homology to the first target nucleic acid sequence data set retrieved based on the keyword.

According to one embodiment of the present invention, the combining of the first target nucleic acid sequence data set and the second target nucleic acid sequence data set may comprise removing duplicate sequences between nucleic acid sequences of the first target nucleic acid sequence data set and the second target nucleic acid sequence data set.

According to one embodiment of the present invention, the providing of the extended target nucleic acid sequence data set may include including alignment information with the representative sequence into the extended target nucleic acid sequence data set. Thus, the extended target nucleic acid sequence data set may be used more effectively for a desired oligonucleotide design.

According to one embodiment of the present invention, the method of the present invention may not involve the step (f) of combining the first target nucleic acid sequence data set with the second target nucleic acid sequence data set, but may provide each of the first target nucleic acid sequence data set and the second target nucleic acid sequence data set individually.

According to another aspect of the present invention, the present invention provides a computer-implemented method for providing a target nucleic acid sequence data set of a target nucleic acid molecule, the method comprising:

(a) retrieving nucleic acid sequence data using a name of a target nucleic acid molecule and information on a source organism thereof, thereby providing a first target nucleic acid sequence data set of the target nucleic acid molecule;

(b) determining at least one representative sequence from the provided first target nucleic acid sequence data set;

(c) retrieving, from a second database, nucleic acid sequence data having homology with the representative sequence at a predefined homology value or greater, thereby providing a second target nucleic acid sequence data set of the target nucleic acid molecule; and (d) combining the first target nucleic acid sequence data set with the second target nucleic acid sequence data set, thereby providing an extended target nucleic acid sequence data set of the target nucleic acid molecule.

The extended target nucleic acid sequence data set of the target nucleic acid molecule may be automatically retrieved by the above method. The extended target nucleic acid sequence data set may provide the target nucleic acid sequence data of the target nucleic acid molecule more specific to the target nucleic acid molecule compared to the target nucleic acid sequence data set retrieved based on the synonym.

The description of each step of the above method is as described above.

III. Additional Nucleic Acid Sequence Data Set Providing Method Using Exclusive Nucleic Acid Sequence Retrieval 3-1. Exclusive Nucleic Acid Sequence Retrieval A sequence of a gene may have various variant sequences. Thus, sequence information about the same gene in the same source organism may have various versions of sequence information registered in the nucleotide database.

According to the method of the present invention described so far, such various versions of sequence information can be automatically retrieved and provided without omission thereof by a computer. The researchers who develop an oligonucleotide that is used to detect a specific gene or sequence may easily develop the oligonucleotide that can be used to detect all of the target genes, based on the sequences provided above, despite the presence of the various variations.

Another challenge in the development of oligonucleotides for specific target detection is that information about nucleic acid molecules that may lead to false positives should be identified so that such nucleic acid molecules are not detected.

In order to solve this challenge, the method of the present invention may provide an additional nucleic acid sequence data set that includes an exclusive nucleic acid sequence data set that may be used in the development of oligonucleotides for target nucleic acid molecule detection, in addition to the target nucleic acid sequence data set.

According to one embodiment of the present invention, the target nucleic acid sequence data set of the target nucleic acid molecule retrieved from the step (c) of the Section I is the first target nucleic acid sequence data set. The method of the present invention may further include following steps:

(d) determining a representative sequence from the retrieved first target nucleic acid sequence data set; and (e) retrieving, from the second database, nucleic acid sequence data having homology with the representative sequence at a predefined homology value or greater, and further providing an additional nucleic acid sequence data set.

According to one embodiment of the present invention, the additional nucleic acid sequence data set provided in the step (e) is provided by a following sub-step (e2):

(e2) retrieving, from the second database, nucleic acid sequence data having a homology with the representative sequence at a second predefined homology value or greater and non-associated with the received source organism, thereby obtaining an exclusive nucleic acid sequence data set, and, then, providing an additional nucleic acid sequence data set including the exclusive nucleic acid sequence data set.

As used herein, in order to distinguish "the predefined homology value" used in the step (e2) to provide the exclusive target nucleic acid sequence data set from other "predefined homology values", the former may be referred to as a second predefined homology value.

The homology value above or equal to the second predefined homology value may be at least 40%, 50%, 60%, 70%, 80%, 90% or greater. The second predefined homology value may be in a range of values, for example, 40% to 100%, 50% to 100%, 60% to 100%, 70% to 100%, 80% to 100% or 90% to 100% but is not limited thereto.

The second predefined homology value to provide the exclusive nucleic acid sequence may be equal to or different from the first predefined homology value used to provide the previously described second target nucleic acid sequence data set. Specifically, the second predefined homology value may be equal to or lower than the first predefined homology value.

As used herein, the term "exclusive nucleic acid sequence (EXseq)" or "exclusive nucleic acid sequence data (EXseq data)" refers to nucleic acid sequence or nucleic acid sequence data of a non-target nucleic acid molecule. As used herein, the terms "exclusive nucleic acid sequence" and "non-target nucleic acid sequence" are used interchangeably. The non-target nucleic acid molecule is opposite to the target nucleic acid molecule. The non-target nucleic acid molecule means a nucleic acid molecule that should not be detected during the detection of a target nucleic acid molecule, regardless of homology with the sequence of the target nucleic acid molecule.

Thus, the method may retrieve, from the second database, as the exclusive target nucleic acid sequence data set, nucleic acid sequence data having a homology with the representative sequence at a second predefined homology value or greater and non-associated with the received source organism.

The retrieval of the nucleic acid sequence data that is not related to the received source organism may be performed by comparing the received information about the source organism of the target nucleic acid molecule with the information about the source organism of the nucleic acid sequence having a homology with the representative sequence at the second predefined homology value or greater.

Specifically, the method comprises: retrieving, from the second database, nucleic acid sequence data having a homology value equal to or greater than the second predefined homology value, and information about source organisms thereof; classifying nucleic acid sequence data whose source organism not belongs to the source organism received in the step (a) or an organism of a subclass thereof into the EXseq data; and, then obtaining the exclusive nucleic acid sequence data set (EXseq data set).

Information about the source organism may be a title of each sequence or a taxonomic identification symbol ID assigned to each sequence.

The EXseq data set retrieved in this way includes nucleic acid sequences which is similar to the target nucleic acid sequences but which is not the target nucleic acid sequence. Therefore, when, in the process of preparing an oligonucleotide for target nucleic acid molecule detection, the oligonucleotide is produced not to be hybridized with the nucleic acid sequences included in the EXseq data set, the oligonucleotide for target nucleic acid molecule detection with high specificity and no risk of false positive error can be prepared.

3-2. Essential Exclusive Nucleic Acid Sequence Retrieval

The false positive error due to the non-target nucleic acid molecules similar to the target nucleic acid molecule becomes even worse when a portion of the sequence of the non-target nucleic acid molecule is highly similar to the sequence of the target nucleic acid molecule. A non-target nucleic acid sequence which is highly homologous to the target nucleic acid sequence only in a specific region, but non-homologous in the other region has a low overall sequence homology with the target nucleic acid molecule. If these sequences are not considered during the oligonucleotide design process, oligonucleotides with the potential for false-positive error are likely to be designed. Nevertheless, generally these nucleic acid sequences are not considered in the oligo design process.

In accordance with the present invention, to solve this problem, the present invention provides a method for selecting the non-target sequence having the partial region having a high homology with the target nucleic acid molecule although the overall homology of the non-target sequence with the target nucleic acid molecule is low, and for providing information on the selected non-target sequence.

According to one embodiment of the present invention, the step (e2) for providing the additional nucleic acid sequence data set that includes the exclusive nucleic acid sequence data set may comprise:

retrieving, from the second database, partial nucleic acid sequence data having a homology with a partial region of the representative sequence at a third predefined homology value or greater, wherein the partial nucleic acid sequence data is contained as a partial region of the nucleic acid sequence data having a homology with the representative sequence at the second predefined homology value or greater and non-associated with the received source organism; obtaining an exclusive target nucleic acid sequence data set containing the partial nucleic acid sequence data; and providing an additional nucleic acid sequence data set including the exclusive nucleic acid sequence data set.

To distinguish the EXseq data set obtained by the method from the exclusive nucleic acid sequence data set of the section 3-1, the former may be called the essential exclusive nucleic acid sequence (essential EXseq) data set.

Figure 10:
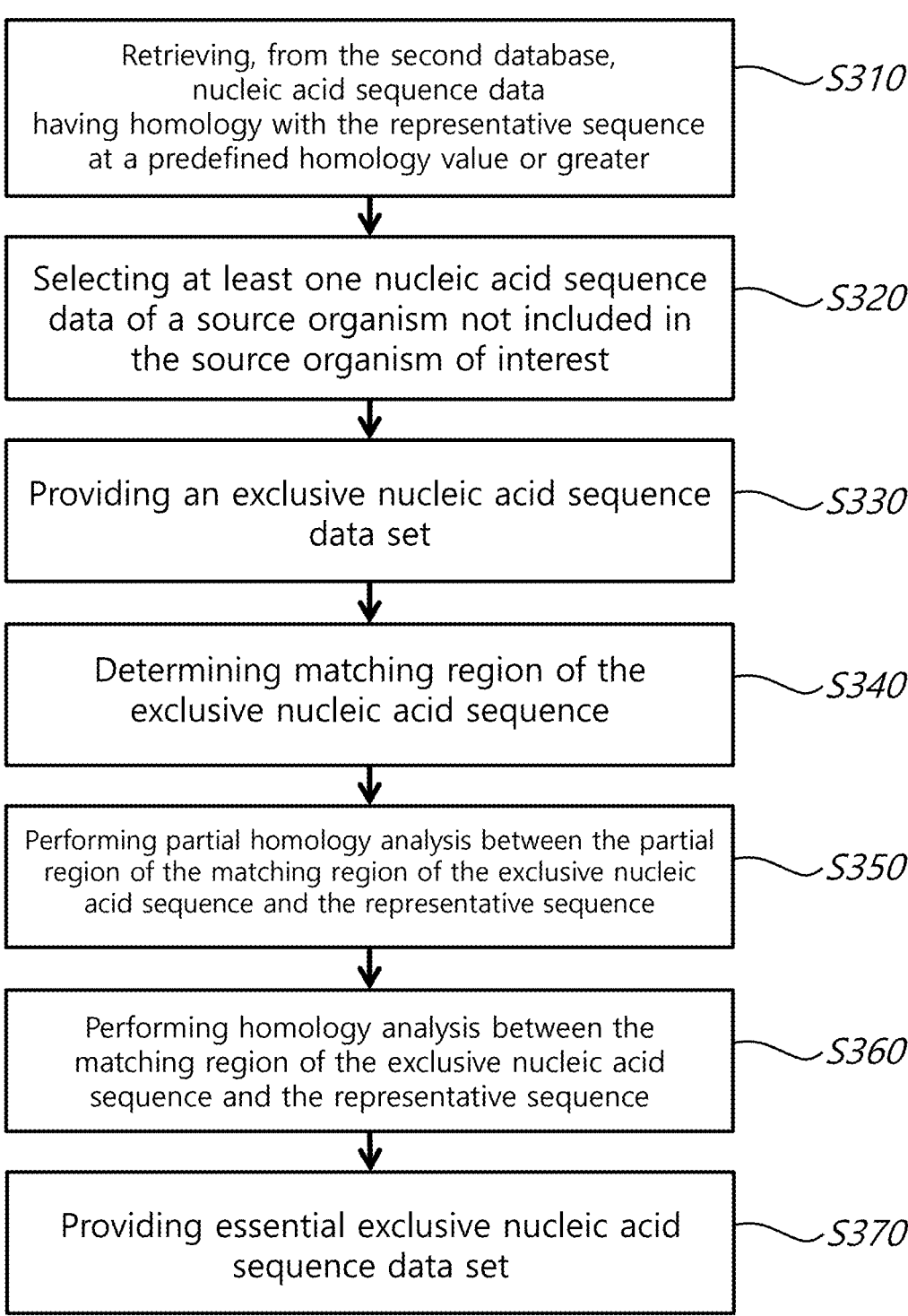
FIG. 10 is a flow chart showing an overview of the process of selecting and providing the essential exclusive nucleic acid sequence data from the exclusive nucleic acid sequence data set of the present invention.

The essential EXseq data set providing method in accordance with the present invention includes homology analysis between the partial region of the retrieved EXseq and the representative sequence as shown in FIG. 10.

According to one embodiment of the present invention, when the partial region of an EXseq has a homology value equal to or greater than the predefined homology value with the representative sequence, the method may select the EXseq as the essential EXseq and provide an EXseq data set.

As used herein, in order to distinguish the "predefined homology value" used for comparison between the partial region of the EXseq and the representative sequence to provide the essential EXseq data set from other "predefined homology values", the former may be named a third predefined homology value.

The method for retrieving the essential EXseq data may be, for example, performed as follows.

First, the method determines a portion of EXseq for the partial region analysis (hereafter referred to as a matching region). The matching region of the EXseq refers to a region corresponding to the representative sequence in EXseq. In other words, when an EXseq and representative sequence are aligned, an aligned region or overlapping region is the matching region.

The matching region of the EXseq has the same sequence length as that of the representative sequence.

When an EXseq and representative sequence are subjected to alignment related analysis, the matching region may be determined around a region in EXseq in which the sequence thereof matches the representative sequence. For example, the length of the entire nucleic acid sequence of the nucleic acid record containing the EXseq is 1000 nt, the length of the representative sequence is 300 nt. In this case, from the alignment result of these two sequences, the 101th nt to the 170th nt of the representative sequence are found to match the 351th nt to the 420th nt of the entire nucleic acid sequence of the nucleic acid record containing the EXseq. In this case, the matching region with the representative sequence in the EXseq occupies 251th to 550th nt of the entire nucleic acid sequence of the nucleic acid record containing the EXseq.

Next, it is evaluated whether a partial region among the matching region of EXseq thus determined has a homology value equal to or greater than the third predefined homology value with the representative sequence.

The partial region is determined from the matching region of the EXseq. A plurality of partial regions may be designated. Further, the plurality of partial regions may overlap each other. Since the partial region is used to determine EXseq, the partial may also be named as EX-template. The terms "partial region" and "EX-template" may be used interchangeably.

In one embodiment of the present invention, the partial region may be provided by determining the start-point and end-point of the partial region.

According to one embodiment of the present invention, the start-points of a plurality of overlapping partial regions may be distributed throughout the matching region of EXseq. When the partial regions are arranged evenly over the entire matching region of EXseq, and at least one of these partial regions has a high homology with the target nucleic acid sequence, the method may classify the EXseq as essential EXseq. According to one embodiment of the present invention, the start-points of the partial regions may be distributed across the matching region of EXseq according to certain rules. For example, the start-points of the partial regions may be distributed at a constant spacing over the matching region of EXseq. The constant spacing may vary depending on the length of the matching region of the EXSEq. For example, the spacing includes, but is not limited to, a value between 1-100 nt, 1-90 nt, 1-80 nt, 1-70 nt, 1-60 nt, 1-50 nt, 1-40 nt, 1-30 nt, 1-20 nt, 1-10 nt, or 1-5 nt.

According to one embodiment of the present invention, the start-points of the partial regions may be arranged at a 1 nt spacing over the matching region of the exclusive nucleic acid sequence. As used herein to denote the length of a nucleic acid or the position of a nucleotide, the term "nt" refers to the abbreviation of nucleotide and refers to a length of a single-stranded or double-stranded nucleic acid molecule. For example, the 10th nt of a nucleic acid molecule means a nucleotide at the 10th position from a 5'-end of a nucleic acid molecule. A nucleic acid molecule of 100 nt means a nucleic acid molecule having a 100-nucleotide length. In a single-stranded nucleic acid molecule, the nucleic acid molecule of 100 nt means a nucleic acid molecule consisting of 100 nucleotides. When the nucleic acid molecule is based on a double strand, nt means bp (base pair) and nt may be interchanged with bp. Thus, a double-stranded nucleic acid molecule whose each single strand having a 100 nt length, may be expressed as 100 nt or 100 bp in terms of its length.

According to one embodiment of the present invention, the lengths of the partial regions may all be the same. Thus, the end point of the partial region may be determined to be a point separated from the start-point of the partial region by a predetermined nucleic acid length.

The length of the partial region may be appropriately selected depending on the length of the matching region of the exclusive nucleic acid sequence, the type of the target nucleic acid molecule, or the length of the oligonucleotide to be developed. For example, when the length of the matching region of an exclusive nucleic acid sequence is long and when the partial region is determined to be too short, the data processing time may be long. To the contrary, when a target nucleic acid molecule to be distinguished from the exclusive nucleic acid sequence is a well-known nucleic acid molecule, and when the length of the partial region is set to be too long, a nucleic acid sequence to be distinguished from the target nucleic acid molecule may not be selected as an essential exclusive nucleic acid sequence and may be missed.

According to one embodiment of the present invention, the length of the partial region may be a value in a range of between 10 nt to 300 nt, 10 nt to 200 nt, 10 nt to 100 nt, 20 nt to 100 nt, 30 nt to 100 nt, 40 nt to 100 nt or 50 nt to 100 nt.

According to one embodiment of the present invention, the length of the partial region may be determined by comparing the predefined reference value with the length of the matching region of the exclusive nucleic acid sequence. For example, when the length of the matching region of an exclusive nucleic acid sequence is greater than or equal to the reference value, the partial region is set to a predefined first length. When the length of the matching region of the exclusive nucleic acid sequence is smaller than the reference value, the partial region may be set to a predefined second length.

The reference value may be determined appropriately in consideration of the performance of the analysis system, and may be not limited to, but include, for example, a value in a range between 50 to 1000 nt, 50 to 900 nt, 50 to 800 nt, 50 to 700 nt, 50 to 600 nt, 50 to 500 nt, 100 to 500 nt, 100 to 400 nt, or 200 to 400 nt. For example, if the reference value is 350 nt, and if the length of the matching region of the exclusive nucleic acid sequence is 350 nt or greater, the length of the partial region is set to a predefined first length. If the length of the matching region of the exclusive nucleic acid sequence is smaller than 350 nt, the length of the partial region may be set to a predefined second length.

A first length as a length of the partial region applied when the length of the matching region of an exclusive nucleic acid sequence is greater than or equal to the reference value may usually be set to a length suitable for searching for the exclusive sequence. In the determination of the first length, the degree of variation of the target nucleic acid molecule and the similarity in the sequence between the target nucleic acid molecule to be detected and the non-target nucleic acid molecule to be distinguished therefrom may be considered. According to one embodiment of the present invention, the first length may be, for example, a value in a range of 50 to 500 nt, 50 to 400 nt, 50 to 300 nt, 50 to 200 nt, 60 to 200 nt, 70 to 200 nt, 80 to 200 nt, 90 to 200 nt, 100 to 200 nt, or 100-150 nt.

A second length as a length of the partial region applied when the length of the matching region of an exclusive nucleic acid sequence is not exceeding the reference value may be set to be smaller than the first length. This may prevent an unduly long length from being set to the length of the partial region when the length of the target nucleic acid sequence is too small.

According to one embodiment of the present invention, the second length may be, for example, a value in a range of 10 to 100 nt, 10 to 90 nt, 10 to 80 nt, 10 to 70 nt, 10 to 60 nt, 20 to 60 nt, 30 to 60 nt, 40 to 60 nt or 40 to 50 nt.

According to one embodiment of the present invention, a length of the partial region may be defined based on a specific ratio of a length of the partial region to the length of the matching region of the exclusive nucleic acid sequence. The specific ratio may be, for example, a value in a range of 1-50%, 1-40%, 1-30%, 1-25%, or 2-25%. When the specific ratio is excessively low, the partial region is too short, which may be inefficient. To the contrary, when the specific ratio is excessively high, the partial region is too long in a long target nucleic acid sequence, which may be inefficient.

According to one embodiment of the present invention, the partial region is set to have a length of 50 to 100 nt, and the partial regions may be arranged to overlap at a 1 to 5 nt spacing from the start-point of the matching region of EXseq. The method may determine whether the EXseq is classified as the essential EXseq by evaluating whether or not each of the generated partial regions has a homology equal to or greater than the predefined homology value with the representative sequence.

The homology value above or equal to the third predefined homology value may be greater or equal to 80%, 90%, 91%, 92%, 93%, 94%, 95%, 96% or 97% homology value. The third predefined homology value may be in a range of values, for example, 80% to 100%, 90% to 100%, 95% to 100% or 97% to 100% but is not limited thereto.

If one of the partial regions of the matching region of an EXseq has the homology value with the representative sequence greater than or equal to the third predefined homology value, the EXseq may be classified as essential EXseq.

For example, the first partial region may be set to occupy 1st nt to 100th nt of the matching region of EXseq, and the second partial region may be set to occupy 2nd nt to 101-st nt thereof. In this case, when the length of the matching region of EXseq is 500 nt, the partial region may be set to include 401 partial regions occupying a range from 1st to 100th nt to 401st to 500th nt. Then each partial region as generated is aligned with the representative sequence.

When there is a partial region having the homology value with the representative sequence greater than or equal to the predefined homology value, the method may classify the EXseq as essential EXseq.

When partial regions are arranged to be overlapped using the above sliding method, the analysis may confirm the all EXseq which is partially similar in sequence to the target nucleic acid molecule. This scheme may also provide sufficient information for designing of oligonucleotide for target nucleic acid molecule detection.

In one example, to select the essential EXseq under a more stringent condition, a criterion that the matching region itself of the EXseq has a homology with the representative sequence at a homology value greater than or equal to a predefined homology value may be added to a criterion that the partial region of the matching region of the EXseq has a homology with the representative sequence at a homology value greater than or equal to the third predefined homology value, thereby selecting essential EXseq.

The predefined homology value may have a smaller value than the third predefined homology value and may have a larger value than the second predefined homology value.

Thus, according to one embodiment of the present invention, when the entire matching region of the EXseq has a homology with the representative sequence at a homology value greater than or equal to the predefined homology value and when the partial region of the matching region of the EXseq has a homology with the representative sequence at a homology value greater than or equal to the third predefined homology value, the method may retrieve the EXseq as the essential EXseq to determine EXseq data set.

For description of this implementation, one example may be assumed in which one of the EXseqs retrieved from the nucleotide database using a representative sequence with a length of 300 nt has a length of the entire nucleic acid sequence of 1000 nt, and in which when these two sequences are aligned with each other, the 101st nt to 170th nt of the representative sequence were found to match a range from the 351st nt to the 420th nt of the total nucleic acid sequence of the nucleic acid record containing the EXseq. In this case, the matching region of the EXSEq corresponding to the representative sequence has a range of from 251st to 550th nt.

First, partial regions, each having 100 nt length are arranged to be overlapped with each other at a 1 nt spacing over a range of 251st to 550th nt of the matching region of EXseq. Then, the partial regions are individually aligned with the representative sequence to evaluate whether there is a partial region with a homology greater than or equal to the third predefined homology value (for example, 90%) with the representative sequence. Second, the method compares the 251st to 550th nt (matching region) of the EXseq with the entire representative sequence (1st to 300th nt) to evaluate whether the two sequences have a homology greater than or equal to the predefined homology value (for example, 70%) with each other. If both of the two criteria are met, the method may classify the EXseq as essential EXseq.

The homology above or equal to the predefined homology value of the entire matching region of the EXseq with the representative sequence may be equal to or greater than 60%, 70%, 80%, 85% or 90% homology value. The third predefined homology value may be in a range of values, for example, in a range of 60% to 100%, 70% to 100%, 80% to 100%, 85% to 100% or 90% to 100% but is not limited thereto.

Thus, when the matching region itself of the EXseq has a homology with the representative sequence at a homology value greater than or equal to the predefined homology value and when the partial region of the matching region of the EXseq has a homology with the representative sequence at a homology value greater than or equal to the third predefined homology value, the method may retrieve the EXseq as the essential.

In this way, the method may retrieve the essential EXseq from the EXseq and determine the same as an EXseq data set.

The EXseq and/or essential EXseq selected in this way is determined as the EXseq data set. The EXseq data set may include both the EXseq and essential EXseq. In one example, the EXseq data set may include EXseq only, or include only essential EXseq, as needed. When the EXseq data set includes both the EXseq and essential EXseq, the method may add identifiers to distinguish between the EXseq and the essential EXseq.

3-3. Providing Determined Exclusive Nucleic Acid Sequence Data Set

The exclusive nucleic acid sequence data set as determined in the above manner may be performed by a known data providing scheme. For example, an output device or a display device may be used to expose content of the data to the user such that the user directly recognizes the data. Alternatively, the data may be provided to the user in such a way that the data is stored by a storing machine in a data storage medium intended by the user. Alternatively, the data may be provided by transmitting the data to a device intended by the user via a network device capable of wired or wireless data transmission.

According to one embodiment of the present invention, the providing of the exclusive nucleic acid sequence data set as determined may include providing the exclusive nucleic acid sequence data belonging to the exclusive nucleic acid sequence data set together with the position information in the exclusive nucleic acid sequence of the partial region having the homology with the representative sequence.

According to one embodiment of the present invention, the providing may include providing the exclusive nucleic acid sequence data set and an alignment result between the exclusive nucleic acid sequence and representative sequence. Further, the exclusive nucleic acid sequence data set may be provided together with the extended target nucleic acid sequence data set.

According to one embodiment of the present invention, the exclusive nucleic acid sequence data set may be provided by providing the additional nucleic acid sequence data sets that include the exclusive nucleic acid sequence data set.

According to one embodiment of the present invention, the step of providing the determined exclusive nucleic acid sequence data set may include at least one of the following sub-steps:

(i1) providing alignment information between the representative sequence and the exclusive nucleic acid sequence data set; and (i2) providing a total nucleic acid sequence data set including the extended target nucleic acid sequence data set and the exclusive nucleic acid sequence data set.

The total nucleic acid sequence data set includes all nucleic acid sequence information related to the target nucleic acid molecule to be analyzed. Therefore, this may allow achieving various analysis and development solutions for target nucleic acid molecule analysis based on the total nucleic acid sequence data set.

The total nucleic acid sequence data set may include whether the included sequence is the exclusive nucleic acid sequence and include metadata of the included sequence.

Further, the determined exclusive nucleic acid sequence data set may be provided in a state in which the exclusive nucleic acid sequence data set is aligned with the representative sequence. The alignment between the representative sequence and the exclusive nucleic acid sequence data set may be performed by well-known alignment software.

The alignment information between the exclusive nucleic acid sequence data set and the representative sequence allows the development of oligonucleotides with high specificity.

According to another aspect of the present invention, the present invention provides a computer-implemented method for providing a target nucleic acid sequence data set of a target nucleic acid molecule, the method comprising:

(a) retrieving nucleic acid sequence data using a name of a target nucleic acid molecule, synonyms thereof, and information about a source organism thereof, thereby providing a first target nucleic acid sequence data set of the target nucleic acid molecule;

(b) determining representative sequence from the retrieved first target nucleic acid sequence data set;

(c) retrieving, from a nucleotide database, nucleic acid sequence data having homology with the representative sequence at a predefined homology value or greater, thereby providing a second target nucleic acid sequence data set of the target nucleic acid molecule; and (d) retrieving, from the nucleotide database, nucleic acid sequence data having a homology value greater than or equal to a predefined homology value with the selected representative sequence.

According to one implementation, the method additionally comprises following steps:

(e) determining an exclusive nucleic acid sequence data set by evaluating source organisms of the nucleic acid sequences retrieved in the step (d); and (f) combining the first target nucleic acid sequence data set with the second target nucleic acid sequence data set and the exclusive nucleic acid sequence data set to provide a total nucleic acid sequence data set of the target nucleic acid molecule.

Using this method, the nucleic acid sequence data set necessary for development of the oligonucleotide for target nucleic acid molecule detection may be automatically retrieved. In particular, the exclusive nucleic acid sequence data set includes all of the exclusive nucleic acid sequence data whose partial regions have a high homology value with the target nucleic acid sequence. This allows the development of oligonucleotides with high specificity.

According to another aspect of the present invention, the present invention provides oligonucleotide sequence data for detecting a target nucleic acid molecule of a source organism of interest, in which the oligonucleotide sequence data is designed using the target nucleic acid sequence data set of the target nucleic acid molecule of the source organism of interest as provided by the methods described in the above Sections 1 to 3.

The oligonucleotide sequence data for detecting the target nucleic acid molecule of the source organism of interest is designed using the target nucleic acid sequence data set of the target nucleic acid molecule of the source organism of interest. The target nucleic acid sequence data set provided by the method of the present invention may cover various variant sequences of the target nucleic acid molecule. Thus, the oligonucleotide sequence data designed on the target nucleic acid sequence data set may have a high coverage of the corresponding target nucleic acid molecule.

Designing the oligonucleotide sequence data for detecting the target nucleic acid molecule of the source organism of interest means that oligonucleotide sequence data which may be used to produce an oligonucleotide for detection of the target nucleic acid molecule of the source organism of interest, is determined. Specifically, designing the oligonucleotide sequence data for detecting a target nucleic acid molecule of a source organism of interest involves identifying nucleic acid sequences complementary to the target nucleic acid sequence of the source organism of interest and determining a portion of the identified nucleic acid sequences as the oligonucleotide sequence data.

According to another aspect of the present invention, the present invention provides a method for providing an oligonucleotide for detecting a target nucleic acid molecule of a source organism of interest, wherein the method comprises synthesizing an oligonucleotide, wherein the oligonucleotide is complementary to the target nucleic acid sequence data included in the target nucleic acid sequence data set provided by the methods described in Section I to Section III, and wherein the oligonucleotide is non-complementary to the nucleic acid sequence data included in the exclusive nucleic acid sequence data set provided by the method described in Section III.

The method for providing the oligonucleotide for the detection of a target nucleic acid molecule of a source organism of interest includes a step of synthesizing the oligonucleotide, wherein the oligonucleotide includes a oligonucleotide sequence, in which the oligonucleotide sequence is complementary to the target nucleic acid sequence data of a target nucleic acid molecule of a source organism of interest and is non-complementary to the nucleic acid sequence data included in the exclusive nucleic acid sequence data set. The synthesizing of the oligonucleotide may be performed by known oligonucleotide synthesizing methods, and additionally, a marker may be attached to the oligonucleotide by known marker attachment methods.

The target nucleic acid sequence data set provided by the method described in Section I to section III of the present invention may cover various variant sequences of the target nucleic acid molecule. Further, the exclusive nucleic acid sequence data set provided by the method described in Section III broadly includes non-target nucleic acid sequences whose the partial region has a high homology with the target nucleic acid sequence. Therefore, when the oligonucleotides for detection of target nucleic acid molecules are prepared by the preparation method of the present invention, the oligonucleotides may have a board coverage relative to the target nucleic acid molecule, and at the same time, may have a high specificity to the target nucleic acid molecule.

IV. Providing Method of EXseq Data Set of Target Nucleic Acid Molecule of Source Organism of Interest The method of the present invention may provide the EXseq data set as an additional nucleic acid sequence data set, as described in Section III, which the conventional design program of oligonucleotide for detection of the target nucleic acid molecule may not provide. The EXseq data set may be provided independently without involving the keyword-based target nucleic acid sequence data set retrieval step. The EXseq data set provided in this way may be used in the conventional design program or method of oligonucleotide for detection of the target nucleic acid molecules, thereby eliminating the risk of designing an oligonucleotide exhibiting the false positive. Thus, present Section IV provides the providing method of the EXseq data set of the target nucleic acid molecule of the source organism of interest.

According to another aspect of the present invention, the present invention may provide a computer-implemented method for providing an exclusive nucleic acid sequence data set of a target nucleic acid molecule of a source organism of interest, the method comprising:

(a) receiving target nucleic acid sequence data of a target nucleic acid molecule;

(b) retrieving at least one nucleic acid sequence data having a homology with the target nucleic acid sequence data at a fourth predefined homology value or greater, and information about a source organism thereof;

(c) selecting at least one nucleic acid sequence data of a source organism not included in the source organism of interest by comparing the retrieved source organism information of the nucleic acid sequence data with the source organism of interest;

(d) for each of the at least one nucleic acid sequence data selected in the step (c), analyzing partial homology between (i) partial regions of a predefined length of each of the nucleic acid sequence data selected in the step (c) and (ii) the target nucleic acid sequence data, and selecting at least one nucleic acid sequence data comprising a partial region having partial homology with the target nucleic acid sequence data at a fifth predefined homology value or greater as the results of analyzing the partial homology among the at least one nucleic acid sequence data selected in the step (c); and (e) providing an exclusive nucleic acid sequence data set including the at least one nucleic acid sequence data selected in the step (d).

The detailed description of the method on a step basis is as follows:

Step (a): Receiving Target Nucleic Acid Sequence Data of Target Nucleic Acid Molecule In the step (a), the target nucleic acid sequence data of the target nucleic acid molecule is received. The target nucleic acid molecule and target nucleic acid sequence data are as described in Section I.

The target nucleic acid sequence data may be inputted directly into the memory or storage device of the computer by the user. Alternatively, the target nucleic acid sequence data may be received by selectively transmitting portions of the nucleic acid sequence data stored in a separate memory or storage device. For example, the processor may selectively receive target nucleic acid sequence data (for example, representative sequence) from a memory or storage device storing a pre-retrieved target nucleic acid sequence data set. Alternatively, a search from the gene database may be executed to receive the target nucleic acid sequence data of the target nucleic acid molecule.

The received target nucleic acid sequence data may be at least one target nucleic acid sequence data. If the received target nucleic acid sequence data is at least one target nucleic acid sequence data, the processor may determine the representative sequence according to the representative sequence determination method described in section 2-1 and may execute following steps using the representative sequence as the target nucleic acid sequence data. If the representative sequence includes plural representative sequences, following steps may be performed for each representative sequence.

Step (b): Retrieving at Least One Nucleic Acid Sequence Data Having a Homology with the Target Nucleic Acid Sequence Data at a Fourth Predefined Homology Value or Greater, and Information about a Source Organism Thereof The step (b) may retrieve at least one nucleic acid sequence data having a homology with the target nucleic acid sequence data at a fourth predefined homology value or greater, and information about a source organism thereof.

This step may be performed according to a nucleic acid sequence data retrieval scheme for providing an additional nucleic acid sequence data set in the step (e) described in section I.

As used herein, in order to differentiate "the predefined homology value" of the step (b) from "other predefined homology values", the former may be referred to as "the fourth predefined homology value". The homology value above or equal to the fourth predefined homology value may be at least 40%, 50%, 60%, 70%, 80%, 90% homology value or greater. The fourth predefined homology value may be in a certain range of values, for example, in a range of 40% to 100%, 50% to 100%, 60% to 100%, 70% to 100%, 80% to 100% or 90% to 100% but is not limited thereto.

The homology is as described in section II. The retrieval operation may be performed by retrieving a sequence meeting the condition from the second database using software (for example, BLAST) known in the art.

Step (c): Selecting at Least One Nucleic Acid Sequence Data of a Source Organism not Included in the Source Organism of Interest by Comparing the Retrieved Source Organism Information of the Nucleic Acid Sequence Data with the Source Organism of Interest The step (c) may select nucleic acid sequence data of a source organism not included in the source organism of interest among the retrieved nucleic acid sequence data.

Selecting the nucleic acid sequence data of a source organism that is not included in the source organism of interest may be done by selecting a nucleic acid sequence data whose source organism information of the retrieved nucleic acid sequence data is free of the name of the source organism of interest, or a synonym thereof, or a name of a source organism belonging to a subclass of the source organism of interest in terms of classification, or a synonym thereof.

Step (d): For Each of the at Least One Nucleic Acid Sequence Data Selected in the Step (c), Analyzing Partial Homology Between (i) Partial Regions of a Predefined Length of Each of the Nucleic Acid Sequence Data Selected in the Step (c), and (ii) the Target Nucleic Acid Sequence Data, and Selecting at Least One Nucleic Acid Sequence Data Comprising a Partial Region Having Partial Homology with the Target Nucleic Acid Sequence Data at a Fifth Predefined Homology Value or Greater Among the at Least One Nucleic Acid Sequence Data Selected in the Step (c)

The step (d) may analyze partial homology of the nucleic acid sequence data of the source organism not included in the source organism of interest and select the nucleic acid sequence data whose partial homology is above or equal to the fifth predefined homology value.

As used herein, to distinguish "the predefined homology value" of the step (d) from "other predefined homology values", the former may be referred to as "the fifth predefined homology value".

The description of the partial region is the same as described for partial region in section 3-2. The predefined length may be, for example, in a range of between 10 nt to 300 nt, 10 nt to 200 nt, 10 nt to 100 nt, 20 nt to 100 nt, 30 nt to 100 nt, 40 nt to 100 nt or 50 nt to 100 nt.

The partial homology analysis is the same as determining the essential EXseq from the EXseq as described in section 3-2. The partial homology refers to the homology between the partial region of the nucleic acid sequence data and a portion of the target nucleic acid sequence data corresponding to the partial region.

The partial region whose the partial homology is greater than or equal to the 5th predefined homology value based on the partial homology analysis result refers to a partial region of the nucleic acid sequence data whose homology value with the portion of the target nucleic acid sequence data corresponding to the partial region is 80%, 90%, 91%, 92%, 93%, 94%, 95%, 96% or 97% or greater.

Step (e): Providing an Exclusive Nucleic Acid Sequence Data Set Including the at Least One Nucleic Acid Sequence Data Selected in the Step (d)

The step (e) may provide an exclusive nucleic acid sequence data set including the at least one nucleic acid sequence data selected in the step (d).

The providing of the target nucleic acid sequence data set may be performed by a known data providing scheme. For example, an output device or a display device may be used to expose content of the data to the user such that the user directly recognizes the data. Alternatively, the data may be provided to the user in such a way that the data is stored by a storing machine in a data storage medium intended by the user. Alternatively, the data may be provided by transmitting the data to a device intended by the user via a network device capable of wired or wireless data transmission.

The exclusive nucleic acid sequence data set includes the nucleic acid sequence data which (i) is not related to the source organism of interest, (ii) has a homology of greater than or equal to the fourth predefined homology value with the target nucleic acid sequence data of the target nucleic acid molecule of the source organism of interest, and (iii) has a partial region whose partial homology is greater than or equal to the fifth predefined homology value with the target nucleic acid sequence data of the target nucleic acid molecule.

Using this method, the exclusive nucleic acid sequence data set of the target nucleic acid molecule of the source organism of interest may be automatically retrieved. Although the exclusive nucleic acid sequence data set is not a target nucleic acid sequence, the exclusive nucleic acid sequence data set may be configured to have the partial region having a high homology with the nucleic acid sequence corresponding to the target nucleic acid molecule of the source organism of interest.

Therefore, the use of the exclusive nucleic acid sequence data set provided by the method of the present invention for the production of oligonucleotides to detect the target nucleic acid molecule of the source organism of interest may lead to the development of oligonucleotides free of the false positive and thus with high specificity.

According to another aspect of the present invention, the present invention provides oligonucleotide sequence data for detecting a target nucleic acid molecule of a source organism of interest, wherein the oligonucleotide sequence data is designed using the exclusive nucleic acid sequence data set of the target nucleic acid molecule of the source organism of interest as provided by the method described in the above Section 4.

The oligonucleotide sequence data for detecting the target nucleic acid molecule of the source organism of interest is designed using the exclusive nucleic acid sequence data set of the target nucleic acid molecule of the source organism of interest. Therefore, when oligonucleotides for detection of target nucleic acid molecules of the source organism of interest are prepared based on the oligonucleotide sequence data, the possibility of false positives is much lower. Thus, this may allow developing of oligonucleotides for detection of target nucleic acid molecules with high specificity.

Designing the oligonucleotide sequence data for detecting the target nucleic acid molecule of the source organism of interest means that determining an oligonucleotide sequence data which may be used to produce an oligonucleotide for detection of the target nucleic acid molecule of the source organism of interest. Specifically, designing the oligonucleotide sequence data for detecting a target nucleic acid molecule of a source organism of interest involves identifying nucleic acid sequences complementary to the target nucleic acid sequence of the source organism of interest and determining a portion of the identified nucleic acid sequences as the oligonucleotide sequence data.

Designing oligonucleotide sequence data for detecting a target nucleic acid molecule using the exclusive nucleic acid sequence data set may involve excluding oligonucleotide sequences that are complementary to the nucleic acid sequence data included in the exclusive nucleic acid sequence data set when determining the oligonucleotide sequence data.

According to another aspect of the present invention, the present invention provides a method for providing an oligonucleotide for detecting a target nucleic acid molecule of a source organism of interest, wherein the method comprises synthesizing the oligonucleotide, wherein the oligonucleotide sequence is complementary to the target nucleic acid sequence data of the target nucleic acid molecule of the source organism of interest, and wherein the oligonucleotide is non-complementary to the nucleic acid sequence data included in the exclusive nucleic acid sequence data set.

The method of the present invention includes synthesizing the oligonucleotide, in which the oligonucleotide includes a oligonucleotide sequence, in which the oligonucleotide sequence is complementary to the target nucleic acid sequence data of the target nucleic acid molecule of the source organism of interest and is non-complementary to the nucleic acid sequence data included in the exclusive nucleic acid sequence data set.

The synthesizing of the oligonucleotide may be performed by known oligonucleotide synthesizing methods, and additionally, a marker may be attached to the oligonucleotide by known marker attachment methods.

Therefore, when the oligonucleotides for detection of target nucleic acid molecules are prepared by the preparation method of the present invention, the oligonucleotides may have a very low possibility of the false positive and, at the same time, may have a high specificity to the target nucleic acid molecule.

V. Storage Medium, Device and Program

According to another aspect of the present invention, the present invention provides a computer-readable storage medium containing instructions stored therein, wherein when the instructions is executed by a computer, the instructions are configured to enable a processor of the computer to perform a method for providing a target nucleic acid sequence data of a target nucleic acid molecule of a source organism of interest, the method comprising: (a) receiving a name of the nucleic acid molecule and a name of the source organism, and automatically retrieving synonyms for the target nucleic acid molecule of the source organism from a first database; (b) retrieving identifiers of nucleic acid records from a second database, wherein each of the nucleic acid records is associated with the source organism and comprises, as a descriptor thereof, at least one selected from the group of the name of the target nucleic acid molecule and the retrieved synonyms; and (c) retrieving nucleic acid sequence data specified by the identifiers to provide a target nucleic acid sequence data set of the target nucleic acid molecule.

According to another aspect of the present invention, the present invention provides a computer program stored in a computer-readable storage medium, wherein when the program is executed by a computer, the program is configured to enable a processor of the computer to perform a method for providing a target nucleic acid sequence data set of a target nucleic acid molecule of a source organism of interest, the method comprising: (a) receiving a name of the nucleic acid molecule and a name of the source organism, and automatically retrieving synonyms for the target nucleic acid molecule of the source organism from a first database; (b) retrieving identifiers of nucleic acid records from a second database, wherein each of the nucleic acid records is associated with the source organism and comprises, as a descriptor thereof, at least one selected from the group of the name of the target nucleic acid molecule and the retrieved synonyms; and (c) retrieving nucleic acid sequence data specified by the identifiers to provide a target nucleic acid sequence data set of the target nucleic acid molecule.

When the program instructions are executed by the processor, the program instructions are configured to enable a processor of the computer to perform the above method. The program instructions for performing the method for providing a target nucleic acid sequence data set of a target nucleic acid molecule of a source organism of interest may include: (i) instructions for receiving a name of the target nucleic acid molecule and a name of the source organism, and automatically retrieving synonyms for the target nucleic acid molecule of the source organism from a first database; (ii) instructions for retrieving identifiers of nucleic acid records from a second database, wherein each of the nucleic acid records is associated with the source organism and comprises, as a descriptor thereof, at least one selected from the group of the name of the target nucleic acid molecule and the retrieved synonyms; and (iii) instructions for retrieving nucleic acid sequence data specified by the identifiers.

The method of the present invention is implemented by the processor. The processor may be embodied as a processor in a stand-alone computer or a processor in a network attached computer. The computer-readable storage medium may include any one of a variety of storage media known in the art such as CD-R, CD-ROM, DVD, flash memory, floppy disk, hard drive, portable HDD, USB, magnetic tape, MINIDISC, non-volatile memory card, EEPROM, optical disk, optical storage media, RAM, ROM, system memory, and web servers, but may not be limited thereto.

The instructions that implement the processor that executes the present invention may be included in the logic system. The instructions may be stored on a software recording medium (e.g., a portable HDD, a USB, a floppy disk, a CD and a DVD). Alternatively, the instructions may be downloadable or may be stored in a memory module (e.g., another memory such as a hard drive or local or attached RAM or ROM). The computer code executing the present invention may also be implemented in a variety of coding languages such as C, C++, Java, Visual Basic, VBScript, JavaScript, Perl, XML, Python, Bash and Next-flow. Further, various languages and protocols may be used for external and internal storage and delivery of data sets and commands according to the present invention.

According to another aspect of the present invention, the present invention provides a device for providing a target nucleic acid sequence data set of a target nucleic acid molecule of a source organism of interest, the device comprising: (a) a computer processor; and (b) the computer-readable storage medium of the present invention coupled to the processor.

According to one embodiment of the present invention, the device of the present invention may additionally include an input device that may receive, from the user, the name of the target nucleic acid molecule and information about the source organism thereof, and a data providing device that may provide the user with the retrieved target nucleic acid sequence data of the target nucleic acid molecule. The data providing device includes an output device, a display device, a storage medium connection or recording device, and a network device capable of transmitting data in a wired or wireless manner.

The computer processor may be configured so that one processor performs all of the above-mentioned performance. Alternatively, the processor unit may be configured to allow each of multiple processors to perform each performance.

According to the present invention, the device receives the name of the target nucleic acid molecule and information about the source organism of the target nucleic acid molecule of a source organism of interest and retrieves synonyms of the target nucleic acid molecule of the source organism. Then, the device retrieves the identifiers of the nucleic acid sequence data of the source organism using the retrieved synonyms. Then, the device retrieves a nucleic acid sequence data that is specified by the retrieved identifiers and then provides a target nucleic acid sequence data set of the target nucleic acid molecule.

The storage medium, device and computer program in accordance with the present invention may be configured to implement the above-described method of the present invention on a computer. The overlapping content between the storage medium, device and computer program will be omitted in order to avoid the excessive complexity of the present disclosure.

Disclosed is a summary of the features and advantages of the present invention:

(a) a Data Coverage Improvement

Designing oligonucleotides that the oligonucleotides can detect various variants of specific pathogens at as high a coverage as possible is a very important factor in the oligonucleotide design for specific pathogen detection. As the nucleic acid sequence data set of the specific gene of the pathogen, provided for the oligonucleotide design, includes more variations of the pathogen, the accuracy of detection using the oligonucleotides designed based on the nucleic acid sequence data set is enhanced. The method of the present invention efficiently and automatically retrieves more synonyms than the synonyms retrieved based on user's experience.

Thus, the target nucleic acid sequence data set of the target nucleic acid molecule retrieved using the larger number of the synonyms may cover various variant sequences of the target nucleic acid molecule. Therefore, the oligonucleotides thus designed have a high coverage of the corresponding target nucleic acid molecule. Such a coverage improvement may be further enhanced by automatically selecting the representative sequence and reinforcing the nucleic acid sequence data set with the homology-based search result using the representative sequence.

(b) Evolved Computer-Based Automatic Sequence Retrieval

The conventional nucleic acid sequence search technique was limited to the computer implemented search of the nucleic acid record based on keywords and of the sequence having a high homology with a specific sequence based on keywords. To the contrary, the technique of providing the target nucleic acid sequence according to the present invention automatically extends the input keyword to provide the high coverage search result. In particular, the sequence of the target nucleic acid molecule of interest is automatically detected, parsed and provided among the sequences included in the nucleic acid record detected by the keyword-based search. This function was not provided in the conventional keyword-based nucleic acid detection system. Thus, this function has the effect of greatly increasing the user's convenience.

Further, the representative sequence is automatically determined based on the retrieved target nucleic acid sequence data, and then, sequence data having a high homology level with the representative sequence is added. Thus, compared with the conventional nucleic acid sequence retrieval method, the target nucleic acid sequences can be more faithfully retrieved in accordance with the present invention.

In other words, the method of the present invention may use (i) automatic expansion of keywords, (ii) automatic extraction of a portion of the target nucleic acid sequence from the searched nucleic acid record; and (iii) reinforcement of nucleic acid sequences via homology-based searches using nucleic acid sequences retrieved by keyword search, thereby to provide an advanced target nucleic acid sequence data set more reliable in terms of coverage than the nucleic acid sequence data set provided by the conventional system, and to provide the system more advanced in terms of ease of use compared to the conventional system.

(c) Improvement in Specificity

The specificity is an important factor in oligonucleotide development for specific target nucleic acid molecule detection. When the probability that nucleic acid molecules having a nucleic acid sequence similar to the target nucleic acid molecule but being different from the target nucleic acid molecule are detected is increased, the probability of false positive errors is increased. Theoretically, the exclusive nucleic acid sequence includes all nucleic acid sequences except for the target nucleic acid sequence. However, an approach in which all of the nucleic acid sequences except for the target nucleic acid sequences are checked for the oligonucleotide development for specific target nucleic acid molecule detection may not be realized. Therefore, conventionally, only the nucleic acid sequences of source organisms similar phylogenetically to the target source organism, and the nucleic acid sequences of similar target nucleic acid molecules to the target nucleic acid molecule as known to the developer are determined as the exclusive nucleic acid sequence data set, which was used to develop oligonucle-otides for target nucleic acid molecule detection.

However, this conventional method has a problem in that the coverage of the exclusive nucleic acid sequence data set is insufficient, so that the probability of detection signal occurrence resulting from the nucleic acid sequence other than the target nucleic acid sequence may not be eliminated, on other words, not to eliminate the possibility of false positives.

The exclusive nucleic acid sequence data set provided by the method of the present invention may include all of sequences whose partial region has a minimal homology with the representative nucleic acid sequence as the target nucleic acid sequence. Thus, all of the essential exclusive nucleic acid sequences, which must be analyzed can be selected. Therefore, when using the exclusive nucleic acid sequence or the essential exclusive nucleic acid sequence data set provided by the method of the present invention, development of oligonucleotides with high specificity which are far less likely to cause the false positives is possible.

The present disclosure will describe the present invention in more detail with refence to the Present Examples. These Present Examples are intended solely to describe the present invention in more detail. It will be obvious to those of ordinary skill in the art to which the present invention belongs that the scope of the present invention in accordance with the principles of the present invention is not limited by these Present Examples.

EXAMPLES

Example 1: AutoMSA System

The method of the present invention is implemented by Seegene's AutoMSA system. As shown in FIG. 2, the system implementing the present invention receives the name of the target nucleic acid molecule and information about the source organism of the target nucleic acid molecule from the user and automatically performs the synonym retrieval, identifier retrieval, gene record retrieval and target nucleic acid sequence data parsing steps. Thus, the system provides the target nucleic acid sequence data set.

All these steps are done automatically. In other words, from the viewpoint of the user, actually, the user may only conduct the step of inputting the minimum essential infor-mation such as the name of the target nucleic acid molecule and the information about the source organism of the target nucleic acid molecule and the step of viewing the final product.

Therefore, in the following Examples, in order to show that each step is proceeding according to the method of the present invention, visualization of data provided at each step is performed while arbitrarily retrieving data provided at each step.

Example 2: Providing Target Nucleic Acid Sequence Data Set Using Synonym Retrieval <2-1> Synonym Retrieval The synonyms were automatically retrieved from the gene database by inputting the name of the specific target nucleic acid molecule and source organism name of the specific target nucleic acid molecule.

For each of the five organisms, one gene was determined as a target. The synonyms were retrieved by inputting the target gene. The gene database used for the synonym retrieval in the AutoMSA system is the NCBI gene database.

The results of synonym retrieval are shown in Table 1. When there is no search result, only the input target name is retrieved as a synonym. As shown in FIG. 3 and Table 1, we confirmed the retrieval of the synonyms associated with the corresponding target nucleic acid molecule.

TABLE 1

| Number | Organism | Target | Retrieved synonym |
|---|---|---|---|
| 1 | *Gardnerella vaginalis* (txid: 2702) | tuf | HMPREF0421_20480 translation elongation factor Tu tuf gene translationelogationfactorTu tuf protein tuf |
| 2 | *Lactobacillus jensenii* (txid: 47770) | cpn60 | cpn60 gene hsp60 cpn60 cpn60 protein |
| 3 | *Lactobacillus gasseri* (txid: 1596) | rpoA | rpoA gene rpoA rpoA protein |
| 4 | *Candida albicans* (txid: 5476) | PHR1 | CAALFM_C404530CA, Ca019.3829 CAALFM_C404530CA, Ca019.3829 PHR1 protein PHR1 PHR1 gene |
| 5 | *Candida glabrata* (txid: 5478) | 40S ribosomal protein S0 | 40S ribosomal protein s0 protein 40S ribosomal protein s0 40S ribosomal protein s0 gene |

<2-2> Retrieval of Identifier of Nucleic Acid Sequence Data Using Synonym

Identifiers of related sequences are automatically retrieved from the nucleotide database using the retrieved synonyms of the five targets. A query using the retrieved synonyms is automatically created and transmitted to the NCBI GenBank, and thus the related identifier as searched is returned as the result value. Specific queries as generated automatically and transmitted to the nucleotide database are as described in Table 2.

As in the search result of Table 2, it was evaluated that the identifiers of related sequences were retrieved. The nucleo-tide database of NCBI was used as the database as used. The retrieved sequence information file is Genbank record full report.

TABLE 2

| Number | Organism, Target and Query | result |
|---|---|---|
| 1 | Organism: *Gardnerella vaginalis* (txid: 2702) Target: tuf Query: (HMPREF0421_20480[gene] OR HMPREF0421_20480[protein] OR HMPREF0421_20480[title] OR HMPREF0421_20480[keyword] OR translation elongation factor Tu[gene] OR translation elongation factor Tu[protein] OR translation elongation factor Tu[title] OR translation elongation factor Tu[keyword] OR tuf gene[gene] OR tuf gene[protein] OR tuf gene[title] OR tuf gene[keyword] OR translationelongationfactorTu[gene] OR translationelongationfactorTu[protein] OR translationelongationfactorTu[title] OR translationelongationfactorTu[keyword] | 71 |

TABLE 2-continued

| Num-ber | Organism, Target and Query | result |
|---|---|---|
| | OR tuf protein[gene] OR tuf protein[protein] OR tuf protein[title] OR tuf protein[keyword] OR tuf[gene] OR tuf[protein] OR tuf[title] OR tuf[keyword]) AND txid2702[Organism:exp] | |
| 2 | Organism: *Lactobacillus jensenii* (txid: 47770\| 109790) Target: cpn60 Query: (cpn60 gene[gene] OR cpn60 gene[protein] OR cpn60 gene[title] OR cpn60 gene[keyword] OR hsp60[gene] OR hsp60[protein] OR hsp60[title] OR hsp60[keyword] OR cpn60[gene] OR cpn60[protein] OR cpn60[title] OR cpn60[ keyword] OR cpn60 protein[gene] OR cpn60 protein[protein] OR cpn60 protein[title] OR cpn60 protein[keyword]) AND (txid47770[Organism:exp] OR txid109790[Organism:exp]) | 12 |
| 3 | Organism: *Lactobacillus gasseri* (txid: 1596) Target: rpoA Query: (rpoA gene[gene] OR rpoA gene[protein] OR rpoA gene[title] OR rpoA gene[keyword] OR rpoA[gene] OR rpoA[protein] OR rpoA[title] OR rpoA[keyword] OR rpoA protein[gene] OR rpoA protein[protein] OR rpoA protein[title] OR rpoA protein[keyword]) AND txid1596[Organism:exp] | 12 |
| 4 | Organism: *Candida albicans* (txid: 5476) Target: PHR1 Query: ((Phr1p[gene] OR Phr1p[protein] OR Phr1p[title] OR Phr1p[keyword] OR CAALFM_C404530CA, Ca019.3829[gene] OR CAALFM_C404530CA, Ca019.3829[protein] OR CAALFM_C404530CA, CaO19.3829[title] OR CAALFM_C404530CA, CaO19.3829[keyword] OR CAALFM_C404530CA,Ca019.3829[gene] OR CAALFM_C404530CA,CaO19.3829[protein] OR CAALFM_C404530CA,Ca019.3829[title] OR CAALFM_C404530CA,CaO19.3829[keyword] OR PHR1 protein[gene] OR PHR1 protein[protein] OR PHR1 protein[title] OR PHR1 protein[keyword] OR PHR1[gene] OR PHR1[protein] OR PHR1[title] OR PHR1[keyword] OR PHR1 gene[gene] OR PHR1 gene[protein] OR PHR1 gene[title] OR PHR1 gene[keyword]) AND txid5476[Organism:exp] | 6 |
| 5 | Organism: *Candida glabrata* (txid: 5478) Target: 40S ribosomal protein S0 Query: ((40S ribosomal protein S0 protein[gene] OR 40S ribosomal protein S0 protein[protein] OR 40S ribosomal protein S0 protein[title] OR 40S ribosomal protein S0 protein[keyword] OR 40S ribosomal protein S0O[gene] OR 40S ribosomal protein S0[protein] OR 40S ribosomal protein S0[title] OR 40S ribosomal protein S0[keyword] OR 40S ribosomal protein S0 gene[gene] OR 40S ribosomal protein S0 gene[protein] OR 40S ribosomal protein S0 gene[title] OR 40S ribosomal protein S0 gene[keyword]) AND txid5478[Organism:exp] | 10 |

<2-3> Providing Target Nucleic Acid Sequence Data Set of Target Nucleic Acid Molecule Using Retrieval and Parsing of Nucleic Acid Record Specified by Identifiers The retrieved identifier was used to retrieve the nucleic acid sequence data. The nucleic acid records (Genbank record) corresponding to each identifier were retrieved using the identifier information stored in the memory or file.

The nucleic acid sequence data corresponding to the target nucleic acid molecule was retrieved from the retrieved nucleic acid record.

The AutoMSA system recognizes, from the previously retrieved nucleic acid record, a portion of the sequence wherein the name of the target nucleic acid sequence or synonym thereof is recorded in the gene, product, or note field of the portion of the sequence and selectively retrieved only the corresponding portion of the nucleic acid sequence.

FIG. 4 shows the result of recognition of tuf gene portion and retrieval of corresponding sequences (SEQ ID NO: 1) from a single nucleic acid record (*Gardnerella vaginalis* 41V GV41V_c00024, whole genome shotgun sequence) searched using information on the tuf gene of *Gardnerella vaginalis* (txid: 2702).

Although not a final product in the program, the retrieved sequence was displayed on the display for evaluation. The retrieved sequence was compared with a result from the manual evaluation about which portion of the nucleic acid record of the actual nucleotide database was retrieved.

As shown in FIG. 4C, the AutoMSA system recognizes the tuf portion in the nucleic acid record information and provides the nucleic acid sequence data (SEQ ID NO: 2) corresponding to tuf portion which is the target nucleic acid molecule. As shown in FIGS. 4A-4C, it was evaluated that the nucleic acid sequence data provided from AutoMSA system matches a manual result by the researcher directly accessing the nucleotide database.

Figures 5A, 5B:
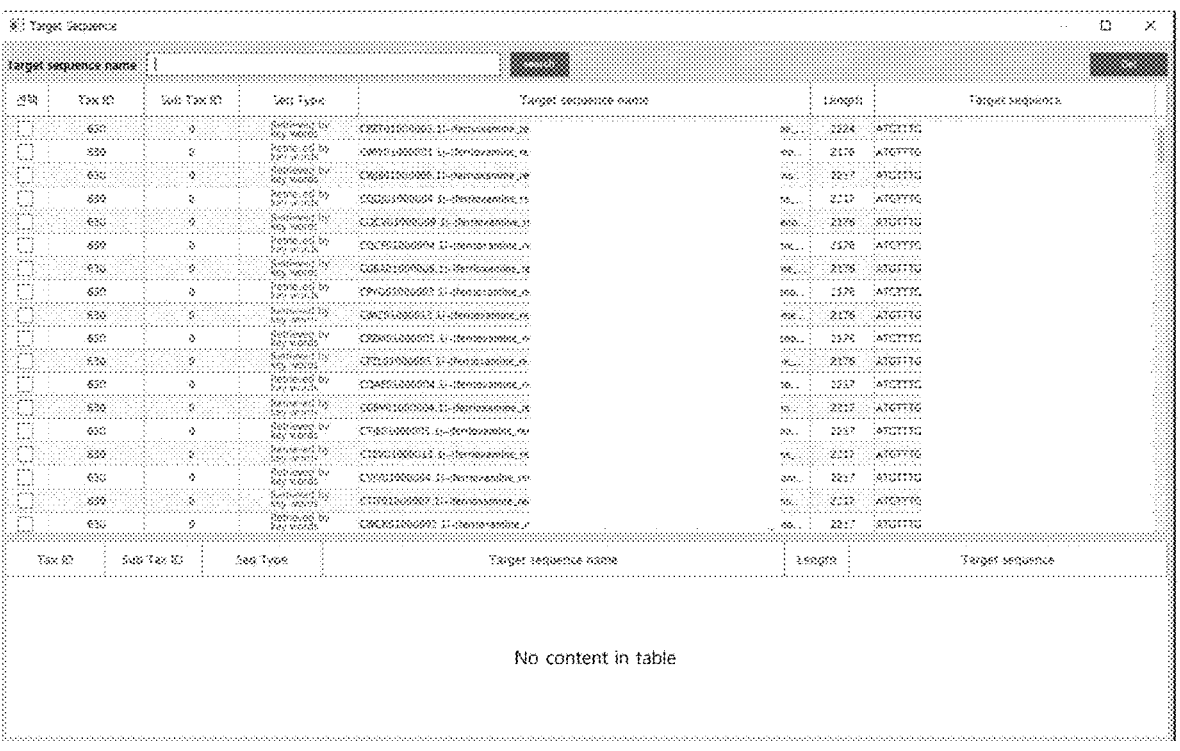
FIG. 5A shows the display on the AutoMSA system of the results of retrieval of the target nucleic acid sequence data set according to the method of the present invention.
FIG. 5B shows the results of the retrieval and alignment of the first target nucleic acid sequence data set and the second target nucleic acid sequence data set according to the method of the present invention (SEQ ID NOs: 3-16). The gray shaded data refers to the second target nucleic acid sequence data further retrieved using the representative sequence.

The AutoMAS system repeatedly performed the above operations for 71 cases retrieved while targeting the tuf gene of *Gardnerella vaginalis* (txid: 2702) in Example <2-2>, thereby to retrieve the target nucleic acid sequence data set. Therefore, the target nucleic acid sequence data set was provided as shown in FIG. 5A.

Example 3: Retrieval and Generation of Extended Target Nucleic Acid Sequence Data Set and Exclusive Nucleic Acid Sequence Data Set <3-1> Representative Sequence Retrieval The target nucleic acid sequences of the five target nucleic acid molecules previously retrieved were classified based on the homology. The representative sequence was selected. Representative sequence selection was performed by classifying the retrieved target nucleic acid sequences and determining the representative sequence using UCLUST algorithm. The homology criterion for the classification of the target nucleic acid sequence and for selecting the representative sequence was 90%.

As a result, as shown in Table 3 and FIG. 7, each of *Gardnerella vaginalis* and *Lactobacillus jensenii* was classified into two groups, and, thus, two representative sequences were selected for each of *Gardnerella vaginalis* and *Lactobacillus jensenii*. One representative sequence was selected for each of remaining genes.

TABLE 3

| Num-ber | Organism | Target | Number of groups | Representative sequence ID |
|---|---|---|---|---|
| 1 | *Gardnerella vaginalis* (txid: 2702) | tuf | 2 | PKJJ01000001.1 PNGN01000013.1 |

TABLE 3-continued

| Num-ber | Organism | Target | Number of groups | Representative sequence ID |
|---|---|---|---|---|
| 2 | *Lactobacillus jensenii* (txid: 47770) | cpn60 | 2 | FR775916.1 |
| | | | | FR775912.1 |
| 3 | *Lactobacillus gasseri* (txid: 1596) | rpoA | 1 | GL379581.1 |
| 4 | *Candida albicans* (txid: 5476) | PHR1 | 1 | AF247189.1 |
| 5 | *Candida glabrata* (txid: 5478) | 40S ribosomal protein S0 | 1 | FWDN01000041.1 |

<3-2> Retrieval of Second Target Nucleic Acid Sequence Data and Provision of Extended Target Nucleic Acid Sequence Data Set Using the determined representative sequences, the system retrieved the second target nucleic acid sequence data as the additional nucleic acid sequence data set.

The second target nucleic acid sequence data was retrieved based on the homology with the representative sequence. The AutoMSA system automatically compared the determined representative sequence with the GenBank database and retrieved nucleic acid sequence data with a homology of greater than or equal to the homology reference value. The homology reference value was determined to be 90% identity.

From a result of retrieving the second target nucleic acid sequence data in the same way, it was evaluated that target nucleic acid sequences that were not retrieved using the synonym extension was additionally retrieved as shown in Table 4 and FIG. 8.

TABLE 4

| Num-ber | Organism | Target | Number of added sequences |
|---|---|---|---|
| 1 | *Gardnerella vaginalis* (txid: 2702) | tuf | 2 |
| 2 | *Lactobacillus jensenii* (txid: 47770) | cpn60 | 2 |
| 3 | *Lactobacillus gasseri* (txid: 1596) | rpoA | 1 |
| 4 | *Candida albicans* (txid: 5476) | PHR1 | 0 |
| 5 | *Candida glabrata* (txid: 5478) | 40S ribosomal protein S0 | 1 |

Further, as shown in FIG. 5B, we confirmed that the first target nucleic acid sequence data set, and second target nucleic acid sequence data set were combined to provide the extended target nucleic acid sequence data set (SEQ ID NOs: 3-16) of the target nucleic acid molecule. In FIG. 5B, the gray shaded sequence refers to the second target nucleic acid sequence data as added. We confirmed that the target nucleic acid sequences were mostly retrieved using the keyword search extended by synonym, and the missing sequences were supplemented in the additional retrieval step using the representative sequence.

Example 4: Retrieval and Generation of Exclusive Nucleic Acid Sequence Data Set

<4-1> Exclusive Nucleic Acid Sequence Data Retrieval

EXseqs of each target nucleic acid molecule were retrieved in addition to the provided extended target nucleic acid sequence data set.

For each target, BLAST search was performed using the representative sequence determined in Example <3-1> to retrieve the similar nucleic acid sequences. Then, the nucleic acid sequence data not related to each target nucleic acid sequence in terms of the Taxonomic ID were retrieved. The homology reference value as used is 50%. The number of target-specific retrieved EXseqs in this way is shown in Table 5.

TABLE 5

| Number | Organism | Target | Number of retrieved exclusive nucleic acid sequence |
|---|---|---|---|
| 1 | *Gardnerella vaginalis* (txid: 2702) | tuf | 1123 |
| 2 | *Lactobacillus jensenii* (txid: 47770) | cpn60 | 1126 |
| 3 | *Lactobacillus gasseri* (txid: 1596) | rpoA | 23 |
| 4 | *Candida albicans* (txid: 5476) | PHR1 | 4 |
| 5 | *Candida glabrata* (txid: 5478) | 40S ribosomal protein S0 | 354 |

<4-2> Selection of Essential Exclusive Nucleic Acid Sequence

In order to retrieve the essential EXseq data, the system first determined the matching region of each of the retrieved EXseqs retrieved in Example <4-1>. When alignment between EXseq and representative sequence was analyzed, the matching region refers to a region occupied by the nucleotides of EXseq whose matching or mismatching with the nucleotide of the representative sequence is analyzed. The matching region of the EXseq has the same length as the representative sequence.

Next, in the matching region of the EXseqs retrieved in Example <4-1>, the nucleic acid sequence from the first nucleotide (1st nt) to 100th nt was designated as the first EX-template. The AutoMSA system determined whether the first EX-template has a homology of greater than or equal to 90% with respect to the representative sequence retrieved in Example <3-1>. The nucleic acid sequence from the 2 nt to the 101th nt in the matching region of the EXseq was set as the second EX-template. The same operation was repeated. In this way, the EX-template was sequentially set in a sliding manner in a unit of 1 nt and was subjected to homology analysis with the representative sequence, thereby to select EXseq having the EX-template having the homology value of 90% or greater.

In the next step, the homology between the representative sequence and the matching regions of the selected EXseq was analyzed. EXseqs having the matching regions having the homology value of 70% or greater were selected and provided as essential EXSEq.

As a result, as shown in FIG. 11, by the AutoMSA system, target nucleic acid sequences which are not associated with the target nucleic acid molecule for each target, and have the homology value of the predefined homology value or greater with the target nucleic acid sequence and have the partial regions having the very high homology with the target nucleic acid sequence were defined and retrieved as the essential EXseq. The number of target-specific retrieved essential EXseqs is shown in Table 6.

The retrieved nucleic acid sequences are nucleic acid sequences that are likely to cause false positive results by hybridizing with a primer or a probe for detecting a target nucleic acid molecule. Thus, the retrieved nucleic acid sequences should be carefully examined when designing oligonucleotides for detection of target nucleic acid molecules. Therefore, selectively retrieving and providing these sequences may be very helpful to improve specificity of the oligonucleotides when designing oligonucleotides for detection of target nucleic acid molecules.

TABLE 6

| Number | Organism | Target | Number of retrieved essential exclusive nucleic acid sequences |
|---|---|---|---|
| 1 | *Gardnerella vaginalis* (txid: 2702) | tuf | 1104 |
| 2 | *Lactobacillus jensenii* (txid: 47770) | cpn60 | 1126 |
| 3 | *Lactobacillus gasseri* (txid: 1596) | rpoA | 23 |
| 4 | *Candida albicans* (txid: 5476) | PHR1 | 4 |
| 5 | *Candida glabrata* (txid: 5478) | 40S ribosomal protein S0 | 351 |

Figure 12:
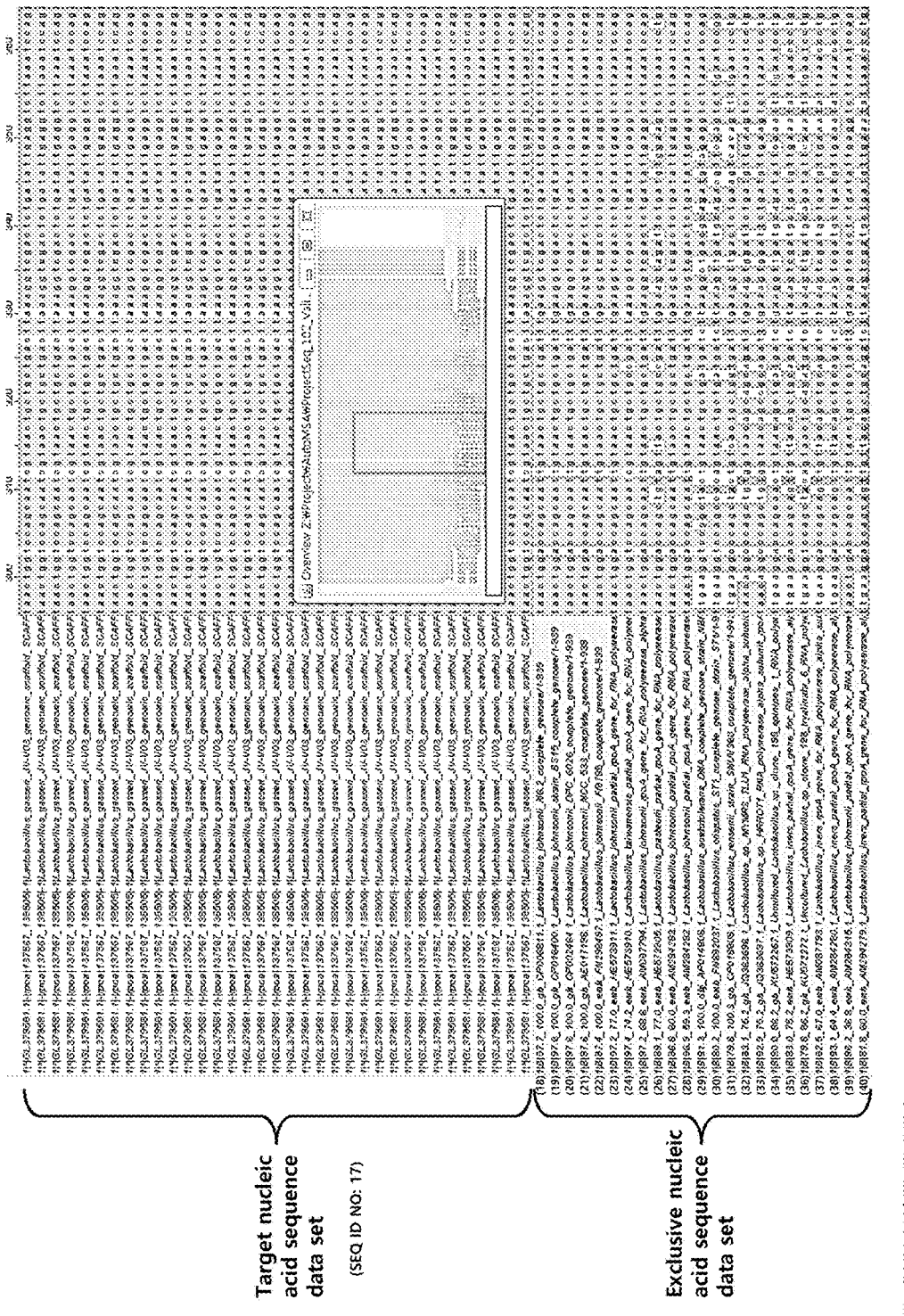
FIG. 12 shows the alignment results of the total nucleic acid sequence data set (SEQ ID NO: 17) including the extended target nucleic acid sequence data set and the exclusive nucleic acid sequence data set (SEQ ID NOs: 18-40) of the present invention.

Finally, the total nucleic acid sequence data set was obtained by combining the retrieved essential EXseq and the extended target nucleic acid sequence data set retrieved in Example <3-2>, and the alignment of the total nucleic acid sequence data set was performed. FIG. 12 shows the result of alignment of the obtained total nucleic acid sequence data set of rpoA of *Lactobacillus gasseri* (SEQ ID NOs: 17-40).

Thus, the method of the present invention easily provides all the sequence information necessary for the design of oligonucleotides such as probes and primers for target detection. While having described specific portions of the present invention in detail, those skilled in the art will appreciate that these specific portions are merely preferred embodiments. The scope of the present invention is not limited to the specific portions. Accordingly, the actual scope of the present invention will be defined by the appended claims and their equivalents.

What is claimed is:

1. A method for providing an oligonucleotide for detecting a target nucleic acid molecule of a source organism of interest, the method comprising:

(a) receiving a name of the nucleic acid molecule and a name of the source organism, and automatically retrieving synonyms for the target nucleic acid molecule of the source organism from a first database;

(b) retrieving identifiers of nucleic acid records from a second database, wherein each of the nucleic acid records is associated with the source organism and comprises, as a descriptor thereof, at least one selected from the group of the name of the target nucleic acid molecule and the retrieved synonyms;

(c) retrieving nucleic acid sequence data specified by the identifiers to provide a target nucleic acid sequence data set of the target nucleic acid molecule, wherein the target nucleic acid sequence data set of the target nucleic acid molecule retrieved in the step (c) is a first target nucleic acid sequence data set;

(d) determining a representative sequence from the retrieved first target nucleic acid sequence data set; and (e) retrieving, from the second database, nucleic acid sequence data having homology with the representative sequence at a predefined homology value or greater, and further providing an additional nucleic acid sequence data set, wherein the additional nucleic acid sequence data set provided in the step (e) is provided by following sub-steps (e1) and (e2):

(e1) retrieving, from the second database, nucleic acid sequence data having a homology with the representative sequence at a first predefined homology value or greater and associated with the received source organism, thereby obtaining a second target nucleic acid sequence data set, and, then, providing an additional nucleic acid sequence data set including the second target nucleic acid sequence data set; and (e2) retrieving, from the second database, nucleic acid sequence data having a homology with the representative sequence at a second predefined homology value or greater and non-associated with the received source organism, thereby obtaining an exclusive target nucleic acid sequence data set, and, then, providing an additional nucleic acid sequence data set including the exclusive target nucleic acid sequence data set;

(f) providing synthesizing the retrieved nucleic acid sequence data and an alignment result between the retrieved nucleic acid sequence data as a sequence information for the design of the oligonucleotides used to detect a target nucleic acid molecule of a source organism of interest; and (g) synthesizing the oligonucleotide comprising an oligonucleotide sequence that is complementary to the target nucleic acid sequence data of a target nucleic acid molecule of a source organism of interest and non-complementary to the nucleic acid sequence data included in the exclusive nucleic acid sequence data set.

2. The method of claim 1, wherein the target nucleic acid sequence data set comprises nucleic acid sequence data corresponding to a portion or entirety of the target nucleic acid molecule or nucleic acid variant sequence data of the target nucleic acid molecule.

3. The method of claim 1, wherein the first database is configured to provide genetic information of an organism including a title of a nucleic acid molecule, a name of a nucleic acid molecule, description of a nucleic acid molecule, a source organism name, and a name of a protein encoded by a nucleic acid molecule.

4. The method of claim 1, wherein the second database is configured to provide a nucleic acid record containing nucleic acid sequence data, and an identifier and a descriptor about the nucleic acid sequence data.

5. The method of claim 1, wherein the step (c) comprises selectively retrieving nucleic acid sequence data corresponding to the target nucleic acid molecule from nucleic acid sequence data specified by the identifiers and providing the target nucleic acid sequence data set of the target nucleic acid molecule.

6. The method of claim 1, wherein the step (c) comprises:

(c1) retrieving nucleic acid records specified by the identifiers; and (c2) retrieving nucleic acid sequence data corresponding to the target nucleic acid molecule from each of the nucleic acid records and providing the target nucleic acid sequence data set of the target nucleic acid molecule.

7. The method of claim 6, wherein the step (c2) comprises selectively retrieving the nucleic acid sequence data corresponding to the target nucleic acid molecule and identification information about the nucleic acid sequence data from each of the nucleic acid records, and providing the target nucleic acid sequence data set of the target nucleic acid molecule;

wherein the selectively retrieving the nucleic acid sequence data and the identification information thereof comprises:

(c21) determining a valid sub-record among at least one sub-record in each of the nucleic acid records, wherein the synonyms are recorded in a pre-defined first specification in the valid sub-record;

(c22) upon determination there is no valid sub-record determined by the first specification among the at least one sub-record in each of the nucleic acid records, determining a valid sub-record among the at least one sub-record in each of the nucleic acid records, wherein the synonyms are recorded in a pre-defined second specification in the valid sub-record;

(c23) upon determination there is no valid sub-record determined by the second specification among the at least one sub-record in each of the nucleic acid records, determining a valid sub-record among the at least one sub-record in each of the nucleic acid records, wherein the synonyms are recorded in a pre-defined third specification in the valid sub-record; and (c24) retrieving nucleic acid sequence data corresponding to the determined valid sub-record and identification information thereof.

8. The method of claim 1, wherein the step (e2) comprises:

retrieving, from the second database, partial nucleic acid sequence data having a homology with a partial region of the representative sequence at a third predefined homology value or greater, wherein the partial nucleic acid sequence data is contained as a partial region of the nucleic acid sequence data having a homology with the representative sequence at the second predefined homology value or greater and non-associated with the received source organism;

obtaining an exclusive target nucleic acid sequence data set containing the partial nucleic acid sequence data; and providing an additional nucleic acid sequence data set including the exclusive target nucleic acid sequence data set.

* * * * *

SEQUENCE LISTING

```
<160> NUMBER OF SEQ ID NOS: 40

<210> SEQ ID NO 1
<211> LENGTH: 1200
<212> TYPE: DNA
<213> ORGANISM: Gardnerella vaginalis

<400> SEQUENCE: 1
ctaggcaaga atcttggtca cacgaccaga accaacggta cggccacctt cacgaactgc      60
gaaggtcaag ccctcttcca ttgcgatagc ctggatcaac tcaacagtga aggttgcgtg     120
atcgcctggc tgaaccattt cgatgccttc tggcaaggtg ataacgccag taacatcggt     180
ggtacggaag tagaactgtg gacggtagtt ggagaagaat ggcgagtgac ggccaccttc     240
atccttggtc aagacgtaaa cttcgccttc gaacttggtg tgtggagtca cagaacctgg     300
agcagccaca acctgaccac gctcaacgtc ggtacggttg ataccacgga gaagaagacc     360
agtgttatcg ccagcctcgg cctcatccat ctgcttgtgg aaggtctcga tagaggtgac     420
ggtggtggtc tgggtatcac gcaaaccaac aatctcaact ggggtgttga ttgggagctt     480
accacgctca acacgaccgg tgacaacggt accacgaccg gagatggtga acacatcttc     540
gattggcatc aagaatggct tgtcaagatc gtgagttggg gttggaatgt actcgtcaac     600
agccttcatg agttccttga cggtctctac ccacttgtcg tggtctggag cgtcatcatg     660
caaagcgccg taagcggaag tacggatgac tgggcaatcg cgatcgaagc cgttttcttc     720
gaggaggtca cgaacctctt cttcaacgag gtcgataagc tcttcgtcgt caaccatatc     780
gcacttgttc aaagcaacaa gaatttttgg aacgccgacc tgcttagcaa gcaagacgtg     840
ttcacgggtc tgagccattg gaccgtcggt agcagcaacc acgaggattg cgccatccat     900
ctgagcggca ccagtgatca tgttcttaac gtaatcagcg tggcctggag cgtccacgtg     960
agcatagtgg cgtgcagccg tctgatactc gatgtgggcg atgttaatgg taatgccgcg    1020
ctccttctct tctggagcgg cgtcgatctg atcgaagtca tactgagggt tcagatctgg    1080
atactcgcca tgcagcacct tagaaatagc cgcggtcaag gtagtcttac cgtgatcaac    1140
gtgaccaatg gtaccaatgt taacatgcgg cttagtacgc tcgtactttt cctttgccat    1200
```

```
<210> SEQ ID NO 2
<211> LENGTH: 1200
<212> TYPE: DNA
<213> ORGANISM: Gardnerella vaginalis

<400> SEQUENCE: 2
atggcaaagg aaaagtacga gcgtactaag ccgcatgtta acattggtac cattggtcac      60
gttgatcacg gtaagactac cttgaccgcg gctatttcta aggtgctgca tggcgagtat     120
ccagatctga accctcagta tgacttcgat cagatcgacg ccgctccaga agagaaggag     180
cgcggcatta ccattaacat cgcccacatc gagtatcaga cggctgcacg ccactatgct     240
cacgtggacg ctccaggcca cgctgattac gttaagaaca tgatcactgg tgccgctcag     300
atggatggcg caatcctcgt ggttgctgct accgacggtc caatggctca gacccgtgaa     360
cacgtcttgc ttgctaagca ggtcggcgtt ccaaaaattc ttgttgcttt gaacaagtgc     420
gatatggttg acgacgaaga gcttatcgac ctcgttgaag aagaggttcg tgacctcctc     480
gaagaaaacg gcttcgatcg cgattgccca gtcatccgta cttccgctta cggcgctttg     540
catgatgacg ctccagacca cgacaagtgg gtagagaccg tcaaggaact catgaaggct     600
gttgacgagt acattccaac cccaactcac gatcttgaca agccattctt gatgccaatc     660
gaagatgtgt tcaccatctc cggtcgtggt accgttgtca ccggtcgtgt tgagcgtggt     720
aagctcccaa tcaacacccc agttgagatt gttggtttgc gtgataccca gaccaccacc     780
gtcacctcta tcgagacctt ccacaagcag atggatgagg ccgaggctgg cgataacact     840
ggtcttcttc tccgtggtat caaccgtacc gacgttgagc gtggtcaggt tgtggctgct     900
ccaggttctg tgactccaca caccaagttc gaaggcgaag tttacgtctt gaccaaggat     960
gaaggtggcc gtcactcgcc attcttctcc aactaccgtc cacagttcta cttccgtacc    1020
accgatgtta ctggcgttat caccttgcca gaaggcatcg aaatggttca gccaggcgat    1080
cacgcaacct tcactgttga gttgatccag gctatcgcaa tggaagaggg cttgaccttc    1140
gcagttcgtg aaggtggccg taccgttggt tctggtcgtg tgaccaagat tcttgcctag    1200

<210> SEQ ID NO 3
<211> LENGTH: 552
<212> TYPE: DNA
<213> ORGANISM: Lactobacillus jensenii

<400> SEQUENCE: 3
gctactgttt taactcaagc tatcgttaat gaaggtatga agaacgtaac tgccggtgct      60
aaccctgttg gtattcgtcg tggtattgaa aaggctacta aggctgcagt tgatgaattg     120
cataagatta gccacaaggt ttctggccgt gacgaaattg cacaagtagc tagcgtatca     180
agtgcttcag aagaagtagg taacttgatt gctgatgcta tggaaaaggt tggccatgat     240
ggtgttatct caattgaaga atcaaagggt gttaacactg aactttcagt agttgaaggt     300
atgcaatttg accgtggtta cctttcacaa tacatggtaa ctgacaacga caagatggaa     360
gctgatcttg ataatccata catcttgatt actgataaga agatttctaa cattcaagat     420
atcttgccat tattacaaga aattgttcaa caaggtaagt cattacttat tattgctgat     480
gatgttgaag gtgaagcatt accaactctt gtttttgaaca agattcgtgg tactttcaac     540
gttgttgcag ta                                                         552

<210> SEQ ID NO 4
<211> LENGTH: 552
```

<212> TYPE: DNA
<213> ORGANISM: Lactobacillus jensenii

<400> SEQUENCE: 4
gctactgttt taactcaagc tatcgttaat gaaggtatga agaacgtaac tgccggtgct        60
aaccctgttg gtattcgtcg tggtattgaa aaggctacta aggctgcagt tgatgaattg       120
cataagatta gccacaaggt ttctggccgt gacgaaattg cacaagtagc tagcgtatca       180
agtgcttcag aagaagtagg taacttgatt gctgatgcta tggaaaaggt tggccatgat       240
ggtgttatct caattgaaga atcaaagggt gttaacactg aactttcagt agttgaaggt       300
atgcaatttg accgtggtta cctttcacaa tacatggtaa ctgacaacga caagatggaa       360
gctgatcttg ataatccata catcttgatt actgataaga agatttctaa cattcaagat       420
atcttgccat tattacaaga aattgttcaa caaggtaagt cattacttat tattgctgat       480
gatgttgaag gtgaagcatt accaactctt gttttgaaca agattcgtgg tactttcaac       540
gttgttgcag tt                                                          552

<210> SEQ ID NO 5
<211> LENGTH: 1614
<212> TYPE: DNA
<213> ORGANISM: Lactobacillus jensenii

<400> SEQUENCE: 5
attaaatttg atgaaaaagc aagacgctca ctttttaaagg gtgttgataa gttagctgac        60
actgttaaga ctacattagg acctaagggg cgcaacgttg ttcttgaaaa gagctatggt       120
gcaccagaaa ttactaacga cggtgtaact attgctaagg caattgaact taaggaccac       180
ttcgaaaata tgggtgctaa gcttgttagc gaagttgctc aaaagactaa cgatattgct       240
ggtgacggta ctactactgc tactgtttta actcaagcta tcgttaacga aggtatgaag       300
aacgtaactg ctggtgctaa cccagttggt attcgtcgcg gtattgaaaa ggcaactaag       360
gctgctgttg atgaattaca caagattagc cacaaggttt ctggccgtga tgaaattgcc       420
caagtagcta gcgtatcaag tgcttcagaa gaagtaggta acttgattgc tgacgctatg       480
gaaaaggttg gtcacgatgg tgttatctca attgaagaat caaagggtgt taacactgaa       540
ctttcagtag ttgaagggat gcaatttgat cgtggttacc tttcacaata catggtaact       600
gacaacgata agatggaagc agaccttgat aacccataca tcttgattac tgataagaag       660
atttctaaca ttcaagatat cttgccatta cttcaagaaa tcgtacaaca aggtaagtca       720
ttacttatca ttgctgatga tgttgaaggt gaagcattac caactcttgt tttgaacaag       780
attcgtggta ctttcaacgt tgttgcagtt aaggctccag ctttggtga ccgtcgtaag       840 gctcaattac aagatattgc tgctttaact ggtggtactg taattaccga agacttaggc       900
ttagaactta aggacactaa gattgatcaa ttaggtcaag ctggtaaggt aactgtaact       960
aaggattcaa ctactattgt tgaaggtgct ggtactaagg aagctatcgc tgaaagagtt      1020
gactcaatta gaaaagaaat tgaaaactca actagtgact tcgacaaaga aaagttacaa      1080
gaacgtcttg ctaaacttgc tggcggtgtt gcagtaatca aggttggtgc tgctactgaa      1140
accgaattga aggaacgtaa gtacagaatc gaagatgcct tgaactcaac tcgtgctgca      1200
gttgaagaag ttacgttgc tggtggtggt actgccttag tagacgttaa gaaggcaatc      1260
actaagcttg ctagcgacaa tgaagatgaa caaactggta ttaacatcgt tttacgtgca      1320
cttagcgcac cagttcgtca aatcgctgaa aacgctggta aagatggttc agtaatctta      1380

```
gaccacttaa tgagtgctga tccagaagtt ggttacaacg ctgcaactga caagtgggaa    1440
aacatggtta gggccggaat tattgaccca accaaggtaa ctcgttcagc tttacaaaat    1500
gctgcatcaa tcgctgcatt actcttaact actgaagctg tagttgctga aattccagaa    1560
gaaaagccag ctgcacctgc taacccagct gcaggtatgg gcggcatgat gtaa          1614

<210> SEQ ID NO 6
<211> LENGTH: 552
<212> TYPE: DNA
<213> ORGANISM: Lactobacillus jensenii

<400> SEQUENCE: 6
gctactgttt taactcaagc tatcgttaac gaaggtatga agaacgtaac tgctggtgct      60
aacccagttg gtattcgtcg cggtattgaa aaggcaacta aggctgctgt tgatgaatta     120
cacaagatta gccacaaggt ttctggccgt gatgaaattg cccaagtagc tagcgtatca     180
agtgcttcag aagaagtagg taacttgatt gctgacgcta tggaaaaggt tggtcacgat     240
ggtgttatct caattgaaga atcaaagggt gttaacactg aactttcagt agttgaaggg     300
atgcaatttg atcgtggtta cctttcacaa tacatggtaa ctgacaacga taagatggaa     360
gcagaccttg ataacccata catcttgatt actgataaga agatttctaa cattcaagat     420
atcttgccat tacttcaaga aatcgtacaa caaggtaagt cattacttat cattgctgat     480
gatgttgaag gtgaagcatt accaactctt gttttgaaca agattcgtgg tactttcaac     540
gttgttgcag ta                                                        552

<210> SEQ ID NO 7
<211> LENGTH: 552
<212> TYPE: DNA
<213> ORGANISM: Lactobacillus jensenii

<400> SEQUENCE: 7
gctactgttt taactcaagc tatcgttaac gaaggtatga agaacgtaac tgctggtgct      60
aacccagttg gtattcgtcg cggtattgaa aaggcaacta aggctgctgt tgatgaatta     120
cacaagatta gccacaaggt ttctggccgt gatgaaattg cccaagtagc tagcgtatca     180
agtgcttcag aagaagtagg taacttgatt gctgacgcta tggaaaaggt tggtcacgat     240
ggtgttatct caattgaaga atcaaagggt gttaacactg aactttcagt agttgaaggg     300
atgcaatttg atcgtggtta cctttcacaa tacatggtaa ctgacaacga taagatggaa     360
gcagaccttg ataacccata catcttgatt actgataaga agatttctaa cattcaagat     420
atcttgccat tacttcaaga aatcgtacaa caaggtaagt cattacttat cattgctgat     480
gatgttgaag gtgaagcatt accaactctt gttttgaaca agattcgtgg tactttcaac     540
gttgttgcag tt                                                        552

<210> SEQ ID NO 8
<211> LENGTH: 552
<212> TYPE: DNA
<213> ORGANISM: Lactobacillus jensenii

<400> SEQUENCE: 8
gctactgttt taactcaagc tatcgttaac gaaggtatga agaacgtaac tgctggtgct      60
aacccagttg gtattcgtcg cggtattgaa aaggcaacta aggctgctgt tgatgaatta     120
cacaagatta gccacaaggt ttctggccgt gatgaaattg cccaagtagc tagcgtatca     180
agtgcttcag aagaagtagg taacttgatt gctgacgcta tggaaaaggt tggtcacgat     240
```

```
ggtgttatct caattgaaga atcaaagggt gttaacactg aactttcagt agttgaaggg        300
atgcaatttg atcgtggtta cctttcacaa tacatggtaa ctgacaacga taagatggaa        360
gcagaccttg ataacccata catcttgatt actgataaga agatttctaa cattcaagat        420
atcttgccat tacttcaaga aatcgtacaa caaggtaagt cattacttat cattgctgat        480
gatgttgaag gtgaagcatt accaactctt gttttgaaca agattcgtgg tactttcaac        540
gttgttgcag tt                                                            552
```

```
<210> SEQ ID NO 9
<211> LENGTH: 552
<212> TYPE: DNA
<213> ORGANISM: Lactobacillus jensenii

<400> SEQUENCE: 9
gctactgttt taactcaagc tatcgttaac gaaggtatga agaacgtaac tgctggtgct         60
aacccagttg gtattcgtcg cggtattgaa aaggcaacta aggctgctgt tgatgaatta        120
cacaagatta gccacaaggt ttctggccgt gatgaaattg cccaagtagc tagcgtatca        180
agtgcttcag aagaagtagg taacttgatt gctgacgcta tggaaaaggt tggtcacgat        240
ggtgttatct caattgaaga atcaaagggt gttaacactg aactttcagt agttgaaggg        300
atgcaatttg atcgtggtta cctttcacaa tacatggtaa ctgacaacga taagatggaa        360
gcagaccttg ataacccata catcttgatt actgataaga agatttctaa cattcaagat        420
atcttgccat tacttcaaga aatcgtacaa caaggtaagt cattacttat cattgctgat        480
gatgttgaag gtgaagcatt accaactctt gttttgaaca agattcgtgg tactttcaac        540
gttgttgcag tt                                                            552
```

```
<210> SEQ ID NO 10
<211> LENGTH: 607
<212> TYPE: DNA
<213> ORGANISM: Lactobacillus jensenii

<400> SEQUENCE: 10
tgaattcgag ggggcggggg atgggacgac gactgctact gttttaactc aagctatcgt         60
taacgaaggt atgaagaacg taactgctgg tgctaaccca gttggtattc gtcgcggtat        120
tgaaaaggca actaaggctg ctgttgatga attacacaag attagccaca aggtttctgg        180
ccgtgatgaa attgcccaag tagctagcgt atcaagtgct tcagaagaag taggtaactt        240
gattgctgac gctatggaaa aggttggtca cgatggtgtt atctcaattg aagaatcaaa        300
gggtgttaac actgaacttt cagtagttga agggatgcaa tttgatcgtg gttacctttc        360
acaatacatg gtaactgaca cgataagat ggaagcagac cttgataacc catacatctt        420
gattactgat aagaagattt ctaacattca agatatcttg ccattacttc aagaaatcgt        480
acaacaaggt aagtcattac ttatcattgc tgatgatgtt gaaggtgaag cattaccaac        540
tcttgttttg aacaagattc gtggtacttt caacgttgtt gcagttaaag cccccggctt        600
cggcgac                                                                  607
```

```
<210> SEQ ID NO 11
<211> LENGTH: 506
<212> TYPE: DNA
<213> ORGANISM: Lactobacillus crispatus

<400> SEQUENCE: 11
```

```
gaagggatga agaacgtcac tgctggtgct aacccagttg gtattcgtcg cggtattgaa      60
aaggcaacta aggctgctgt tgatgaactt cacaagatca gccacaaggt tgaatcaaag     120
gatcaaattg ctaacgttgc tgctgtttca tcagcttcta aagaagttgg tgctttgatc     180
gctgatgcta tggaaaaggt tggtcacgat ggtgttatca ctattgaaga ctcacgtggt     240
atcaacactg aactttcagt agttgaaggt atgcaatttg accgtggtta cttatcacaa     300
tacatggtaa ctgacaacga caagatggaa gcagaccttg ataatccata tatcttgatc     360
actgacaaga agatttcaaa cattcaagac atcttgccat tacttcaaga aattgttcag     420
caaggcaagt cattgttgat cattgctgac gatgtaactg gtgaagctct tccaactctt     480
gttttgaaca agatccgtgg aacatt     506

<210> SEQ ID NO 12
<211> LENGTH: 1626
<212> TYPE: DNA
<213> ORGANISM: Lactobacillus crispatus

<400> SEQUENCE: 12
atggcaaaag atattaaatt ctcagaaaat gcaagacgtt ctctttttaaa gggtgttaat      60 aagttagctg atactgttaa gactactatt ggtcctaagg gtagaaacgt tgttttggaa     120
caaagttacg gcaaccctga catcactaac gatggtgtta ccattgcaaa gtccatcgag     180
ttaaaggacc actacgaaaa catgggtgct aaacttgttg ctgaagctgc tcaaaagact     240
aatgatattg ctggtgacgg tactactacc gcaactgttt tgactcaagc aattactaat     300
gaaggtatga gaacgtaac tgctggtgct aacccagttg gcattcgtcg tggtattgaa     360
aaagctactg aagctgctgt taatgaattg cacaagatta gccacaaggt tgaatcaaga     420
gaccaaattg ctaacgtagc tgcagtttca tcatcttcaa aggaagttgg taacttaatc     480
gctgacgcta tggaaaaggt tggtcacgat ggcgttatca ctattgaaga ttcacgtggt     540
atcaacactg aactttcagt agttgaaggt atgcaatttg atcgtggtta cttatcacaa     600
tacatggtaa ctgacaacga taagatggaa gcagatcttg ataatcctta cattttgatc     660
actgacaaga agatctcaaa cattcaagat atcttgccac ttcttcaaga aattgttcaa     720
caaggtaagt cattattgat cattgctgat gacgttactg gtgaagctct tccaacactt     780
gtattgaaca agattcgtgg taccttcaac gttgtagctg ttaaggctcc tggctttggt     840
gaccgtcgta aggctcagtt acaagatatt gctgctttga ctggtggtac tgtgattact     900
gatgacttag gtcttgaatt aaaggacact aagattgatc aattaggtca agctcgtcgt     960
gtaactgtaa ccaaggactc aactactatt gttgacggtg ctggttcaaa ggatgctatt    1020
caagaacgtg aagattcaat cagaaagcaa attgaagaat caacttcaga ctttgacaag    1080
aagaagcttc aagaacgtct tgctaagtta actggtggtg tagctgttat ccacgtaggt    1140
gctgctactg aaaccgaatt gaaggaacgt cgttacagaa ttgaagacgc tttgaactca    1200
actcgtgccg ctgttgacga aggttacgtt gctggtggtg tactgctttt agtagacgtt    1260
gagaaggcta tcaatgatct taaggctgat actgcagatg aaaatactgg tatccaaatc    1320
gtattaagag ctttgtcagc accagttcgt caaattgctg aaaacgcagg taagaatggt    1380
gaagttgttt tgaaccactt actcaagcaa gaaaacgaaa ttggctacaa tgctgctact    1440
gatacttggg aaaacatggt agatgctggt atcattgatc caaccaaggt aaccagaacc    1500
gctttgcaaa atgctgcttc aattgccgct cttctgctta ctactgaagc tgttgttgca    1560
gaaattcctg aagaaaagcc agctaaccca gctccacaag ctggtgcacc aggaatgggt    1620
```

-continued

```
atgtaa                                                                 1626

<210> SEQ ID NO 13
<211> LENGTH: 506
<212> TYPE: DNA
<213> ORGANISM: Lactobacillus crispatus

<400> SEQUENCE: 13
gaaggcatga agaacgtcac tgctggtgct aacccagttg gcattcgtcg tggtattgaa      60
aaagctactg aagctgctgt taatgaattg cacaagatta gccacaaggt tgaatcaaga     120
gaccaaattg ctaacgtagc tgcagtttca tcatcttcaa aggaagttgg taacttaatc     180
gctgacgcta tggaaaaggt tggtcacgat ggcgttatca ctattgaaga ttcacgtggt     240
atcaatactg aactttcagt agttgaaggt atgcaatttg atcgtggtta cttatcacaa     300
tacatggtaa ctgacaacga taagatggaa gcagatcttg ataatcctta cattttgatc     360
actgacaaga agatctcaaa cattcaagat atcttgccac ttcttcaaga aattgttcaa     420
caaggtaagt cattattgat cattgctgat gacgttactg gtgaagctct tccaacactt     480
gtattgaaca agatccgtgg aacatt                                         506

<210> SEQ ID NO 14
<211> LENGTH: 552
<212> TYPE: DNA
<213> ORGANISM: Lactobacillus crispatus

<400> SEQUENCE: 14
gcaactgttt tgactcaagc aattactaat gaaggtatga agaacgtaac tgctggtgct      60
aacccagttg gcattcgtcg tggtattgaa aaagctactg aagctgctgt taatgaattg     120
cacaagatta gccacaaggt tgaatcaaga gaccaaattg ctaacgtagc tgcagtttca     180
tcatcttcaa aggaagttgg taacttaatc gctgacgcta tggaaaaggt tggtcacgat     240
ggcgttatca ctattgaaga ttcacgtggt atcaacactg aactttcagt agttgaaggt     300
atgcaatttg atcgtggtta cttatcacaa tacatggtaa ctgacaacga taagatggaa     360
gcagatcttg ataatcctta cattttgatc actgacaaga agatctcaaa cattcaagat     420
atcttgccac ttcttcaaga aattgttcaa caaggtaagt cattattgat cattgctgat     480
gacgttactg gtgaagctct tccaacactt gtattgaaca agattcgtgg taccttcaac     540
gttgtagctg tt                                                         552

<210> SEQ ID NO 15
<211> LENGTH: 552
<212> TYPE: DNA
<213> ORGANISM: Lactobacillus crispatus

<400> SEQUENCE: 15
gcaactgttt tgactcaagc aattactaat gaaggtatga agaacgtaac tgctggtgct      60
aacccagttg gcattcgtcg tggtattgaa aaagctactg aagctgctgt taatgaattg     120
cacaagatta gccacaaggt tgaatcaaga gaccaaattg ctaacgtagc tgcagtttca     180
tcatcttcaa aggaagttgg taacttaatc gctgacgcta tggaaaaggt tggtcacgat     240
ggcgttatca ctattgaaga ttcacgtggt atcaatactg aactttcagt agttgaaggt     300
atgcaatttg atcgtggtta cttatcacaa tacatggtaa ctgacaacga taagatggaa     360
gcagatcttg ataatcctta cattttgatc actgacaaga agatctcaaa cattcaagat     420
```

```
atcttgccac ttcttcaaga aattgttcaa caaggtaagt cattattgat cattgctgat      480
gacgttactg gtgaagctct tccaacactt gtattgaaca agattcgtgg taccttcaac      540
gttgtagctg tt                                                         552

<210> SEQ ID NO 16
<211> LENGTH: 604
<212> TYPE: DNA
<213> ORGANISM: Lactobacillus crispatus

<400> SEQUENCE: 16
attcgagggg gcgggggatg ggacgacgac cgcaactgtt ttgactcaag caattactaa       60
tgaaggtatg aagaacgtaa ctgctggtgc taacccagtt ggcattcgtc gtggtattga      120
aaaagctact gaagctgctg ttaatgaatt gcacaagatt agccacaagg ttgaatcaag      180
agaccaaatt gctaacgtag ctgcagtttc atcatcttca aaggaagttg gtaacttaat      240
cgctgacgct atggaaaagg ttggtcacga tggcgttatc actattgaag attcacgtgg      300
tatcaatact gaactttcag tagttgaagg tatgcaattt gatcgtggtt acttatcaca      360
atacatggta actgacaacg ataagatgga agcagatctt gataatcctt acattttgat      420
cactgacaag aagatctcaa acattcaaga tatcttgcca cttcttcaag aaattgttca      480
acaaggtaag tcattattga tcattgctga tgacgttact ggtgaagctc ttccaacact      540
tgtattgaac aagattcgtg gtaccttcaa cgttgtagct gttaaagccc ccggcttcgg      600
cgac                                                                 604

<210> SEQ ID NO 17
<211> LENGTH: 939
<212> TYPE: DNA
<213> ORGANISM: Lactobacillus gasseri

<400> SEQUENCE: 17
atgattgaat ttgaaaaacc aaatattacc gtagtagacc aagaggaggc atacggtaag       60
tttgttgtcg aaccactgga acgcggtttc gggactactt taggtaactc actccgtcga      120
gttttactta cttctattcc aggtacggca ctttcttata ttcagattga tggtgtgtta      180
catgaatttt caacaattcc tggcgttaga gaagacgtca caaaaattat tcttaatttg      240
aagaaactag agttaaagtc actctcagat gaagaaaaaa ttgccgaaat cgatgtaact      300
ggtccagcaa tcgtaactgc tgctgactta aaggtcgact ctgatattga ggtcttaaat      360
ccagatcaat atatttgtag tattgctgat ggtggccatt tgcatatgaa tgttgcgatc      420
aagaatggtc gtggttatgt tcccgcaagt gaaaacaaga ctgatgacat gcctattggc      480
gtcatccccg ttgattcact cttttcacca atcaaaaaag ttaactacca agttgaaagt      540
gctcgtgttg gtaaaagaga cgattatgac aaattaactt tagaaatttg gactgatggt      600
tcaatcacac ctaatgatgc ccttagtttc gctgcgaaga ttcttgtaga acacttcaaa      660
gtatttatgt ctactgatat ggatgcgcag tttgatgatg taatggtaga aaaagaggac      720
gataagaatg agaagaagct tgagatgacg atcgaagagc ttgacttatc tgttcgttca      780
tataactgct tgaaacgtgc aggaattaat actgttcaag aattaactga taaatctgaa      840
gcagatatga tgcgcgtacg taacttagga cgtaagtcat tagaagaagt aaagaataaa      900
cttgccgaac ttggtctatc acttcgtcaa gatgactaa                            939

<210> SEQ ID NO 18
<211> LENGTH: 939
```

-continued

```
<212> TYPE: DNA
<213> ORGANISM: Lactobacillus johnsonii

<400> SEQUENCE: 18
atgattgaat ttgaaaaacc aaatattacc gtagtagacc aagaggaggc atacggtaag      60
tttgttgtcg aaccactgga acgcggtttc gggactactt taggtaactc actccgtcga     120
gttttactta cttctattcc aggtacggca ctttcttaca ttcagattga tggtgtgtta     180
catgaatttt caacaattcc tggcgttaga gaagacgtca cgaagatcat tcttaatttg     240
aagaaactag agttaaagtc actctcagat gaagaaaaaa ttgctgaaat cgatgtaact     300
ggaccagcaa ttgtaactgc tgctgatttg aaggtcgact ctgatattga ggtcttaaat     360
ccagatcaat atatttgtag tattgctgat ggtggccatt tgcatatgaa cgttgcgatc     420
aagactggtc gtggttatgt tcccgcaagt gaaaacaaga cagatgacat gcctattggt     480
gtcatccccg ttgattcact cttctcacca atcaaaaaag ttaactacca agttgaaagt     540
gctcgtgttg gtaagagaga tgactatgac aaattaactt tagaaatttg gactgatggt     600
tcaatcacac ctaatgatgc ccttagtttc gctgcgaaga ttcttgtaga acacttcaaa     660
gtatttatgt ctactgatat ggatgcgcag tttgatgatg taatggtaga aaaagaggac     720
gataagaacg aaaagaagct tgagatgacg atcgaagagc ttgatttatc tgttcgttcc     780
tataactgct tgaaacgtgc aggaattaat actgttcaag aattaactga taaatctgaa     840
gcagatatga tgcgcgtacg taacttagga cgtaagtcat tagaagaagt aaagaataaa     900
cttgccgatc ttggtctatc acttcgtcaa gatgactaa                            939

<210> SEQ ID NO 19
<211> LENGTH: 939
<212> TYPE: DNA
<213> ORGANISM: Lactobacillus johnsonii

<400> SEQUENCE: 19
atgattgaat ttgaaaaacc aaatattacc gtagtagacc aagaggaggc atacggtaag      60
tttgttgtcg aaccactgga acgcggtttc gggactactt taggtaactc actccgtcga     120
gttttactta cttctattcc aggtacggca ctttcttaca ttcagattga tggtgtgtta     180
catgaatttt caacaattcc tggcgttaga gaagacgtca cgaagatcat tcttaatttg     240
aagaaactag agttaaagtc actctcagat gaagaaaaaa ttgctgaaat cgatgtaact     300
ggaccagcaa ttgtaactgc tgctgatttg aaggtcgact ctgatattga ggtcttaaat     360
ccagatcaat atatttgtag tattgctgat ggtggccatt tgcatatgaa cgttgcgatc     420
aagactggtc gtggttatgt tcccgcaagt gaaaacaaga cagatgacat gcctattggt     480
gtcatccccg ttgattcact cttctcacca atcaaaaaag ttaactacca agttgaaagt     540
gctcgtgttg gtaagagaga tgactatgac aaattaactt tagaaatttg gactgatggt     600
tcaatcacac ctaatgatgc ccttagtttc gctgcgaaga ttcttgtaga acacttcaaa     660
gtatttatgt ctactgatat ggatgcgcag tttgatgatg taatggtaga aaaagaggac     720
gataagaacg aaaagaagct tgagatgacg atcgaagagc ttgatttgtc tgttcgttcc     780
tataactgct tgaaacgtgc aggaattaat actgttcaag aattaactga taaatctgaa     840
gcagatatga tgcgcgtacg taacttagga cgtaagtcat tagaagaagt aaagaataaa     900
cttgccgatc ttggtctatc acttcgtcaa gatgactaa                            939

<210> SEQ ID NO 20
```

```
<211> LENGTH: 939
<212> TYPE: DNA
<213> ORGANISM: Lactobacillus johnsonii

<400> SEQUENCE: 20
atgattgaat ttgaaaaacc aaatattacc gtagtagacc aagaggaggc atacggtaag      60
tttgttgtcg aaccactgga acgcggtttc gggactactt taggtaactc actccgtcga     120
gttttactta cttctattcc aggtacggca ctttcttaca ttcagattga tggtgtgtta     180
catgaatttt caacaattcc tggcgttaga gaagacgtca cgaagatcat tcttaatttg     240
aagaaactag agttaaagtc actctcagat gaagaaaaaa ttgctgaaat cgatgtaact     300
ggaccagcaa ttgtaactgc tgctgatttg aaggtcgact ctgatattga ggtcttaaat     360
ccagatcaat atatttgtag tattgctgat ggtggccatt tgcatatgaa cgttgcgatc     420
aagactggtc gtggttatgt tcccgcaagt gaaaacaaga cagatgacat gcctattggt     480
gtcatccccg ttgattcact cttctcacca atcaaaaaag ttaactacca agttgaaagt     540
gctcgtgttg gtaagagaga tgactatgac aaattaactt tagaaatttg gactgatggt     600
tcaatcacac ctaatgatgc ccttagtttc gctgcgaaga ttcttgtaga acacttcaaa     660
gtatttatgt ctactgatat ggatgcgcag tttgatgatg taatggtaga aaaagaggac     720
gataagaacg aaaagaagct tgagatgacg atcgaagagc ttgatttgtc tgttcgttcc     780
tataactgct tgaaacgtgc aggaattaat actgttcaag aattaactga taaatctgaa     840
gcagatatga tgcgcgtacg taacttagga cgtaagtcat tagaagaagt aaagaataaa     900
cttgccgatc ttggtctatc acttcgtcaa gatgactaa                            939

<210> SEQ ID NO 21
<211> LENGTH: 939
<212> TYPE: DNA
<213> ORGANISM: Lactobacillus johnsonii

<400> SEQUENCE: 21
atgattgaat ttgaaaaacc aaatattacc gtagtagacc aagaggaggc atacggtaag      60
tttgttgtcg aaccactgga acgcggtttc gggactactt taggtaactc actccgtcga     120
gttttactta cttctattcc aggtacggca ctttcttaca ttcagattga tggtgtgtta     180
catgaatttt caacaattcc tggcgttaga gaagacgtca cgaagatcat tcttaatttg     240
aagaaactag agttaaagtc actctcagat gaagaaaaaa ttgctgaaat cgatgtaact     300
ggaccagcaa ttgtaactgc tgctgatttg aaggtcgact ctgatattga ggtcttaaat     360
ccagatcaat atatttgtag tattgctgat ggtggccatt tgcatatgaa cgttgcgatc     420
aagactggtc gtggttatgt tcccgcaagt gaaaacaaga cagatgacat gcctattggt     480
gtcatccccg ttgattcact cttctcacca atcaaaaaag ttaactacca agttgaaagt     540
gctcgtgttg gtaagagaga tgactatgac aaattaactt tagaaatttg gactgatggt     600
tcaatcacac ctaatgatgc ccttagtttc gctgcgaaga ttcttgtaga acacttcaaa     660
gtatttatgt ctactgatat ggatgcgcag tttgatgatg taatggtaga aaaagaggac     720
gataagaacg aaaagaagct tgagatgacg atcgaagagc ttgatttgtc tgttcgttcc     780
tataactgct tgaaacgtgc aggaattaat actgttcaag aattaactga taaatctgaa     840
gcagatatga tgcgcgtacg taacttagga cgtaagtcat tagaagaagt aaagaataaa     900
cttgccgatc ttggtctatc acttcgtcaa gatgactaa                            939
```

```
<210> SEQ ID NO 22
<211> LENGTH: 939
<212> TYPE: DNA
<213> ORGANISM: Lactobacillus johnsonii

<400> SEQUENCE: 22
atgattgaat ttgaaaaacc aaatattacc gtagtagacc aagaggaggc atacggtaag          60
tttgttgtcg aaccactgga acgcggtttc gggactactt taggtaactc actccgtcga         120
gttttactta cttctattcc aggtacggca ctttcttata ttcagattga tggtgtgtta         180
catgaatttt caacagttcc tggcgttaga gaagacgtca cgaagatcat tcttaatttg         240
aagaaactag agttaaagtc actctcagat gaagaaaaaa ttgctgaaat cgatgtaact         300
ggaccagcaa ttgtaactgc tgctgatttg aaggtcgact ctgatattga ggtcttaaat         360
ccagatcaat atatttgtag tattgctgat ggtggccatt tgcatatgaa cgttgcgatc         420
aagactggtc gtggttatgt tcccgcaagt gaaaacaaga cagatgacat gcctattggt         480
gtcatccccg ttgattcact cttctcacca atcaaaaaag ttaactacca agttgaaagt         540
gctcgtgttg gtaagagaga tgactatgac aaattaactt tagaaatttg gactgatggt         600
tcaatcacac ctaatgatgc ccttagtttc gctgcgaaga ttcttgtaga acacttcaaa         660
gtatttatgt ctactgatat ggatgcgcag tttgatgatg taatggtaga aaaagaggac         720
gataagaacg aaaagaagct tgagatgacg atcgaagagc ttgatttgtc tgttcgttcc         780
tataactgct tgaaacgtgc aggaattaat actgttcaag aattaactga taaatctgaa         840
gcagatatga tgcgcgtacg taacttagga cgtaagtcat tagaagaagt aaagaataaa         900
cttaccgatc ttggtctatc acttcgtcaa gatgactaa                                 939

<210> SEQ ID NO 23
<211> LENGTH: 723
<212> TYPE: DNA
<213> ORGANISM: Lactobacillus johnsonii

<400> SEQUENCE: 23
aagaggaggc atacggtaag tttgttgtcg aaccactgga acgcggtttc gggactactt          60
taggtaactc actccgtcga gttttactta cttctattcc aggtacggca ctttcttaca         120
ttcagattga tggtgtgtta catgaatttt caacaattcc tggcgttaga gaagacgtca         180
cgaagatcat tcttaatttg aagaaactag agttaaagtc actctcagat gaagaaaaaa         240
ttgctgaaat cgatgtaact ggaccagcaa ttgtaactgc tgctgatttg aaggtcgact         300
ctgatattga ggtcttaaat ccagatcaat atatttgtag tattgctgat ggtggccatt         360
tgcatatgaa cgttgcgatc aagactggtc gtggttatgt tcccgcaagt gaaaacaaga         420
cagatgacat gcctattggt gtcatccccg ttgattcact cttctcacca atcaaaaaag         480
ttaactacca agttgaaagt gctcgtgttg gtaagagaga tgactatgac aaattaactt         540
tagaaatttg gactgatggt tcaatcacac ctaatgatgc ccttagtttc gctgcgaaga         600
ttcttgtaga acacttcaaa gtatttatgt ctactgatat ggatgcgcag tttgatgatg         660
taatggtaga aaaagaggac gataagaacg aaaagaagct tgagatgacg attgaagagc         720
ttg                                                                        723

<210> SEQ ID NO 24
<211> LENGTH: 697
<212> TYPE: DNA
<213> ORGANISM: Lactobacillus taiwanensis
```

<400> SEQUENCE: 24

```
aagaggaggc atacggtaag tttgttgtcg aaccactgga acgcggtttc gggactactt      60
taggtaactc actccgtcga gttttactta cttctattcc agggacggca ctttcttaca     120
ttcagattga tggagtattg catgaatttt caacaattcc tggcgtaaga gaagacgtca     180
cgaaaattat tcttaatttg aagaaactag aattaaagtc actctcagat gaagaaaaaa     240
ttgctgaaat cgatgtaact ggtccagcaa tcgtaactgc tgccgattta aaggtcgact     300
ctgatattga ggtcttaaat ccagatcaat atatttgtag tattgctgat ggtggccatt     360
tgcatatgaa cgttgcgatc aaatctggtc gtggttatgt tcccgcaagt gaaacaagaa     420
cagatgacat gcctattggt gtcatccccg ttgattcact cttttcacca atcaaaaaag     480
ttaactacca agttgaaagt gctcgtgttg gtaaaagaga cgattatgac aaattaactt     540
tagaaatttg gactgatggt tcaatcacac ctaatgatgc ccttagtttc gctgcgaaga     600
ttcttgtaga acacttcaaa gtatttatgt ctactgatat ggatgcgcag tttgatgatg     660
taatggtaga aaaagaggac gataagaacg agaagaa                             697
```

<210> SEQ ID NO 25
<211> LENGTH: 644
<212> TYPE: DNA
<213> ORGANISM: Lactobacillus johnsonii

<400> SEQUENCE: 25

```
gtttcgggac tactttaggt aactcactcc gtcgagtttt acttacttct attccaggta      60
cggcactttc ttacattcag attgatggtg tgttacatga attttcaaca attcctggcg     120
ttagagaaga cgtcacgaag atcattctta atttgaagaa actagagtta aagtcactct     180
cagatgaaga aaaaattgct gaaatcgatg taactggacc agcaattgta actgctgctg     240
atttgaaggt cgactctgat attgaggtct aaatccaga tcaatatatt tgtagtattg      300
ctgatggtgg ccatttgcat atgaacgttg cgatcaagac tggtcgtggt tatgttcccg     360
caagtgaaaa caagacagat gacatgccta ttggtgtcat ccccgttgat tcactcttct     420
caccaatcaa aaaagttaac taccaagttg aaagtgctcg tgttggtaag agagatgact     480
atgacaaatt aactttagaa atttggactg atggttcaat cacacctaat gatgccctta     540
gtttcgctgc gaagattctt gtagaacact tcaaagtatt tatgtctact gatatggatg     600
cgcagtttga tgatgtaatg gtagaaaaag aggacgataa gaac                     644
```

<210> SEQ ID NO 26
<211> LENGTH: 723
<212> TYPE: DNA
<213> ORGANISM: Lactobacillus pasteurii

<400> SEQUENCE: 26

```
ccaagaagaa tcttacggta agtttgttgt tgaaccactg aacgcggtt ttgggactac       60 tttaggtaac tcactccgtc gtgttttatt aacttctatt ccaggaacag cactttctta     120
cattcaaatt gatggtgtgt tacacgaatt ttctacagtt cctggcgtta gagaagacgt     180
cactaaaatt attcttaatt tgaagaaact agaattaaag tcactctcag atgaagaaaa     240
aattgcagaa atagatgtaa ctggaccagc tgtagttact gctgccgatt tgaaagtaga     300
ttctgatgtg gaagtcttaa atcctgatca atatatttgt actattgctg atggtggtca     360
tttgcatatg aacgttgcga ttaaaaatgg tcgtggctat gttcctgcaa gtgaaaataa     420
gactgacgaa atgccaattg gggtaattcc agtcgactca ctcttttcac caattaaaaa     480
```

-continued

```
agtaaactat caagttgaaa atgcacgtgt aggtaagaga gacgattatg ataaattaac      540
tttggaaatt tggaccaaca gttcaatcac acctaatgat gcccttagtt tcgctgcaaa      600
gatccttgaa gaacacttta aggtatttat gtctactgat atggatgctc agttagatga      660
tgtaatggta gaaaagaag acaataagaa tgaaagaaa cttgagatga ctatagagga      720
gct                                                                   723

<210> SEQ ID NO 27
<211> LENGTH: 563
<212> TYPE: DNA
<213> ORGANISM: Lactobacillus johnsonii

<400> SEQUENCE: 27
ttttacttac ttctattcca ggtacggcac tttcttacat tcagattgat ggtgtgttac       60
atgaattttc aacaattcct ggcgttagag aagacgtcac gaagatcatt cttaatttga      120
agaaactaga gttaaagtca ctctcagatg aagaaaaaat tgctgaaatc gatgtaactg      180
gaccagcaat tgtaactgct gctgatttga aggtcgactc tgatattgag gtcttaaatc      240
cagatcaata tatttgtagt attgctgatg gtggccattt gcatatgaac gttgcgatca      300
agactggtcg tggttatgtt cccgcaagtg aaaacaagac agatgacatg cctattggtg      360
tcatccccgt tgattcactc ttctcaccaa tcaaaaaagt taactaccaa gttgaaagtg      420
ctcgtgttgg taagagagat gactatgaca aattaacttt agaaatttgg actgatggtt      480
caatcacacc taatgatgcc cttagtttcg ctgcgaagat ccttgtagaa cacttcaaag      540
tatttatgtc tactgatatg gat                                             563

<210> SEQ ID NO 28
<211> LENGTH: 557
<212> TYPE: DNA
<213> ORGANISM: Lactobacillus johnsonii

<400> SEQUENCE: 28
ctccgtcgag ttttacttac ttctattcca ggtacggcac tttcttacat tcagattgat       60
ggtgtgttac atgaattttc aacaattcct ggcgttagag aagacgtcac gaagatcatt      120
cttaatttga agaaactaga gttaaagtca ctctcagatg aagaaaaaat tgctgaaatc      180
gatgtaactg gaccagcaat tgtaactgct gctgatttga aggtcgactc tgatattgag      240
gtcttaaatc cagatcaata tatttgtagt attgctgatg gtggccattt gcatatgaac      300
gttgcgatca agactggtcg tggttatgtt cccgcaagtg aaaacaagac agatgacatg      360
cctattggtg tcatccccgt tgattcactc ttctcaccaa tcaaaaaagt taactaccaa      420
gttgaaagtg ctcgtgttgg taagagagat gactatgaca aattaacttt agaaatttgg      480
actgatggtt caatcacacc taatgatgcc cttagtttcg ctgcgaagat tcttgtagaa      540
cacttcaaag tatttat                                                    557

<210> SEQ ID NO 29
<211> LENGTH: 939
<212> TYPE: DNA
<213> ORGANISM: Lactobacillus acetotolerans

<400> SEQUENCE: 29
atgattgaat ttgaaaaacc aaatattacc gttgttgagc aagaagattc ctacggtaaa       60
tttgttgttg aaccacttga acgaggcttt ggtactactt taggtaattc attacgtaga      120
```

-continued

```
gttttactta catctatacc aggtactgga cttgtctatg ttcaaattga tggtgtctta      180
cacgagttct caacagttcc tggcgtcaga gaagatgtag ctaagatgat tctgaatctg      240
aagaaacttg aattaaaagtg tctttcagat gatcaaaaga tcattgaatt ggacgttgaa      300
ggtccggcta ctgtaactgc tgatgatctt aaggctgacg cagatgtaga ggtcttaaat      360
ccagatcaat atatttgtac cattgctgaa ggtggtcact acatatgca aattgcggtt       420 agaaaaggcc gtggttatgt tactgcaagt gataacaaga gtgatgatat gccgattggt      480
gttatcccag ttgattctct tttttcacca attaaaaagg ttaattacca ggttgagtca      540
actcgtgttg gtaagagaga cgattttgac aagctcactt tagagatttg gactgatggt       600
tcaatcaagc ctaatgacgc ccttagtttt gctgctaaga ttttggtagc acactttaaa      660
gtgttcgaaa ctgctgatgc agatactaaa ttcaatgatg taatggtaga aaaagaggac      720
gataataagg aaaagaagct tgagatgact atcgaagagc ttgatctttc tgttcgttca      780
tataactgct aaagcgagc aggcattaat actctgcaag agttaactga taagaccgaa       840
gcagatatga tgcgtgtacg taatttggga cgtaaatcat tggaagaagt taaaaacaaa      900
ttagctgact taggactttc ccttcgtcaa gaagattaa                            939
```

<210> SEQ ID NO 30
<211> LENGTH: 939
<212> TYPE: DNA
<213> ORGANISM: Lactobacillus crispatus

<400> SEQUENCE: 30

```
atgattgaat ttgaaaaacc aaatattacc gttgttgaac aagaagattc ttacggtaag       60
tttgttgttg aaccacttga gcgaggcttt ggtactactt taggtaattc tttaagaaga      120
gtattactta cttctattcc aggtactgga cttgtttatg tgcaaattga tggcgttttat      180 cacgagttct caacagttcc tggcgtcaga gaagatgtaa ccaagatcat cttgaacttg      240
aagaaacttg aattaaaagtc tctttcagat gaacaaaagg ttattgaatt ggacattgaa      300
ggtccagcca cagtaactgc tgatgatctt aaagttgatg cagacgttca agtcttgaat      360
ccggatcaat atatttgtac cattgctgaa ggtggacact gcatatgga acttgccgta       420 aagaatggta gaggttatgt tgctgcaagt gacaataaga gtgatgacat gccaatcgga      480
gttatcccag ttgactcttt attctcacca attaagaagg ttaactacca agttgaatca      540
actcgtgttg gtaagagaga tgactttgat aagctcactt ttgagatttg gactgacggt       600
tcaatcaagc ctaatgacgc ccttagtttt gctgctaaaa ttttagttga acactttaag      660
gtatttgaat cagcagatgc aaatgctaaa ttcagcgaag taatggtgga aaaggaagac      720
gataagaagg aaaagaagct tgagatgact atcgaagagc ttgaccttc tgttcgttca       780 tataactgcc tgaagcgtgc tggcattaat actcttcaag agttaactga caagacagaa      840
tcagatatga tgcgtgtacg taacttagga cgtaaatcat tggaagaagt taaaaataaa      900
ttaaccgact taggtcttc acttcgtcaa gaagactaa                            939
```

<210> SEQ ID NO 31
<211> LENGTH: 942
<212> TYPE: DNA
<213> ORGANISM: Lactobacillus jensenii

<400> SEQUENCE: 31

```
atgattgaat ttgaaaaacc aaatattacc gttgttgacc aagaggatgc atacggtaag       60
tttgttgtcg aaccattaga acgtggattt ggtactactt taggtaattc attgcgtaga      120
```

-continued

```
gtattgctta cctcaattcc aggtacggca ctttcttaca tccaaattga tggcgttttg          180
catgaattct caacagttcc tggtgtacga gaagatgtta ccaagattgt tcttaatctg          240
aagaagcttg aacttaagtc tatagcagat gaagaaaaga ttgttgagct tgatgttgaa          300
ggcccagcta ctgtcactgc tggtgatttg aaggttgact ctgaagtcac agttttgaat          360
cctgatcaat atatttgtac tgttgctgaa ggtggacact tacacatgca aattgcggtt          420
aaaaacggcc gtggttatgt acctgcaagt gaaaataaaa ctgatgacat gcctatcggg          480
gttattcctg tagattcact tttttcacca attaaaaagg taaactacca agtagaaagt          540
acccgtgttg gtaagaaaga tgactacgat aaacttacgc tagaagtttg gaccgacggt          600
tcaatcacac ctagtgacgc tcttagtttt gcttctaaaa ttttgattga gcactttaaa          660
gtatttaaat tctcagatgc tcaaaccgat tttggtggcg aagtaatggt tgaaaaagaa          720
gacgataaga aagaacgtca acttgaaatg acaattgaag agttagacct ttctgttcgt          780
tcatacaact gcttaaagcg tgcaggtatc aacactcttc aagaattaac tgataagagt          840
gaatctgata tgatgcgcgt aagaaactta ggacgtaaat cattagaaga agttaaaaat          900
aaacttgcag atcttggact ttctcttcgt catgaagatt aa                            942
```

<210> SEQ ID NO 32
<211> LENGTH: 706
<212> TYPE: DNA
<213> ORGANISM: Lactobacillus rodentium

<400> SEQUENCE: 32

```
gttgtcgaac cattggaacg cggctttggg actactttag gtaactcact ccgtcgagta           60
ttattaactt ctattcccgg gacagcactt tcctacattc gaatcgatgg tgtattacat          120
gaattttcta ctgtacctgg cgttaaggaa gacgtcacta agattattct taatttgaag          180
aaactagaat taaagtcact ctcagatgaa aagaagatgg cagaaattga tgtaacaggc          240
ccagctgtgg taacagcagc agatttgaaa gtggattctg atgttgaagt cttaaatcct          300
gatcaatata tctgtacaat tgctgaaggc ggtcatttac gcatggatat tgctattaag          360
aatggtcgtg gttatgtacc agctagtgaa ataaggctg cggaagattt agcaattggt          420
gatattcctg tagattcact cttttcacca attagaaaag ttaattatca agttgaaaat          480
actcgtgttg gaaaaagaga tgactacgat aaattaactt tggaaatttg gactaatagt          540
tcaatcacac caaatgatgc ccttagtttt gcttcaaaga ttttacaaga acatttcaag          600
gtatttatgt ctactgatat ggatgcacaa cttgaagatg taatggttga aaaagaagac          660
aataagaatg ataagaaact tgagatgact attgaggagt tagatc                         706
```

<210> SEQ ID NO 33
<211> LENGTH: 706
<212> TYPE: DNA
<213> ORGANISM: Lactobacillus sp.

<400> SEQUENCE: 33

```
gttgtcgaac cattggaacg cggctttggg actactttag gtaactcact ccgtcgagta           60
ttattaactt ctattcccgg gacagcactt tcctacattc gaatcgatgg tgtattacat          120
gaattttcta ctgtacctgg cgttaaggaa gacgtcacta agattattct taatttgaag          180
aaactagaat taaagtcact ctcagatgaa aagaagatgg cagaaattga tgtaacaggc          240
ccagctgtgg taacagccgc agatttgaaa gtggattctg atgttgaagt cttaaatcct          300
```

-continued

```
gatcaatata tctgtacaat tgctgaaggc ggtcatttac gcatggatat tgctattaag    360
aatggtcgtg gttatgtacc agctagcgaa aataaggctg cggaagattt agcaattggt    420
gatattccag tagattcact cttttcacca attagaaaag ttaattatca agttgaaaac    480
actcgtgttg gaaaaagaga tgactacgat aaattaactt tggaaatttg gactaatagt    540
tcaatcacac caaatgatgc ccttagtttt gcttcaaaga ttttacaaga acacttcaag    600
gtatttatgt ctactgacat ggatgcacaa cttgaagatg tgatggttga aaaagaagac    660
aataagaatg ataagaaact tgagatgact attgaggagt tagatc               706
```

```
<210> SEQ ID NO 34
<211> LENGTH: 809
<212> TYPE: DNA
<213> ORGANISM: Lactobacillus sp.

<400> SEQUENCE: 34
ttgttgacca agaaaagtct tacggtaaat ttgttattga accacttgaa cgaggctacg     60
gtactacttt aggtaactca ttacgtcgag tattactgac ttctattcca ggcacagggc    120
ttgtttatgt tcaaattgac ggtgtcttgc acgaattttc aacagttcct ggagttagag    180
aagatgtcgc taagatgatt cttaacttaa agaagcttga attaaagtct ctatcagatg    240
aacaaaagac aatcgaattg gatgttgaag accagcaac tgtaacagct gatgatctga     300
aggttgatgc agatattcaa attttgaatc ctgatcaata catttgtacc attgctgaag    360
gtggacattt gcatatgcaa attgctgtca gaatggtcg tggttatgtt gcagcaagtg     420
ataacaagag cgaagacatg ccaattggtg tcattccagt tgattctctt ttttcaccaa    480
ttgagaaagt taattatcaa gttgaatcaa ctcgtgttgg taaaagagac gattttgaca    540
aactcacttt agagatttgg actgatggtt caatcaaacc taatgatgcc cttagttttg    600
ctgctaaaat tttagtagcg cactttaaag tgtttgaaac tgctgatgca ataccaaat     660 tcgatgatgt tatggtcgaa aaagaagacg atactgcaga gaagaagctt gaaatgacta    720
ttgaagagct cgatctttca gttcgttcgt acaattgtct taagcgtgcg ggtattaata    780
ctctgcaaga attaactgat aagactgaa                                      809
```

```
<210> SEQ ID NO 35
<211> LENGTH: 706
<212> TYPE: DNA
<213> ORGANISM: Lactobacillus iners

<400> SEQUENCE: 35
aagaagaatc atatggtaag tttgttgtcg aacctttaga acgcggtttt gggactactt     60
taggtaactc actccgtcgt gtcttattaa cttcaatttc aggtacggca ctttcttaca    120
ttatgattga tggtgtttta catgaatttt caacaattcc aggcgtaaga gaagatgtaa    180
ccaaaataat tcttaattta aagaaattgg aattaaagct cttagttgat gaagaaaaaa    240
tggttgaaat tgatgttgaa ggaccagcag ttgttacagc tgcagatctt aaagtcgatg    300
ctgatgttga atattaaac cctgatcagt atatttgtac tattgctgaa ggtggtcatt     360
tgcatatgag catcgcaatt aaaaatggtc gtggttatat tccggcaagt gaaaataaat    420
ctgatgatat gcctattggt gtaattccag ttgattcgct tttttcacct attaaaaaag    480
ttaattatca agttgaaaat gcacgtgtgg gtaagagaga tgattatgac aaactcactt    540
tagaattgtg gacggatggt tcaatcacac ctaatgatgc ccttagtttt gccgcaaaga    600 ttccttgaaga acactttaaa gtatttatgt ctgcagatat gagtgatcaa tttgctaatg    660
```

```
ttatgattga aaaagaagac aaatctaacg agaaaaagct tgagat                         706

<210> SEQ ID NO 36
<211> LENGTH: 809
<212> TYPE: DNA
<213> ORGANISM: Lactobacillus sp.

<400> SEQUENCE: 36
ttgttgacca agagaagtct tacggtaaat ttgttattga accacttgaa cgaggctttg          60
gtactacgtt aggtaactca ttacgtagag ttttactgac atctattcca ggtactggac         120
ttgtttatgt tcaaattgat ggtgtcttgc acgaattctc aacagttcct ggtgttagag         180
aagatgtagc aaagatgatt ttgaatttaa agaagcttga attaaagtct ctttcagatg         240
aacaaaaaat tattgaatta gacgttgaag gtccagctac agtaactgca gatgatctta         300
aagttgatgc agatattcaa attttgaatc ctgatcaata tatttgtact attgctgatg         360
gtggtcattt gcacatgcaa attgctgtca agaatggtcg aggctatgtt gctgcaagcg         420
acaacaagag tggggatatg ccaattgggg ttattcctgt tgattctcta ttttcaccaa         480
ttagaaaagt taattaccag gttgaatcaa ctcgtgttgg taaaagagat gactttgaca         540
aactcacttt agagatttgg actgatggtt caatcaaacc taatgatgcc cttagttttg         600
ctgctaagat tttagtagct cactttaaag tgtttgaaac tgctgatgca aatactaaat         660
tcaatgatgt tatgattgaa aaagaagatg atactgcaga gaaaaagctt gaaatgacaa         720
tcgaagagct tgatctttca gttcgttcct ataattgtct taaacgagca ggtattaata         780
ctttgcaaga gttaactgat aagactgaa                                            809

<210> SEQ ID NO 37
<211> LENGTH: 629
<212> TYPE: DNA
<213> ORGANISM: Lactobacillus iners

<400> SEQUENCE: 37
ttaggtaact cactccgtcg tgtcttatta acttcaattt caggtacggc actttcttac          60
attatgattg atggtgtttt acatgaattt tcaacaattc caggcgtaag agaagatgta         120
accaaaataa ttcttaattt aaagaaattg gaattaaagc tcttagttga tgaagaaaaa         180
atggttgaaa ttgatgttga aggaccagca gttgttacag ctgcagatct taaagtcgat         240
gctgatgttg aaatattaaa ccctgatcag tatatttgta ctattgctga aggtggtcat         300
ttgcatatga gcatcgcaat taaaaatggt cgtggttata ttccggcaag tgaaaataaa         360
tctgatgata tgcctattgg tgtaattcca gttgattcgc tttttttcacc tattaaaaaa        420 gttaattatc aagttgaaaa tgcacgtgtg ggtaagagag atgattatga caaactcact         480
ttagaattgt ggacggatgg ttcaatcaca cctaatgatg cccttagttt tgccgcaaag         540
attcttgaag aacactttaa agtatttatg tctgcagata tgagtgatca atttgctaat         600
gttatgattg aaaaagaaga caaatctaa                                            629

<210> SEQ ID NO 38
<211> LENGTH: 605
<212> TYPE: DNA
<213> ORGANISM: Lactobacillus iners

<400> SEQUENCE: 38
cactccgtcg tgtcttatta acttcaattt caggtacggc actttcttac attatgattg          60
```

-continued

```
atggtgtttt acatgaattt tcaacaattc caggcgtaag agaagatgta acaaaaataa        120
ttcttaattt aaagaaattg gaattaaagc tcttagttga tgaagaaaaa atggttgaaa        180
ttgatgttga aggaccagca gttgttacag ctgcagatct taaagtcgat gctgatgttg        240
aaatattaaa ccctgatcag tatatttgta ctattgctga aggtggtcat ttgcatatga        300
gcatcgcaat taaaaatggt cgtggttata ttccggcaag tgaaaataaa tctgatgata        360
tgcctattgg tgtaattcca gttgattcgc tttttttcacc tattaaaaaa gttaattatc       420
aagttgaaaa tgcacgtgtg ggtaagagag atgattatga caaactcact ttagaattgt        480
ggacggatgg ttcaatcaca cctaatgatg cccttagttt tgccgcaaag attcttgaag        540
aacactttaa agtatttatg tctgctgata tgagtgatca atttgctaat gttatgattg        600
aaaaa                                                                    605
```

```
<210> SEQ ID NO 39
<211> LENGTH: 346
<212> TYPE: DNA
<213> ORGANISM: Lactobacillus iners

<400> SEQUENCE: 39
tgaagaaaaa attgctgaaa tcgatgtaac tggaccagca attgtaactg ctgctgattt         60
gaaggtcgac tctgatattg aggtcttaaa tccagatcaa tatatttgta gtattgctga        120
tggtggccat ttgcatatga acgttgcgat caagactggt cgtggttatg ttcccgcaag        180
tgaaaacaag acagatgaca tgcctattgg tgtcatcccc gttgattcac tcttctcacc        240
aatcaaaaaa gttaactacc aagttgaaag tgctcgtgtt ggtaagagag atgactatga        300
caaattaact ttagaaattt ggactgatgg ttcaatcaca cctaat                       346
```

```
<210> SEQ ID NO 40
<211> LENGTH: 563
<212> TYPE: DNA
<213> ORGANISM: Lactobacillus iners

<400> SEQUENCE: 40
atgattgatg gtgttttaca tgaattttca acaattccag gcgtaagaga agatgtaacc         60
aaaataattc ttaatttaaa gaaattggaa ttaaagctct tagttgatga agaaaaaatg        120
gttgaaattg atgttgaagg accagcagtt gttacagctg cagatcttaa agtcgatgct        180
gatgttgaaa tattaaaccc tgatcagtat atttgtacta ttgctgaagg tggtcatttg        240
catatgagca tcgcaattaa aaatggtcgt ggttatattc cggcaagtga aaataaatct        300
gatgatatgc ctattggtgt aattccagtt gattcgcttt tttcacctat taaaaaagtt        360
aattatcaag ttgaaaatgc acgtgtgggt aagagagatg attatgacaa actcacttta        420
gaattgtgga cggatggttc aatcacacct aatgatgccc ttagttttgc cgcaaagatt        480
cttgaagaac actttaaagt atttatgtct gcagatatga gtgatcaatt tgctaatgtt        540
atgattgaaa agaagacaa atc                                                 563
```